United States Patent
Cai et al.

(10) Patent No.: US 10,144,764 B2
(45) Date of Patent: Dec. 4, 2018

(54) γ-AAPEPTIDES WITH POTENT AND BROAD-SPECTRUM ANTIMICROBIAL ACTIVITY

(71) Applicants: Jianfeng Cai, Tampa, FL (US); Youhong Niu, Tampa, FL (US); Haifan Wu, Tampa, FL (US); Shruti Padhee, Tampa, FL (US)

(72) Inventors: Jianfeng Cai, Tampa, FL (US); Youhong Niu, Tampa, FL (US); Haifan Wu, Tampa, FL (US); Shruti Padhee, Tampa, FL (US)

(73) Assignee: University of South Florida, Tampa, FL (US)

(*) Notice: Subject to any disclaimer, the term of this patent is extended or adjusted under 35 U.S.C. 154(b) by 105 days.

(21) Appl. No.: 15/292,162

(22) Filed: Oct. 13, 2016

(65) Prior Publication Data
US 2017/0058002 A1 Mar. 2, 2017

Related U.S. Application Data

(63) Continuation of application No. 14/374,018, filed as application No. PCT/US2013/022695 on Jan. 23, 2013, now Pat. No. 9,499,587.

(60) Provisional application No. 61/589,496, filed on Jan. 23, 2012.

(51) Int. Cl.
| | |
|---|---|
| A61K 38/00 | (2006.01) |
| C07K 7/56 | (2006.01) |
| A61K 38/08 | (2006.01) |
| A61K 38/12 | (2006.01) |
| G01N 33/569 | (2006.01) |
| A61K 45/06 | (2006.01) |
| A61K 49/00 | (2006.01) |
| C07K 7/06 | (2006.01) |
| C07K 7/64 | (2006.01) |
| C07K 1/10 | (2006.01) |
| C07K 1/16 | (2006.01) |
| A61K 47/54 | (2017.01) |

(52) U.S. Cl.
CPC .......... *C07K 7/56* (2013.01); *A61K 38/08* (2013.01); *A61K 38/12* (2013.01); *A61K 45/06* (2013.01); *A61K 47/543* (2017.08); *A61K 49/0056* (2013.01); *C07K 1/10* (2013.01); *C07K 1/16* (2013.01); *C07K 7/06* (2013.01); *C07K 7/64* (2013.01); *G01N 33/569* (2013.01); *A61K 38/00* (2013.01)

(58) Field of Classification Search
None
See application file for complete search history.

(56) References Cited

U.S. PATENT DOCUMENTS

2006/0135428 A1* 6/2006 Bridon ............... C07K 14/605
                                                        514/13.3
2008/0200647 A1* 8/2008 Varray ................. C07K 1/04
                                                        530/317

OTHER PUBLICATIONS

Wu, 2001, Tetrahedron, 57, 8107-8113 (Year: 2001).*
Alekshun, M.N., et al., "Molecular Mechanisms of Antibacterial Multidrug Resistance," *Cell*, Mar. 23, 2007, vol. 128, pp. 1037-1050.
Bai, G., et al., "Cellular uptake of an α-AApeptide," *Organic & Biomolecular Chemistry*, 2012, vol. 10, pp. 1149-1153.
Chen, C., et al., "Antibacterial Activities of Short Designer Peptides: a Link between Propensity for Nanostructuring and Capacity for Membrane Destabilization," *Biomacromolecules*, 2010, vol. 11, pp. 402-411.
Choi, S., et al., "De novo design and in vivo activity of conformationally restrained antimicrobial arylamide foldamers," *Proceedings of the National Academy of Sciences*, Apr. 28, 2009, vol. 106, No. 17, pp. 6968-6973.
Chongsiriwatana, N.P., et al., "Peptoids that mimic the structure, function, and mechanism of helical antimicrobial peptides," *Proceedings of the National Academy of Sciences USA*, Feb. 26, 2008, vol. 105, No. 8, pp. 2794-2799.
Chongsiriwatana, N.P., et al., "Short alkylated peptoid mimics of antimicrobial lipopeptides," *Antimicrobial Agents and Chemotherapy*, 2011, vol. 55, No. 1, pp. 417-420.
Fowler, S.A., et al., "Structure-function relationships in peptoids: Recent advances toward deciphering the structural requirements for biological function," *Organic & Biomolecular Chemistry*, 2009, vol. 7, pp. 1508-1524.
Friedrich, C.L., et al., "Antibacterial Action of Structurally Diverse Cationic Peptides on Gram-Positive Bacteria," *Antimicrobial Agents and Chemotherapy*, 2000, vol. 44, No. 8, pp. 2086-2092.
Ge, Y., et al., "In vitro antibacterial properties of pexiganan, an analog of magainin," *Antimicrobial Agents and Chemotherapy*, 1999, vol. 43, No. 4, pp. 782-788.

(Continued)

*Primary Examiner* — Satyanarayana R Gudibande
(74) *Attorney, Agent, or Firm* — Saliwanchik, LLoyd & Eisenschenk

(57) ABSTRACT

The present invention is directed to a novel class of antimicrobial agents called γ-AApeptides. The current invention provides various categories of γ-AApeptides, for example, linear γ-AApeptides, cyclic γ-AApeptides, and lipidated γ-AApeptides. γ-AApeptides of the current invention are designed to exert antimicrobial activity while being stable and non-toxic. γ-AApeptides also do not appear to lead to the development of microbial resistance in treated microorganisms. Thus, the disclosed γ-AApeptides can be used for the treatment of various medical conditions associated with pathogenic microorganisms.

20 Claims, 22 Drawing Sheets

(15 of 22 Drawing Sheet(s) Filed in Color)

(56) References Cited

OTHER PUBLICATIONS

Hancock, R.E.W., et al., "Antimicrobial and host-defense peptides as new anti-infective therapeutic strategies," *Nature Biotechnology*, Dec. 2006, vol. 24, No. 12, pp. 1551-1557.
Hicks, R.P., et al., "De Novo Design of Selective Antibiotic Peptides by Incorporation of Unnatural Amino Acids," *Journal of Medicinal Chemistry*, 2007, vol. 50, pp. 3026-3036.
Ivankin, A., et al., "Role of the Conformational Rigidity in the Design of Biomimetic Antimicrobial Compounds," *Angewandte Chemie International Edition*, 2010, vol. 49, pp. 8462-8465.
Karlsson, A.J., et al., "Antifungal Activity from 14-Helical β-Peptides," *Journal of the American Chemical Society*, 2006, vol. 128, pp. 12630-12631.
Kleiner, R.E., et al., "DNA-Templated Polymerization of Side-Chain-Functionalized Peptide Nucleic Acid Aldehydes," *Journal of the American Chemical Society*, 2008, vol. 130, pp. 4646-4659.
Marr, A.K., et al., "Antibacterial peptides for therapeutic use: obstacles and realistic outlook," *Current Opinion in Pharmacology*, 2006, vol. 6, pp. 468-472.
Matsunaga, T., et al., "Direct Count of Bacteria Using Fluorescent Dyes: Application to Assessment of Electrochemical Disinfection," *Analytical Chemistry*, 1995, vol. 67, pp. 4487-4490.
Mowery, B.P., et al., "Mimicry of Antimicrobial Host-Defense Peptides by Random Copolymers," *Journal of the American Chemical Society*, 2007, vol. 129, pp. 15474-15476.
Mowery, B.P., et al., "Structure-activity Relationships among Random Nylon-3 Copolymers That Mimic Antibacterial Host-Defense Peptides," *Journal of the American Chemical Society*, 2009, vol. 131, pp. 9735-9745.
Niu, Y., et al., "γ-AApeptides bind to RNA by mimicking RNA-binding proteins," *Organic and Biomolecular Chemistry*, 2011, vol. 9, pp. 6604-6609.
Niu, Y., et al., "γ-AApeptides: design, synthesis and evaluation," *New Journal of Chemistry*, 2011, vol. 35, pp. 542-545.
Niu, Y., et al., "Identification of γ-AApeptides with potent and broad-spectrum antimicrobial activity," *Chemical Communications*, 2011, vol. 47, pp. 12197-12199.
Padhee, S., et al., "Non-hemolytic α-AApeptides as antimicrobial peptidomimetics," *Chemical Communications*, 2011, vol. 47, pp. 9729-9731.
Patch, J.A., et al., "Helical Peptoid Mimics of Magainin-2 Amide," *Journal of the American Chemical Society*, 2003, vol. 125, pp. 12092-12093.
Schmitt, M.A., et al., "Interplay among Folding, Sequence, and Lipophilicity in the Antibacterial and Hemolytic Activities of α/β-Peptides," *Journal of the American Chemical Society*, 2007, vol. 129, pp. 417-428.
Scott, R.W., et al., "De novo designed synthetic mimics of antimicrobial peptides," *Current Opinion in Biotechnology*, 2008, vol. 19, pp. 620-627.
Sforza, S., et al., "A Peptide Nucleic Acid Embedding a Pseudopeptide Nuclear Localization Sequence in the Backbone Behaves as a Peptide Mimic," *European Journal of Organic Chemistry*, 2010, vol. 2010, pp. 2441-2444.
Tew, G.N., et al., "De Novo Design of Antimicrobial Polymers, Foldamers, and Small Molecules: From Discovery to Practical Applications," *Accounts of Chemical Research*, Jan. 2010, vol. 43, No. 1, pp. 30-39.
Violette, A., et al., "Mimicking Helical Antibacterial Peptides with Nonpeptidic Folding Oligomers," *Chemistry & Biology*, May 2006, vol. 13, pp. 531-538.
Williams, S.C., et al., "Distinguishing between living and nonliving bacteria: Evaluation of the vital stain propidium iodide and its combined use with molecular probes in aquatic samples," *Journal of Microbiological Methods*, 1998, vol. 32, pp. 225-236.
Wu, M., et al., "Mechanism of Interaction of Different Classes of Cationic Antimicrobial Peptides with Planar Bilayers and with the Cytoplasmic Membrane of *Escherichia coli,*" *Biochemistry*, 1999, vol. 38, pp. 7235-7242.
Zaiou, M., "Multifunctional antimicrobial peptides: therapeutic targets in several human diseases," *Journal of Molecular Medicine*, 2007, vol. 85, pp. 317-329.
Written Opinion in International Application No. PCT/US2013/022695, dated May 15, 2013, pp. 1-6.

\* cited by examiner

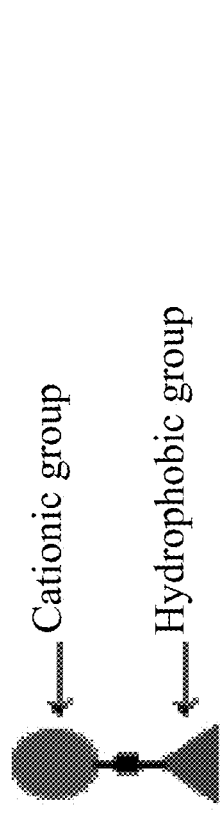
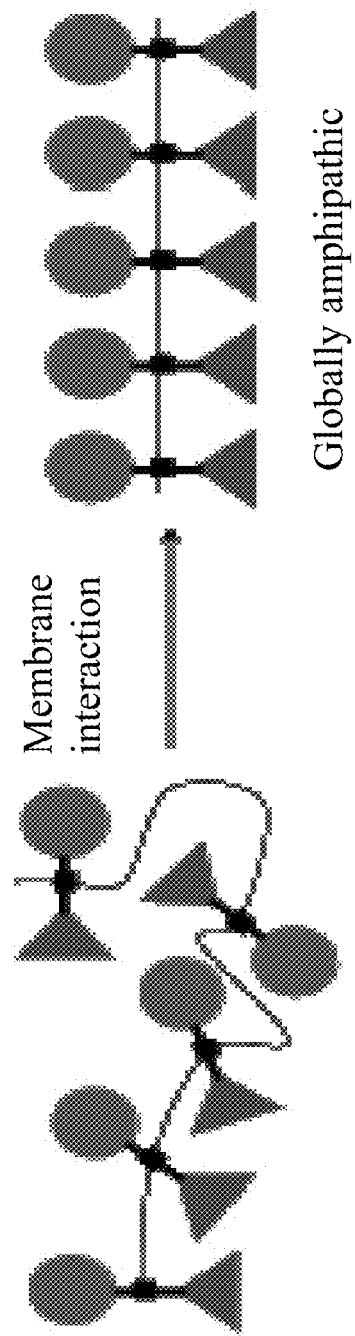
FIG. 1A
FIG. 1B

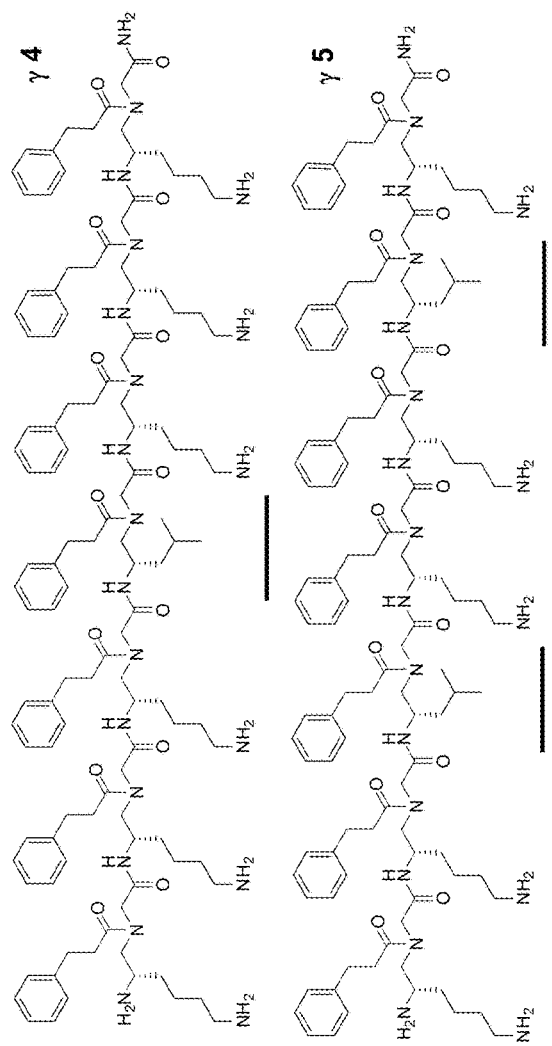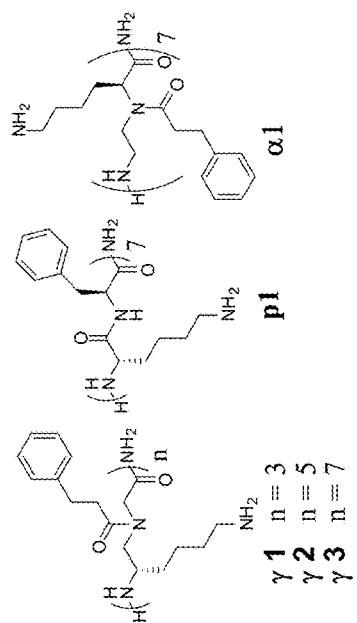
FIG. 2

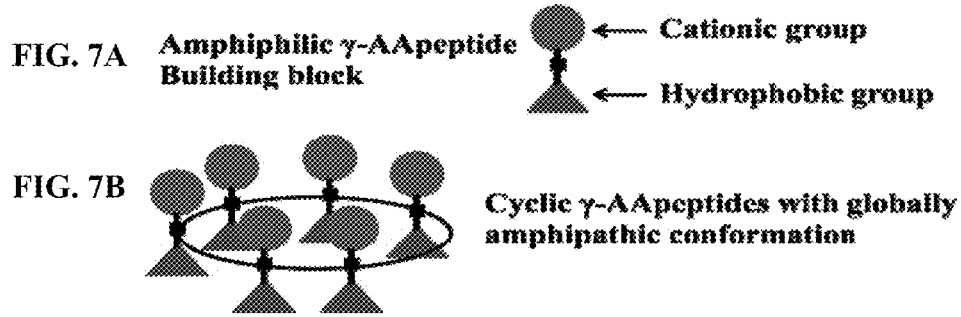
FIG. 7A  Amphiphilic γ-AApeptide Building block ← Cationic group
← Hydrophobic group
FIG. 7B  Cyclic γ-AApeptides with globally amphipathic conformation
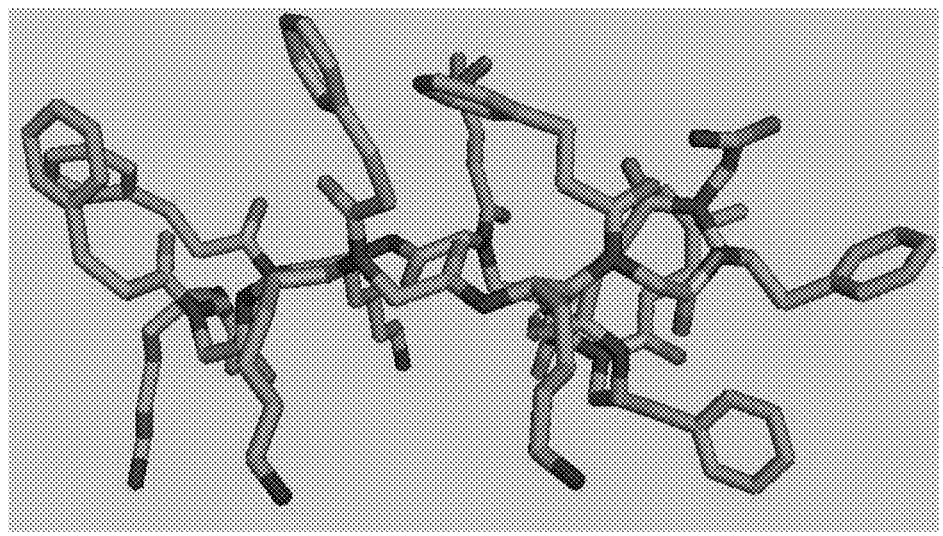
FIG. 8

γ-AAPEPTIDES WITH POTENT AND BROAD-SPECTRUM ANTIMICROBIAL ACTIVITY

CROSS REFERENCE TO RELATED APPLICATIONS

This application is a continuation of U.S. application Ser. No. 14/374,018, filed Jul. 23, 2014, which is the U.S. national stage application of International Patent Application No. PCT/US2013/022695, filed Jan. 23, 2013, which claims the benefit of U.S. Provisional Patent Application Ser. No. 61/589,496, filed Jan. 23, 2012, the disclosures of which are hereby incorporated by reference in their entirety, including all figures, tables and nucleic acid sequences.

BACKGROUND OF THE INVENTION

Antimicrobial peptides are small cationic amphiphilic peptides found in virtually all living organisms (Marr et al., 2006). They play an important role in innate immune defense against various infections (Hancock et al., 2006). In the last decade, there has been significant interest in the development of antimicrobial peptides because of the emergence of antibiotic resistance (Marr et al., 2006; Hancock et al., 2006).

Compared to conventional antibiotics, which target specific metabolic processes in bacteria (Alekshun et al., 2007), antimicrobial peptides are able to form amphipathic structures, where cationic and hydrophobic groups are segregated into two regions, so as to facilitate interaction with the negatively charged bacterial cytoplasmic membrane (Chongsiriwatana et al., 2008). Such interaction is based on the global chemical properties of peptides, rather than their precise sequence (Scott et al., 2008). Therefore, antimicrobial peptides are unlikely to be hindered by the resistance mechanisms observed for current antibiotic treatments (Marr et al., 2006). Furthermore, unlike conventional antibiotics, antimicrobial peptides exhibit broad-spectrum activity against both Gram-positive and Gram-negative bacteria, and even fungi and viruses (Marr et al., 2006; Hancock et al., 2006). They appear to be ideal antibiotic agents to supplement or replace existing treatments (Chongsiriwatana et al., 2008).

However, despite significant enthusiasm, there are intrinsic drawbacks associated with the development of peptide antibiotics due to the peptidic nature of antimicrobial peptides. These include potential immunoreactivity, susceptibility to enzymatic degradation, etc. (Zaiou, 2007). Non-natural peptidomimetic approaches that mimic antimicrobial peptides may circumvent these impediments by introducing amide bond isosteres, and modifying the peptide backbone so as to improve resistance to proteolytic hydrolysis (Violette et al., 2009). To this end, non-natural antimicrobial oligomers, such as β-peptides, peptoids, arylamides, and oilgourea, have been developed (Tew et al., 2009). However, their rational design sometimes turns out to be complicated due to the difficulty of introducing a variety of functional groups to fine-tune their activity and selectivity, and the inconsistency of their structure-activity-relationship (Fowler et al., 2009). Furthermore, recent research findings from many groups suggest that helical conformations, in which lipophilic and cationic side chains are globally segregated, are not necessary for antimicrobial activity (Schmitt et al., 2007; Mowery et al., 2007). Indeed, a pre-organized secondary structure seems unnecessary for bacterial killing (Scott et al., 2008); instead, oligomers with a strong propensity for helical conformation or conformational rigidity may lead to high hemolytic activity (Chongsiriwatana et al., 2008; Ivankin et al., 2010). Potent antimicrobial activity may actually require the presence of flexible or even random coiled backbones, where side groups are segregated into hydrophobic and cationic regions upon interaction with bacterial membranes (Scott et al., 2008; Ivankin et al., 2010), even if the amphiphilic conformation is irregular and non-helical.

There remains a need for the development of antimicrobial peptide mimetics suitable for the treatment of various microbial diseases. This application discloses a new class of antimicrobial peptide mimetics—γ-AApeptides developed by a simple design strategy. Certain γ-AApeptides were able to disrupt protein-protein interactions (Niu, Hu et al., 2011) and recognize nucleic acids with high affinity and specificity (Niu, Jones et al., 2011), and were highly resistant to protease degradation (Niu, Hu et al., 2011). Moreover, the synthesis and diversification of γ-AApeptides is efficient and straightforward (Niu, Hu et al., 2011), strengthening their potential to generate focused libraries for drug-lead screening. The antimicrobial γ-AApeptides disclosed herein are potent and have broad-spectrum activity, including activity against clinically-relevant strains that are unresponsive to most antibiotics. Also, γ-AApeptides are not prone to select for drug-resistant bacterial strains.

BRIEF SUMMARY OF THE INVENTION

The present invention is directed to a novel class of antimicrobial agents called γ-AApeptides (γ-AApeptides include linear γ-AApeptides, cyclic γ-AApeptides, and lipidated γ-AApeptides), which are designed to exert antimicrobial activity while being stable, non-toxic and avoiding development of resistance to the γ-AApeptides. Thus, the disclosed γ-AApeptides can be used for the treatment of various medical conditions associated with pathogenic microorganisms.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIGS. 1A-1B. Illustration of antimicrobial γ-AApeptide design. FIG. 1A, basic representation of amphiphilic γ-AApeptide structure; FIG. 1B, conformational change of γ-AApeptide upon interaction with bacterial cell membranes.

FIG. 2. The structures of oligomers tested in Example 1 for antimicrobial activity. Underlined building blocks are hydrophobic building blocks containing two hydrophobic side chains; the rest of the building blocks in the sequences are amphiphilic with one cationic and one hydrophobic side chain.

FIG. 6A shows the general synthesis of cyclic γ-AApeptides via on-resin cyclization. FIG. 6B shows the structures of cyclic γ-AApeptides. FIG. 6C shows the structure of linear γ-AApeptide γ5.

FIGS. 7A-7B. Illustration of cyclic antimicrobial γ-AApeptide design. FIG. 7A, basic representation of the amphiphilic γ-AApeptide building block; FIG. 7B, amphipathic cyclic γ-AApeptide with globally amphipathic conformation.

FIG. 8. The energy-minimized structure of HW-B-13. The computer modeling was carried out using ChemBioOffice MM2 energy minimization.

DETAILED DISCLOSURE OF THE INVENTION

Figure 3:
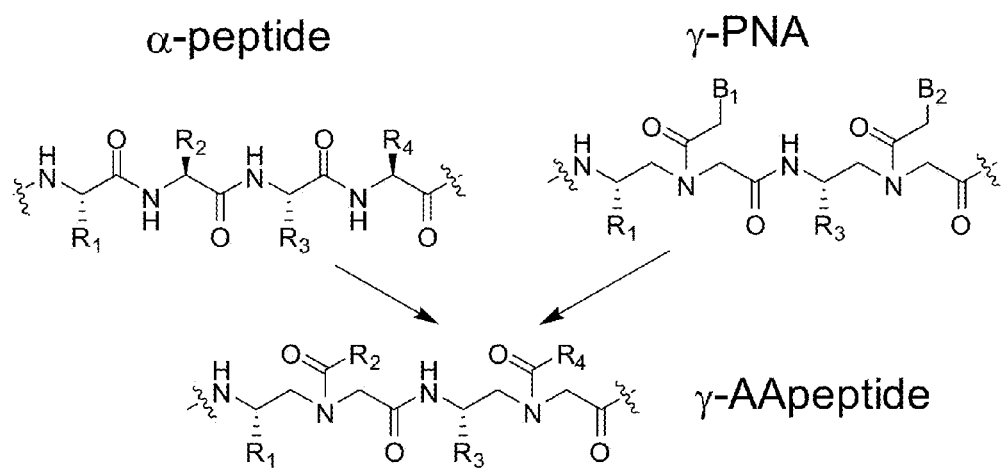
FIG. 3. The structure of an ca-peptide and the corresponding γ-AApeptide and γ-PNA.

The present invention is directed to a novel class of antimicrobial agents, γ-AApeptides, which include linear γ-AApeptides, cyclic γ-AApeptides, and lipidated γ-AApeptides. γ-AApeptides of the current invention are designed to exert antimicrobial activity while being stable, non-toxic and avoiding development of resistance to the γ-AApeptides. The antimicrobial agents of the current invention are termed "γ-AApeptides" (Niu, Hu et al., 2011) because they contain an N-acylated-N-aminoethyl amino acid unit (FIG. 3). In this unit, one side chain is connected to the γ-C in relation to the carbonyl group, and the other side chain is linked to the central N through acylation. As shown in FIG. 3, γ-AApeptides are able to project an identical number of side chains to natural peptides of the same length; therefore, they have great potential to be developed for peptide mimicry.

Compared to conventional peptides, γ-AApeptides are much superior in both their limitless potential for diversification and their inherent resistance to biodegradation. Thus, the disclosed γ-AApeptides can be used for the treatment of various medical conditions associated with pathogenic microorganisms.

One aspect of the present invention relates to a novel class of compounds (γ-AApeptides: which include linear γ-AApeptides, cyclic γ-AApeptides, and lipidated γ-AApeptides), which are based on positively charged (cationic) and/or hydrophobic groups (also referred to herein as subunits). In one embodiment, γ-AApeptides can comprise at least 5 or more cationic groups. Another embodiment provides γ-AApeptides that comprise both cationic groups and hydrophobic groups. In either of these embodiments, the γ-AApeptides disclosed herein have antimicrobial activity. γ-AApeptides disclosed herein can be between 5 and 50 subunits in length, preferably at least seven subunits in length and no more than 50 subunits in length.

Another aspect of the invention provides γ-AApeptides of the following formulas:

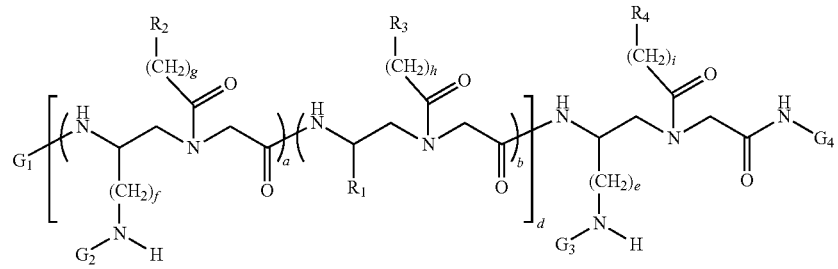

wherein:
a is 0, 1, 2, 3, 4, 5, 6, 7, 8, 9 or 10;
b is 0, 1, 2, 3, 4, 5, 6, 7, 8, 9 or 10;
d is 1, 2, 3, 4, 5, 6, 7, 8, 9 or 10;
e is 0, 1, 2, 3, 4, 5, 6, 7, 8, 9 or 10;
f is 0, 1, 2, 3, 4, 5, 6, 7, 8, 9 or 10;
g is 0, 1, 2, 3, 4, 5, 6, 7, 8, 9 or 10;

h is 0, 1, 2, 3, 4, 5, 6, 7, 8, 9 or 10;

i is 0, 1, 2, 3, 4, 5, 6, 7, 8, 9 or 10;

$G_1$, $G_2$, $G_3$ and $G_4$ are, independently, hydrogen or a blocking group;

$R_1$ is a straight or branched chain $C_1$ to $C_{10}$ alkyl group (e.g., a methyl, ethyl, n-propyl, isopropyl, cyclopropyl, n-butyl, isobutyl, s-butyl or t-butyl group); —$CH_2$—$CH_2$—S—$CH_3$; a —$(CH_2)_{1-5}$-aryl group; or an —$(CH_2)_{1-5}$-heteroaryl group, wherein the alkyl group, the aryl group or the heteroaryl group can be substituted or unsubstituted;

$R_2$ is an aryl group, a substituted aryl group, a heteroaryl group, or a substituted heteroaryl group;

$R_3$ is an aryl group, a substituted aryl group, a heteroaryl group, or a substituted heteroaryl group; and $R_4$ is an aryl group, a substituted aryl group, a heteroaryl group, or a substituted heteroaryl group.

In certain embodiments, $R_1$ is a methyl, ethyl, n-propyl, isopropyl, cyclopropyl, n-butyl, isobutyl, s-butyl or t-butyl group; $R_2$, $R_3$ and $R_4$ are phenyl groups; g, h and i are, independently, 2-4 (preferably 2); e and f are, independently, 2-5 (preferably 4); and $G_1$, $G_2$, $G_3$ and $G_4$ are, independently, hydrogen or a blocking group. The compounds of formula I can be linear, cyclic or lipidated (i.e., lipidated with a saturated or unsaturated lipid). γ-AApeptides can be lipidated at any reactive group on the γ-AApeptide; however, in some embodiments the peptides are lipidated at the amino terminus of the γ-AApeptide (see, for example, FIG. 2). As noted above, the lipid can be saturated or unsaturated and certain embodiments utilize a $C_{10}$-$C_{20}$ saturated or unsaturated lipid attached to the amino terminus of the γ-AApeptide. In various other embodiments, $C_{16}$-$C_{18}$ saturated or unsaturated lipids (e.g., palmitic or oleic acids) can be used.

The term "alkyl" refers to a straight, branched or cyclic chain hydrocarbon radical with only single carbon-carbon bonds. Representative examples include methyl, ethyl, propyl, isopropyl, cyclopropyl, butyl, isobutyl, tert-butyl, cyclobutyl, pentyl, cyclopentyl, hexyl, and cyclohexyl, all of which may be optionally substituted. Alkyl groups are $C_1$-$C_{12}$ and include alkyl groups that are $C_1$-$C_8$ in some embodiments.

The term "aryl" refers to aromatic groups which have 5-14 ring atoms and at least one ring having a conjugated pi electron system and includes carbocyclic aryl, heterocyclic aryl and biaryl groups, all of which may be optionally substituted. Carbocyclic aryl groups are groups which have, in various embodiments, 6-10 or 6-14 ring atoms wherein the ring atoms on the aromatic ring are carbon atoms. Carbocyclic aryl groups include monocyclic carbocyclic aryl groups and polycyclic or fused compounds such as optionally substituted naphthyl groups. Heterocyclic aryl or heteroaryl groups are groups which have, in various embodiments, 5-10 or 5-14 ring atoms wherein 1 to 4 heteroatoms are ring atoms in the aromatic ring and the remainder of the ring atoms being carbon atoms. Suitable heteroatoms include oxygen, sulfur, nitrogen, and selenium. Suitable heteroaryl groups include furanyl, thienyl, pyridyl, pyrrolyl, N-lower alkyl pyrrolyl, pyridyl-N-oxide, pyrimidyl, pyrazinyl, imidazolyl, and the like, all optionally substituted. The term "biaryl" represents aryl groups which have 5-14 atoms containing more than one aromatic ring including both fused ring systems and aryl groups substituted with other aryl groups. Such groups may be optionally substituted. Suitable biaryl groups include naphthyl and biphenyl. "Substituted aryl" and "substituted heteroaryl" refer to aryl and heteroaryl groups substituted with 1-3 substituents.

These substituents are selected from the group consisting of lower alkyl, lower alkoxy, lower perhaloalkyl, halo, hydroxy, and amino.

The term "lower", referred to herein in connection with organic radicals or compounds respectively, defines such as with up to and including 10, in one aspect up to and including 6, and in another aspect one to four carbon atoms. Such groups may be straight chain, branched, or cyclic.

The term "alkoxy" refers to the group alkyl —O—.

The term "perhalo" refers to groups wherein every C—H bond has been replaced with a C-halo bond on an aliphatic or aryl group. Suitable perhaloalkyl groups include —$CF_3$ and —$CFCl_2$.

The term "halogen" or "halo" refers to —F, —Cl, —Br and —I.

The terms "heterocyclic", "heterocyclic alkyl" or "heterocycloalkyl" refer to cyclic groups of 3 to 10 atoms, and in one aspect are 3 to 6 atoms, containing at least one heteroatom, in a further aspect 1 to 3 heteroatoms. Suitable heteroatoms include oxygen, sulfur, and nitrogen. Heterocyclic groups may be attached through a nitrogen or through a carbon atom in the ring. The heterocyclic alkyl groups include unsaturated cyclic, fused cyclic and spirocyclic groups. Suitable heterocyclic groups include pyrrolidinyl, morpholino, morpholinoethyl, and pyridyl.

In certain embodiments, R1 can be a group selected from:

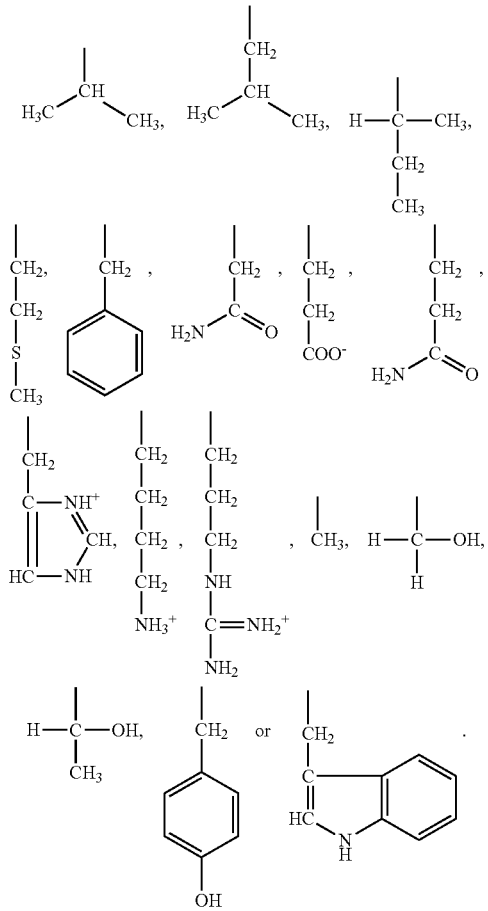

Two blocking (protecting) groups (t-Boc, Fmoc) are commonly used in solid-phase peptide synthesis. The t-Boc blocking group (tert-butyloxycarbonyl) is used to temporarily protect an α-amino group. Briefly, the t-Boc group is covalently bound to the amino group to suppress its nucleophilicity and the C-terminal amino acid is covalently linked to the resin through a linker. The t-Boc group is removed with acid, such as trifluoroacetic acid (TFA). This forms a positively-charged amino group, which is simultaneously neutralized and coupled to an incoming activated amino acid. The Fmoc protecting group (9-fluorenylmethyloxycarbonyl; Fmoc) can also be used and provides for a milder deprotection scheme. This method utilizes a base, usually piperidine in DMF, in order to remove the Fmoc group to expose the α-amino group for reaction with an incoming activated amino acid. Peptide synthesis using an Fmoc protecting group uses a base to remove the Fmoc group and provides for a neutral exposed amine group.

As used herein the term "antimicrobial activity" refers to the ability of a γ-AApeptide to kill or reduce the viability of a pathogenic microorganism selected from the group consisting of a prokaryotic organism, a eubacterium, an archaebacterium, a yeast, a fungus, an alga, a protozoan and a parasite.

The term γ-AApeptides includes linear γ-AApeptides, cyclic γ-AApeptides, and lipidated γ-AApeptides (also called lipo-γ-AApeptides), unless otherwise specified.

Another aspect of the invention provides cyclic γ-AApeptides. The invention also provides design and synthesis of cyclic γ-AApeptides. In an embodiment of the invention, the cyclic γ-AApeptides are synthesized by on-resin cyclization. The facile synthesis of cyclic γ-AApeptides may further expand the applications of γ-AApeptides in biomedical sciences. Cyclic peptidomimetics are expected to have improved antimicrobial activity due to constraints induced by cyclization. These cyclic γ-AApeptides are potent and active against fungi and Gram-positive and Gram-negative bacterial pathogens.

A further aspect of the invention provides lipidated γ-AApeptides. Lipidated γ-AApeptides of the current invention are produced by attaching lipid molecules to γ-AApeptides of the current invention. Lipidated γ-AApeptides, containing hydrophobic alkyl tails and short cationic γ-AApeptide sequences, display more potent, broad-spectrum, and highly selective antimicrobial activities against fungi and a series of clinically relevant Gram-positive and Gram-negative bacteria. Additionally, lipidated γ-AApeptides do not elicit drug resistance, for example, in *S. aureus*, even after 17 rounds of passaging.

In another aspect of the invention, compositions comprising a γ-AApeptide as disclosed herein are provided. In this aspect of the invention, one or more a γ-AApeptides are formulated in a pharmaceutically acceptable excipient or diluent suitable for administration to a subject. Techniques for formulation and administration of drugs may be found in "Remington's Pharmaceutical Sciences", Mack Publishing Co., Easton, Pa., latest edition, which is incorporated herein by reference.

The compositions described herein can also further comprise an additional therapeutically active agent (e.g., an antimicrobial agent or an antibiotic). Non-limiting examples of antimicrobial and antibiotic agents that are suitable for use in this context of the present invention include: mandelic acid, 2,4-dichlorobenzenemethanol, 4-[bis(ethylthio)methyl]-2-methoxyphenol, 4-epi-tetracycline, 4-hexylresorcinol, 5,12-dihydro-5,7,12,14-tetrazapentacen, 5-chlorocarvacrol, 8-hydroxyquinoline, acetarsol, acetylkitasamycin, acriflavin, alatrofloxacin, ambazon, amfomycin, amikacin, amikacin sulfate, aminoacridine, aminosalicylate calcium, aminosalicylate sodium, aminosalicylic acid, ammonium-sulfobituminat, amorolfin, amoxicillin, amoxicillin sodium, amoxicillin trihydrate, amoxicillin-potassium clavulanate combination, amphotericin B, ampicillin, ampicillin sodium, ampicillin trihydrate, ampicillin-sulbactam, apalcillin, arbekacin, aspoxicillin, astromicin, astromicin sulfate, azanidazole, azidamfenicol, azidocillin, azithromycin, azlocillin, aztreonam, bacampicillin, bacitracin, bacitracin zinc, bekanamycin, benzalkonium, benzethonium chloride, benzoxonium chloride, berberine hydrochloride, biapenem, bibrocathol, biclotymol, bifonazole, bismuth subsalicylate, bleomycin antibiotic complex, bleomycin hydrochloride, bleomycin sulfate, brodimoprim, bromochlorosalicylanilide, bronopol, broxyquinolin, butenafine, butenafine hydrochloride, butoconazol, calcium undecylenate, candicidin antibiotic complex, capreomycin, carbenicillin, carbenicillin disodium, carfecillin, carindacillin, carumonam, carzinophilin, caspofungin acetate, cefacetril, cefaclor, cefadroxil, cefalexin, cefalexin hydrochloride, cefalexin sodium, cefaloglycin, cefaloridine, cefalotin, cefalotin sodium, cefamandole, cefamandole nafate, cefamandole sodium, cefapirin, cefapirin sodium, cefatrizine, cefatrizine propylene glycol, cefazedone, cefazedone sodium salt, cefazolin, cefazolin sodium, cefbuperazone, cefbuperazone sodium, cefcapene, cefcapene pivoxil hydrochloride, cefdinir, cefditoren, cefditoren pivoxil, cefepime, cefepime hydrochloride, cefetamet, cefetamet pivoxil, cefixime, cefmenoxime, cefmetazole, cefmetazole sodium, cefminox, cefminox sodium, cefmolexin, cefodizime, cefodizime sodium, cefonicid, cefonicid sodium, cefoperazone, cefoperazone sodium, ceforanide, cefoselis sulfate, cefotaxime, cefotaxime sodium, cefotetan, cefotetan disodium, cefotiam, cefotiam hexetil hydrochloride, cefotiam hydrochloride, cefoxitin, cefoxitin sodium, cefozopran hydrochloride, cefpiramide, cefpiramide sodium, cefpirome, cefpirome sulfate, cefpodoxime, cefpodoxime proxetil, cefprozil, cefquinome, cefradine, cefroxadine, cefsulodin, ceftazidime, cefteram, cefteram pivoxil, ceftezole, ceftibuten, ceftizoxime, ceftizoxime sodium, ceftriaxone, ceftriaxone sodium, cefuroxime, cefuroxime axetil, cefuroxime sodium, cetalkonium chloride, cetrimide, cetrimonium, cetylpyridinium, chloramine T, chloramphenicol, chloramphenicol palmitate, chloramphenicol succinate sodium, chlorhexidine, chlormidazole, chlormidazole hydrochloride, chloroxylenol, chlorphenesin, chlorquinaldol, chlortetracycline, chlortetracycline hydrochloride, ciclacillin, ciclopirox, cinoxacin, ciprofloxacin, ciprofloxacin hydrochloride, citric acid, clarithromycin, clavulanate potassium, clavulanate sodium, clavulanic acid, clindamycin, clindamycin hydrochloride, clindamycin palmitate hydrochloride, clindamycin phosphate, clioquinol, cloconazole, cloconazole monohydrochloride, clofazimine, clofoctol, clometocillin, clomocycline, clotrimazol, cloxacillin, cloxacillin sodium, colistin, colistin sodium methanesulfonate, colistin sulfate, cycloserine, dactinomycin, danofloxacin, dapsone, daptomycin, daunorubicin, DDT, demeclocycline, demeclocycline hydrochloride, dequalinium, dibekacin, dibekacin sulfate, dibrompropamidine, dichlorophene, dicloxacillin, dicloxacillin sodium, didecyldimethylammonium chloride, dihydrostreptomycin, dihydrostreptomycin sulfate, diiodohydroxyquinolin, dimetridazole, dipyrithione, dirithromycin, DL-menthol, D-menthol, dodecyltriphenylphosphonium bromide, doxorubicin, doxorubicin hydrochloride, doxycycline, doxycycline hydrochloride, econazole, econazole nitrate, enilconazole, enoxacin, enrofloxacin, eosine, epicillin, ertapenem sodium, erythromycin, erythromycin estolate, erythromycin ethyl succinate, erythromycin lactobionate, erythromycin stearate, ethacridine, ethacridine lactate, ethambutol, ethanoic acid, ethionamide, ethyl alcohol, eugenol, exalamide, faropenem, fenticonazole, fenticonazole nitrate, fezatione, fleroxacin, flomoxef, flomoxef sodium, florfenicol, flucloxacillin, flucloxacillin sodium, flucloxacillin magnesium, fluconazole, flucytosine, flumequine, flurithromycin, flutrimazole, fosfomycin, fosfomycin calcium, fosfomycin sodium, framycetin, framycetin sulphate, furagin, furazolidone, fusafungin, fusidic acid, fusidic acid sodium salt, gatifloxacin, gemifloxacin, gentamicin antibiotic complex, gentamicin C1A, gentamycin sulfate, glutaraldehyde, gramicidin, grepafloxacin, griseofulvin, halazon, haloprogine, hetacillin, hetacillin potassium, hexachlorophene, hexamidine, hexetidine, hydrargaphene, hydroquinone, hygromycin, imipenem, isepamicin, isepamicin sulfate, isoconazole, isoconazole nitrate, isoniazid, isopropanol, itraconazole, josamycin, josamycin propionate, kanamycin, kanamycin sulphate, ketoconazole, kitasamycin, lactic acid, lanoconazole, lenampicillin, leucomycin A1, leucomycin A13, leucomycin A4, leucomycin A5, leucomycin A6, leucomycin A7, leucomycin A8, leucomycin A9, levofloxacin, lincomycin, lincomycin hydrochloride, linezolid, liranaftate, 1-menthol, lomefloxacin, lomefloxacin hydrochloride, loracarbef, lymecyclin, lysozyme, mafenide acetate, magnesium monoperoxophthalate hexahydrate, mecetronium ethylsulfate, mecillinam, meclocycline, meclocycline sulfosalicylate, mepartricin, merbromin, meropenem, metalkonium chloride, metampicillin, methacycline, methenamin, methyl salicylate, methylbenzethonium chloride, methylrosanilinium chloride, meticillin, meticillin sodium, metronidazole, metronidazole benzoate, mezlocillin, mezlocillin sodium, miconazole, miconazole nitrate, micronomicin, micronomicin sulfate, midecamycin, minocycline, minocycline hydrochloride, miocamycin, miristalkonium chloride, mitomycin C, monensin, monensin sodium, morinamide, moxalactam, moxalactam disodium, moxifloxacin, mupirocin, mupirocin calcium, nadifloxacin, nafcillin, nafcillin sodium, naftifine, nalidixic acid, natamycin, neomycin A, neomycin antibiotic complex, neomycin C, neomycin sulfate, neticonazole, netilmicin, netilmicin sulfate, nifuratel, nifuroxazide, nifurtoinol, nifurzide, nimorazole, niridazole, nitrofurantoin, nitrofurazone, nitroxolin, norfloxacin, novobiocin, nystatin antibiotic complex, octenidine, ofloxacin, oleandomycin, omoconazol, orbifloxacin, ornidazole, orthophenylphenol, oxacillin, oxacillin sodium, oxiconazole, oxiconazole nitrate, oxoferin, oxolinic acid, oxychlorosene, oxytetracycline, oxytetracycline calcium, oxytetracycline hydrochloride, panipenem, paromomycin, paromomycin sulfate, pazufloxacine, pefloxacin, pefloxacin mesylate, penamecillin, penicillin G, penicillin G potassium, penicillin G sodium, penicillin V, penicillin V calcium, penicillin V potassium, pentamidine, pentamidine diisetionate, pentamidine mesilas, pentamycin, phenethicillin, phenol, phenoxyethanol, phenylmercuriborat, PHMB, phthalylsulfathiazole, picloxydin, pipemidic acid, piperacillin, piperacillin sodium, pipercillin sodium-tazobactam sodium, piromidic acid, pivampicillin, pivcefalexin, pivmecillinam, pivmecillinam hydrochloride, policresulen, polymyxin antibiotic complex, polymyxin B, polymyxin B sulfate, polymyxin B1, polynoxylin, povidone-iodine, propamidin, propenidazole, propicillin, propicillin potassium, propionic acid, prothionamide, protiofate, pyrazinamide, pyrimethamine, pyrithion, pyrrolnitrin, quinoline, quinupristin-dalfopristin, resorcinol, ribostamycin, ribostamycin sulfate, rifabutin, rifampicin, rifamycin, rifapentine, rifaximin, ritiometan, rokitamycin, rolitetracycline, rosoxacin, roxithromycin, rufloxacin, salicylic acid, secnidazol, selenium disulphide, sertaconazole, sertaconazole nitrate, siccanin, sisomicin, sisomicin sulfate, sodium thiosulfate, sparfloxacin, spectinomycin, spectinomycin hydrochloride, spiramycin antibiotic complex, spiramycin B, streptomycin, streptomycin sulphate, succinylsulfathiazole, sulbactam, sulbactam sodium, sulbenicillin disodium, sulbentin, sulconazole, sulconazole nitrate, sulfabenzamide, sulfacarbamide, sulfacetamide, sulfacetamide sodium, sulfachlorpyridazine, sulfadiazine, sulfadiazine silver, sulfadiazine sodium, sulfadicramide, sulfadimethoxine, sulfadoxine, sulfaguanidine, sulfalene, sulfamazone, sulfamerazine, sulfamethazine, sulfamethazine sodium, sulfamethizole, sulfamethoxazole, sulfamethoxazol-trimethoprim, sulfamethoxypyridazine, sulfamonomethoxine, sulfamoxol, sulfanilamide, sulfaperine, sulfaphenazol, sulfapyridine, sulfaquinoxaline, sulfasuccinamide, sulfathiazole, sulfathiourea, sulfatolamide, sulfatriazin, sulfisomidine, sulfisoxazole, sulfisoxazole acetyl, sulfonamides, sultamicillin, sultamicillin tosilate, tacrolimus, talampicillin hydrochloride, teicoplanin A2 complex, teicoplanin A2-1, teicoplanin A2-2, teicoplanin A2-3, teicoplanin A2-4, teicoplanin A2-5, teicoplanin A3, teicoplanin antibiotic complex, telithromycin, temafloxacin, temocillin, tenoic acid, terbinafine, terconazole, terizidone, tetracycline, tetracycline hydrochloride, tetracycline metaphosphate, tetramethylthiuram monosulfide, tetroxoprim, thiabendazole, thiamphenicol, thiaphenicol glycinate hydrochloride, thiomersal, thiram, thymol, tibezonium iodide, ticarcillin, ticarcillin-clavulanic acid mixture, ticarcillin disodium, ticarcillin monosodium, tilbroquinol, tilmicosin, tinidazole, tioconazole, tobramycin, tobramycin sulfate, tolciclate, tolindate, tolnaftate, toloconium metilsulfat, toltrazuril, tosufloxacin, triclocarban, triclosan, trimethoprim, trimethoprim sulfate, triphenylstibinsulfide, troleandomycin, trovafloxacin, tylosin, tyrothricin, undecoylium chloride, undecylenic acid, vancomycin, vancomycin hydrochloride, viomycin, virginiamycin antibiotic complex, voriconazol, xantocillin, xibornol, zinc undecylenate and various combinations thereof.

The γ-AApeptides described herein can be used for the treatment of pathogenic microorganism infections. The option to include an additional therapeutically active agent may thus act synergistically against various bacteria, fungi and other microorganisms. The phrase "pathogenic microorganism" is used to describe any microorganism which can cause a disease or disorder in subjects/mammals in general, particularly in humans. The pathogenic microorganism may belong to any family of organisms such as, but not limited to, prokaryotic organisms, eubacteria, archaebacteria, eukaryotic organisms, yeast, fungi, algae, protozoans, and other parasites. Non-limiting examples of pathogenic microorganisms are *Plasmodium falciparum* and related malaria-causing protozoan parasites, *Acanthamoeba* and other free-living amoebae, *Aeromonas hydrophila*, *Anisakis* and related worms, *Acinetobacter baumanii*, *Ascaris lumbricoides*, *Bacillus cereus*, *Brevundimonas diminuta*, *Campylobacter jejuni*, *Clostridium botulinum*, *Clostridium perfringens*, *Cryptosporidium parvum*, *Cyclospora cayetanensis*, *Diphyllobothrium*, *Entamoeba histolytica*, certain strains of *Escherichia coli*, *Eustrongylides*, *Giardia lamblia*, *Klebsiella pneumoniae*, *Listeria monocytogenes*, *Nanophyetus*, *Plesiomonas shigelloides*, *Proteus mirabilis*, *Pseudomonas aeruginosa*, *Salmonella*, *Serratia odorifera*, *Shigella*, *Staphylococcus aureus*, *Stenotrophomonas maltophilia*, *Streptococcus*, *Trichuris trichiura*, *Vibrio cholerae*, *Vibrio parahaemolyticus*, *Vibrio vulnificus* and other vibrios, *Yersinia enterocolitica*, *Yersinia pseudotuberculosis* and *Yersinia kristensenii*.

As used herein, the terms "treating" and "treatment" include abrogating, substantially inhibiting, slowing or reversing the progression of a condition, substantially ameliorating clinical or aesthetical symptoms of a condition or substantially preventing the appearance of clinical or aesthetic symptoms associated with a condition. As used herein, the phrase "therapeutically effective amount" describes an amount of the composition being administered which will relieve to some extent one or more of the symptoms of the condition being treated. In some aspects of the invention, the phrase "therapeutically effective amount" refers to a reduction in the viability of a microorganism to be treated with the disclosed γ-AApeptides in vivo.

γ-AApeptides disclosed herein are antimicrobial agents which do not appear to induce resistance. The possible development of resistance to γ-AApeptides disclosed herein was assessed as discussed in the Examples. The results obtained in the antimicrobial-resistance studies showed that exposing bacteria to the disclosed γ-AApeptides did not result in development of resistance. γ-AApeptides disclosed herein display low or negligible hemolytic activity in the systems tested.

Diseases capable of being treated in accordance with the disclosed invention include, for example, actinomycosis, anthrax, aspergillosis, bacteremia, bacterial skin diseases, *Bartonella* infections, botulism, brucellosis, *Burkholderia* infections, *Campylobacter* infections, candidiasis, cat-scratch disease, *Chlamydia* infections, cholera, *Clostridium* infections, coccidioidomycosis, cryptococcosis, dermatomycoses, diphtheria, ehrlichiosis, typhus, *Escherichia coli* infections, *Fusobacterium* infections, gangrene, general infections, general mycoses, gonorrhea, Gram-negative bacterial infections, Gram-positive bacterial infections, histoplasmosis, impetigo, *Klebsiella* infections, legionellosis, leprosy, leptospirosis, *Listeria* infections, Lyme disease, malaria, maduromycosis, melioidosis, *Mycobacterium* infections, *Mycoplasma* infections, necrotizing fasciitis, *Nocardia* infections, onychomycosis, ornithosis, pneumococcal infections, pneumonia, *Pseudomonas* infections, Q fever, rat-bite fever, relapsing fever, rheumatic fever, *Rickettsia* infections, Rocky Mountain spotted fever, *Salmonella* infections, scarlet fever, scrub typhus, sepsis, sexually transmitted bacterial diseases, staphylococcal infections, streptococcal infections, surgical site infections, tetanus, tick-borne diseases, tuberculosis, tularemia, typhoid fever, urinary tract infections, *Vibrio* infections, yaws, *Yersinia* infections, *Yersinia pestis* infections, zoonoses and zygomycosis.

The γ-AApeptides disclosed herein have been shown to have high and selective affinity toward membranes of microorganisms. This feature can be used to couple a γ-AApeptides disclosed herein to a linker and/or labeling agent and used for the detection of infections in a subject/mammal, such as a rodent or a human. Accordingly, another aspect of the present invention provides an imaging probe for detecting a pathogenic microorganism, the imaging probe comprising a γ-AApeptide and at least one labeling agent attached thereto (preferably through a linker). As is apparent to one skilled in the art, commercially available linkers reactive with free amine groups (primary or secondary) can be coupled to γ-AApeptides disclosed herein. Likewise, commercially available labeling agents, such as fluorescent probes (e.g., IRDYE 800CW NHS ester) or chelating agents (e.g., DOTA (1,4,7,10-tetraazacyclododecane-1,4,7,10-tetraacetic acid)-NHS ester or NOTA (1,4,7-triazacyclononane-1,4,7-triacetic acid)-NHS ester), can also be linked to γ-AApeptides via primary or secondary amine groups. Non-limiting examples of commercially available linkers that can be coupled to γ-AApeptides disclosed herein include:

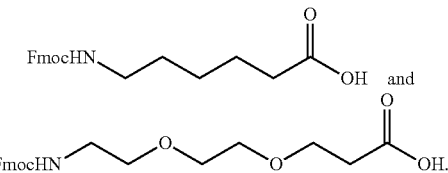

Diseases/infections capable of being diagnosed or identified in accordance with the disclosed invention in a subject/mammal (such as a rodent or a human) include, for example, actinomycosis, anthrax, aspergillosis, bacteremia, bacterial skin diseases, *Bartonella* infections, botulism, brucellosis, *Burkholderia* infections, *Campylobacter* infections, candidiasis, cat-scratch disease, *Chlamydia* infections, cholera, *Clostridium* infections, coccidioidomycosis, cryptococcosis, dermatomycoses, diphtheria, ehrlichiosis, typhus, *Escherichia coli* infections, *Fusobacterium* infections, gangrene, general infections, general mycoses, gonorrhea, Gram-negative bacterial infections, Gram-positive bacterial infections, histoplasmosis, impetigo, *Klebsiella* infections, legionellosis, leprosy, leptospirosis, *Listeria* infections, Lyme disease, malaria, maduromycosis, melioidosis, *Mycobacterium* infections, *Mycoplasma* infections, necrotizing fasciitis, *Nocardia* infections, onychomycosis, ornithosis, pneumococcal infections, pneumonia, *Pseudomonas* infections, Q fever, rat-bite fever, relapsing fever, rheumatic fever, *Rickettsia* infections, Rocky Mountain spotted fever, *Salmonella* infections, scarlet fever, scrub typhus, sepsis, sexually transmitted bacterial diseases, staphylococcal infections, streptococcal infections, surgical site infections, tetanus, tick-borne diseases, tuberculosis, tularemia, typhoid fever, urinary tract infections, *Vibrio* infections, yaws, *Yersinia* infections, *Yersinia pestis* infections, zoonoses and zygomycosis.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Design and Activity of γ-AApeptides

We prepared γ-AApeptide sequences (depicted in FIG. 2) and tested their antimicrobial activity against a range of clinically-relevant Gram-negative and Gram-positive bacteria, as well as the fungus *C. albicans*. γ1, γ2, γ3 are γ-AApeptides of different lengths that are composed of amphiphilic γ-AApeptide building blocks. γ4 contains one hydrophobic building block while γ5 contains two hydrophobic building blocks, an attempt to tune overall hydrophobicity of γ-AApeptides. As controls, we included AMP magainin II (ml) (Padhee et al., 2011), a 14-mer conventional peptide p1 (Padhee et al., 2011) with alternative phenylalanine and lysine residues, and the most potent antimicrobial α-AApeptide α1 reported by us recently (Padhee et al., 2011). The antimicrobial activity of these oligomers was tested and listed in Table 1. Their hemolytic activity was also tested to evaluate their selectivity.

A few sequences show very potent broad-spectrum activities against fungi and a series of clinically-relevant Gram-positive and Gram-negative bacteria, including pathogens that are unresponsive to most antibiotics (Table 1). The control sequence p1, which contains alternative phe and lys residues, the functional groups identical to γ3, does not show any antimicrobial activity at all. Such an observation can be explained by the peptide's intrinsic folding propensity (Padhee et al., 2011). Meanwhile, longer sequences are more potent and exhibit broad-spectrum activity, compared to shorter sequences with similar structures, as seen for the activities of γ1-γ3. This seems to indicate that the number of cationic charges is important for interaction with bacterial membranes. Notably, γ3 is more potent and has a broader spectrum of activity as compared to α3 (which has the same functional groups).

mimetics reported to date. Most significantly, it arrested the growth of the USA100 lineage MRSA strain with extreme potency. This observation is of particular importance as this strain displays resistance to a wealth of existing antimicrobial agents, and is broadly multi-drug resistant. As such, this may satisfy urgent needs in hospitals for new therapeutics, since this strain has been identified as the most prevalent cause of hospital-associated infections in the United States, and almost no current antibiotics can effectively target it. γ5 also potently inhibits *B. anthracis*, which is known to cause the highly lethal condition anthrax. All tested γ-AApeptides have excellent selectivity for bacteria and spare human blood cells, since the majority of them have $H_{50}$ of more than 500 μg/ml; even the most hemolytic sequence γ5 still has a selectivity of at least 60-fold.

One of the biggest challenges for conventional antibiotics is their susceptibility to the development of resistance, which quickly abolishes their efficacy. This situation has

TABLE 1

The antimicrobial and hemolytic activities of oligomers. Magainin II is a natural amphipathic antimicrobial peptide used as the comparison here. The sequences showing broad-spectrum antimicrobial activity (γ3-γ5 and α1) are designated with an *.

| Organism | MIC (μg/ml) | | | | | | | |
|---|---|---|---|---|---|---|---|---|
| | γ1 | γ2 | γ3* | γ4* | γ5* | p1 | α1* | M1 |
| Gram-negative | | | | | | | | |
| E. coli | >100 | 25 | 2.5-5 | 2.5-5 | 2.5-5 | >100 | 4.5 | 40 |
| K. pneumoniae (causing pneumonia) | >100 | >100 | >100 | >100 | 5 | >100 | >100 | >100 |
| Gram-Positive | | | | | | | | |
| B. subtilis | >100 | 5 | 2.5 | 2.5 | 2 | >100 | 2 | 40 |
| S. epidermidis (multi-drug resistant) | >100 | >100 | 6.25-12.5 | 3.1-6.25 | 3.1-6.25 | >100 | 10 | >100 |
| E. faecalis (vancomycin-resistant) | >100 | >100 | 12.5-25 | 12.5-25 | 3.1-6.25 | >100 | 75 | 75 |
| S. aureus (methicillin-resistant) | >100 | >100 | 12.5-25 | 3.1-6.25 | 5 | >100 | 75 | >100 |
| MRSA USA100 (leading hospital-associated strain, unresponsive to almost all antibiotics) | — | — | — | — | 5 | — | >100 | >100 |
| B. anthracis (lethal bioweapon) | — | — | 25-50 | 25-50 | 5 | — | >100 | >100 |
| Fungi | >100 | >100 | | | | | | |
| C. albicans | >500 | >500 | 12.5-25 | 12.5-25 | 5-10 | >100 | 20-30 | 75 |
| Hemolysis ($H_{50}$) | | | >500 | >500 | 300 | >500 | >500 | >500 |

Figure 4A:
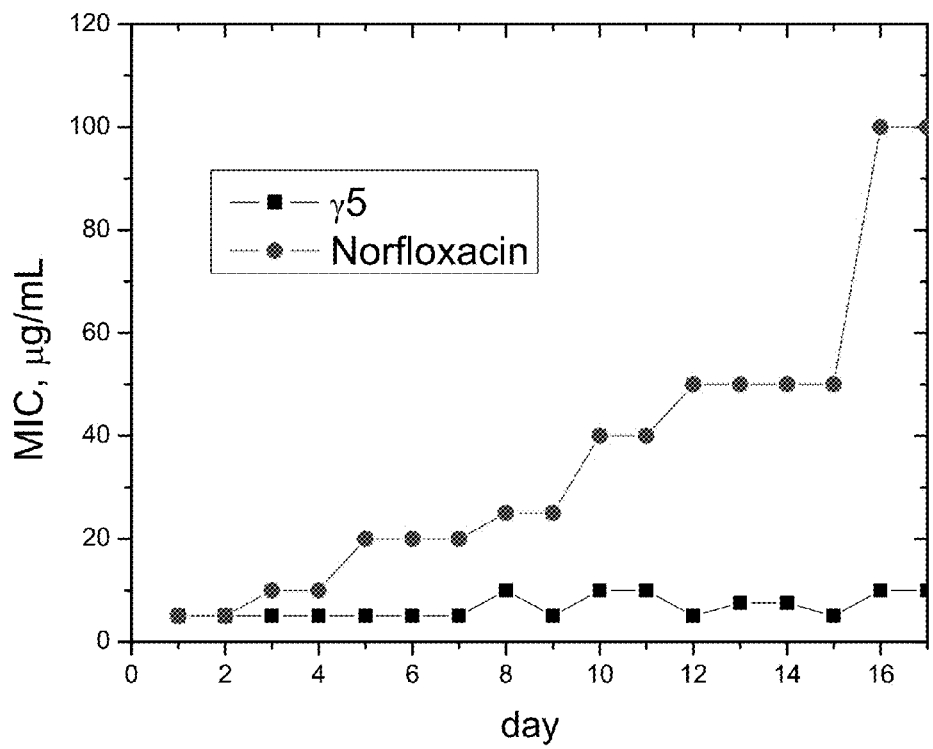
FIGS. 4A and B. The development of resistance by *S. aureus* ATCC 33592 towards γ5 and norfloxacin (FIG. 4A) and lipidated γAA2 and norfloxacin (FIG. 4B).

The further development of antimicrobial γ-AApeptides based on the lead γ3 yielded more potent sequences. As an initial attempt, we introduced a simple hydrophobic building block to tune the overall hydrophobicity and hydrophilicity of γ3, in order to evaluate the feasibility to tune the antimicrobial activity of γ-AApeptides. Such an effort led to the discovery of γ5, in which two amphiphilic building blocks are replaced with hydrophobic building blocks (containing two hydrophobic side chains) compared to γ3, and only one side chain difference from γ4. While γ4 are not active against Gram-negative *K. pneumoniae*, γ5 potently inhibited the growth of all tested Gram-negative and Gram-positive bacteria, and also the fungus *C. albicans*. In fact, γ5 is amongst the most potent and broad-spectrum antimicrobial peptidobecome more severe in recent years, and may lead to outbreaks of deadly infectious diseases that are untreatable. To investigate the potential for bacteria to develop resistance against the treatment of γ-AApeptides, meticillin-resistant *S. aureus* (ATCC 33592) was serially passaged in half-MIC concentrations of γ5 and lipidated γAA2 (see Example 2), and new MIC values were determined every 24 h. As a positive control, parallel cultures were exposed to serial 2-fold dilutions of the antibiotic norfloxacin (Choi et al., 2009). After 17 days, virtually no change in the MIC occurred for γ5 over the 17 passages, whereas the MIC for norfloxacin started to increase after just three passages, and the organism developed profound resistance after 17 passages (MIC increased >20-fold). These results demonstrate that MRSA strains do not readily develop resistance to γ-AApeptide γ5 or lipidated γAA2 (see FIGS. 4A and B).

In summary, we reported the identification of a new class of antimicrobial peptidomimetics, γ-AApeptides, with potency and broad-spectrum activity far superior to previous reported α-peptides (Padhee et al., 2011). These γ-AApeptides likely inhibit bacterial growth by mimicking conventional antimicrobial peptides through membrane disruption. This is an important observation as it suggests the potential for virtually no development of resistance towards these agents. Additionally, our approach to the development of antimicrobial peptides avoids tedious and sometimes ineffective secondary structure development as has been observed in the design of other classes of antimicrobial peptidomimetics.

1. General Experimental Methods for Example 1

α-amino acid esters and Knorr resin (0.66 mmol/g, 200-400 mesh) were provided by Chem-Impex International, Inc. All other reagents and solvents were purchased from either Sigma-Aldrich or Fisher Scientific. α-peptides m1 and p1 were purchased from USF peptide facility and used without further purification. γ-AApeptide building blocks were synthesized following the previously reported procedure (Niu, Hu et al., 2011). NMR spectra of γ-AApeptide building blocks were obtained on a Varian Inova 400 instrument. Linear γ-AApeptides were prepared on Knorr resin in peptide synthesis vessels on a Burrell Wrist-Action shaker. The linear γ-AApeptides were analyzed and purified on an analytical and a preparative Waters HPLC system, respectively, and then dried on a Labcono lyophilizer. Molecular weights of γ-AApeptides were identified on a Bruker AutoFlex MALDI-TOF mass spectrometer.

2. Synthesis (Niu, Hu et al., 2011) and Characterization of γ-AApeptide Building Blocks γ-AApeptide building blocks were synthesized following the previously reported procedure (Niu, Hu et al., 2011, the disclosures of which are hereby incorporated by reference in their entireties).

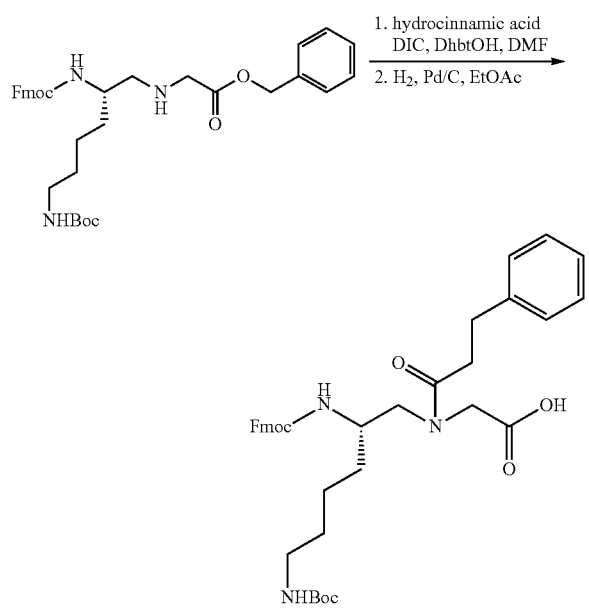

1

Compound 1. Yield 65% (two steps). $^1$H NMR (DMSO-$d_6$, 400 MHz) δ=7.84 (d, J=7.2 Hz, 2H), 7.65-7.60 (m, 2H), 7.37 (t, J=7.6 Hz, 2H), 7.27 (m, 2H), 7.22-7.08 (m, 5H), 6.71 (b, 1H), 4.28-4.02 (m, 3H), 3.98-3.57 (m, 2H), 3.47-3.44 (m, 1H), 3.45 (dd, J=5.2, 13.2 Hz, 1H), 3.04-2.99 (m, 1H), 2.85-2.84 (m, 2H), 2.73-2.53 (m, 3H), 2.47-2.31 (m, 1H), 1.33-1.11 (m, 15H). $^{13}$C NMR (DMSO-$d_6$, 100 MHz) δ 172.7, 172.3, 156.5, 156.4, 156.0, 144.4, 144.3, 144.28, 144.2, 141.9, 141.8, 141.2, 128.7, 128.61, 128.59, 128.0, 127.5, 127.4, 126.2, 126.1, 125.62, 125.58, 125.5, 120.5, 77.7, 65.7, 65.6, 52.5, 51.1, 50.2, 51.1, 50.11, 50.09, 48.3, 47.3, 41.1, 34.5, 34.0, 32.1, 31.7, 31.2, 31.0, 29.8, 29.7, 28.7, 23.7, 23.3, 23.27. HR-ESI: [M+H]$^+$ cacl: 644.3330. found: 644.3338.

2

Compound 2. Yield 53% (two steps). $^1$H NMR (DMSO-$d_6$, 400 MHz) δ=7.83 (d, J=8.0 Hz, 2H), 7.65-7.59 (m, 2H), 7.38-7.07 (m, 10H), 4.29-4.21 (m, 2H), 4.17-4.10 (m, 1H), 3.96-3.67 (m, 3H), 3.47-3.2.99 (m, 2H), 2.75-2.64 (m, 2H), 2.63-2.55 (m, 1H), 2.42-2.35 (m, 1H), 1.53-1.51 (m, 1H), 1.30-1.19 (m, 1H), 1.10-1.07 (m, 1H), 0.83-0.76 (m, 6H). $^{13}$C NMR (DMSO-$d_6$, 100 MHz) δ 172.7, 156.4, 56.3, 144.4, 144.3, 144.25, 144.17, 129.3, 128.7, 128.6, 128.57, 128.00, 127.7, 127.5, 127.4, 126.2, 126.1, 125.6, 125.5, 11.8, 120.5, 65.6, 52.7, 51.5, 48.2, 47.3, 41.6, 41.6, 34.7, 34.6, 34.1, 31.3, 31.0, 24.7, 24.9, 23.8, 22.2, 21.9. HR-ESI: [M+H]$^+$ cacl: 529.2697. found: 529.2695.

3. Solid Phase Synthesis, Purification and Characterization of γ-AApeptides

γ-AApeptides were prepared on Knorr resin in peptide synthesis vessels on a Burrell Wrist-Action shaker following standard Fmoc chemistry protocol of solid phase peptide synthesis using synthesized γ-AApeptide building blocks. Each coupling cycle included an Fmoc deprotection using 20% Piperidine in DMF, and 8 h coupling of 1.5 equiv of γ-AApeptide building blocks onto resin in the presence 4 equiv of DIC (diisopropylcarbodiimide)/DhbtOH (3-4-Dihydro-3-hydroxy-4-oxo-1-2-3-benzotriazine) in DMF. After desired sequences were assembled, they were transferred into 4 ml vials and cleaved from solid support in 50:48:2 TFA/CH$_2$Cl$_2$/triisopropylsilane overnight. Then solvent was evaporated and the residues were analyzed and purified on an analytical (1 ml/min) and a preparative (20 ml/min) Waters HPLC system, respectively, using 5% to 100% linear gradient of solvent B (0.1% TFA in acetonitrile) in A (0.1%

TFA in water) over 40 min, followed by 100% solvent B over 10 min. The HPLC traces were detected at 215 nm. The desired fractions were eluted as single peaks at >95% purity. They were collected and lyophilized. The molecular weights of γ-AApeptides were obtained on a Bruker AutoFlex MALDI-TOF mass spectrometer using ca-cyano-4-hydroxy-cinnamic acid (shown in Table 2).

TABLE 2

MS analysis of γ-AApeptides (γ1-γ5).

| γ-AApeptides | molecular weight (actual) | molecular weight (found) |
|---|---|---|
| γ1 | 927.2 | 927.4 (MALDI) |
| γ2 | 1534.0 | 1535.0 (M + H)$^+$ (LC – MS) |
| γ3 | 2140.8 | 2141.3 (LC – MS) |
| γ4 | 2125.8 | 2125.8 (MALDI) |
| γ5 | 2110.8 | 2111.7 (M + H)$^+$ (MALDI) |

4. Antimicrobial Assays

The microbial organisms used were *E. coli* (JM109), *B. subtilis* (BR151), *S. epidermidis* (RP62A), *C. albicans* (ATCC 10231), *E. faecalis* (ATCC 700802), *S. aureus* (ATCC 33592), *K. pneumoniae* (ATCC 13383), methicillin-resistant *S. aureus* (MRSA, USA100 lineage), and *B. anthracis*. The minimum inhibitory concentration (MIC) is the lowest concentration that completely inhibits the growth of bacteria in 24 h. The highest concentration tested for antimicrobial activity was 100 μg/ml. The antimicrobial activities of the γ-AApeptides were determined in sterile 96-well plates by the broth micro-dilution method. Bacterial cells (Patch et al., 2003) and fungi (Karlsson et al., 2006) were grown overnight at 37° C. in 5 ml medium, after which a bacterial suspension (approximately 10$^6$ CFU/ml) or fungal suspension of *Candida albicans* (ATCC 10231) (approximately 10$^3$ CFU/ml) in Luria broth or trypticase soy was prepared. Aliquots of 50 μL bacterial or fungal suspension were added to 50 μL of medium containing the γ-AApeptides for a total volume of 100 μL in each well. The γ-AApeptides were prepared in PBS buffer in 2-fold serial dilutions, with the final concentration range of 0.5 to 100 μg/ml. Plates were then incubated at 37° C. for 24 h (for bacteria) or 48 h (for *Candida albicans* (ATCC 10231)). The lowest concentration at which complete inhibition of bacterial growth (determined by a lack of turbidity) is observed throughout the incubation time is defined as the minimum inhibitory concentration (MIC). The experiments were carried out independently three times in duplicate.

5. Drug Resistance Study (Choi et al., 2009)

The initial MIC of γ5 and control antibiotic norfloxacin against *S. aureus* was obtained as described above. Bacteria from duplicate wells at the concentration of one-half MIC were then used to prepare the bacterial dilution (approximately 10$^6$ CFU/ml) for the next experiment. These bacterial suspensions were then incubated with γ5 and norfloxacin respectively. After incubation at 37° C. for 24 h, the new MIC was determined. The experiment was repeated each day for 17 passages.

6. Hemolysis Assay

Freshly drawn human red blood cells (hRBC's) with additive K$_2$ EDTA (spray-dried) were washed with PBS buffer several times and centrifuged at 1000 g for 10 min until a clear supernatant was observed. The hRBC's were resuspended in 1×PBS to get a 5% v/v suspension. Two-fold serial dilutions of γ-AApeptides dissolved in 1×PBS from 250 μg/ml through 1.6 μg/ml were added to a sterile 96-well plate to make up a total volume of 50 μL in each well. Then 50 μL of 5% v/v hRBC solution was added to make up a total volume of 100 μL in each well. The 0% hemolysis point and 100% hemolysis point were determined in 1×PBS and 0.2% Triton-X-100, respectively (Patch et al., 2003). The plate was then incubated at 37° C. for 1 h and centrifuged at 3500 rpm for 10 min. The supernatant (30 μL) was diluted with 100 μL of 1×PBS and absorption was detected by measuring the optical density at 360 nm by Biotek Synergy HT microtiter plate reader. % hemolysis was determined by the following equation:

$$\% \text{ hemolysis} = (\text{Abs}_{sample} - \text{Abs}_{PBS})/(\text{Abs}_{Triton} - \text{Abs}_{PBS}) \times 100$$

H50 is the concentration of γ-AApeptide amphiphiles at which 50% hemolysis was observed. The highest concentration tested in the hemolytic assay was 500 μg/ml.

7. Fluorescence Microscopy

A double staining method with DAPI (4',6-Diamidino-2-phenylindole dihydrochloride, Sigma, >98%) and PI (Propidium iodide, Sigma) as fluorophores was used to visualize and differentiate the viable from the dead *E. coli* or *B. subtilis* cells. DAPI as a double-stranded DNA binding dye stains all bacterial cells irrespective of their viability, whereas Ethidium derivatives such as propidium iodide (PI) are capable of passing through only damaged cell membranes and intercalate with the nucleic acids of injured and dead cells to form a bright red fluorescent complex (Matsunaga et al., 2005). The cells were first stained with PI and then with DAPI. Bacterial cells were grown until they reached the mid-logarithmic phase and then they (~2×10$^6$ cells) were incubated with the γ-AApeptide γ5 at a concentration of 2×MIC (10 μg/ml) for 2 h. Then the cells were pelleted by centrifugation at 3000 g for 15 min in an Eppendorf microcentrifuge. The supernatant was then decanted and the cells were washed with 1×PBS several times and then incubated with PI (5 μg/ml) in the dark for 15 min at 0° C. The excess PI was removed by washing the cells with 1×PBS several times. Then the cells were incubated with DAPI (10 μg/ml in water) for 15 mins in the dark at 0° C. The DAPI solution was removed and cells were washed with 1×PBS several times.

Controls were performed following the exact same procedure for bacteria without the addition of γ5. The bacterial cells were then examined by using the Zeiss Axio Imager Z1 optical microscope with an oil-immersion objective (100×) (Williams et al., 1998).

Example 2—Derivatization of γ-AApeptides

Figure 4B:
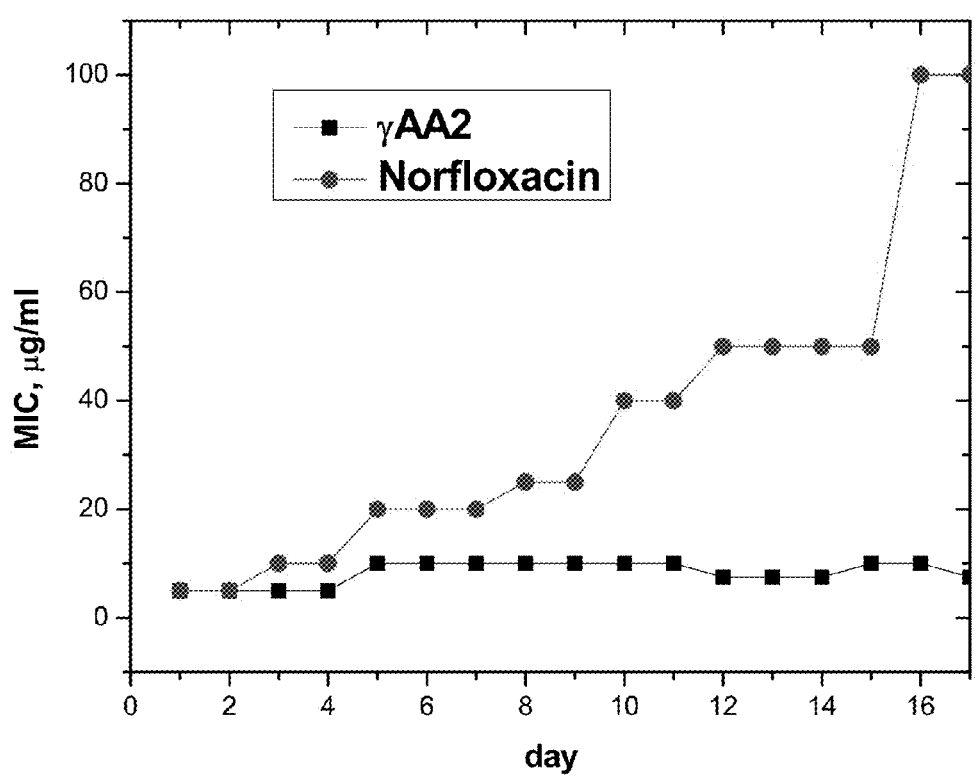
Figure 5:
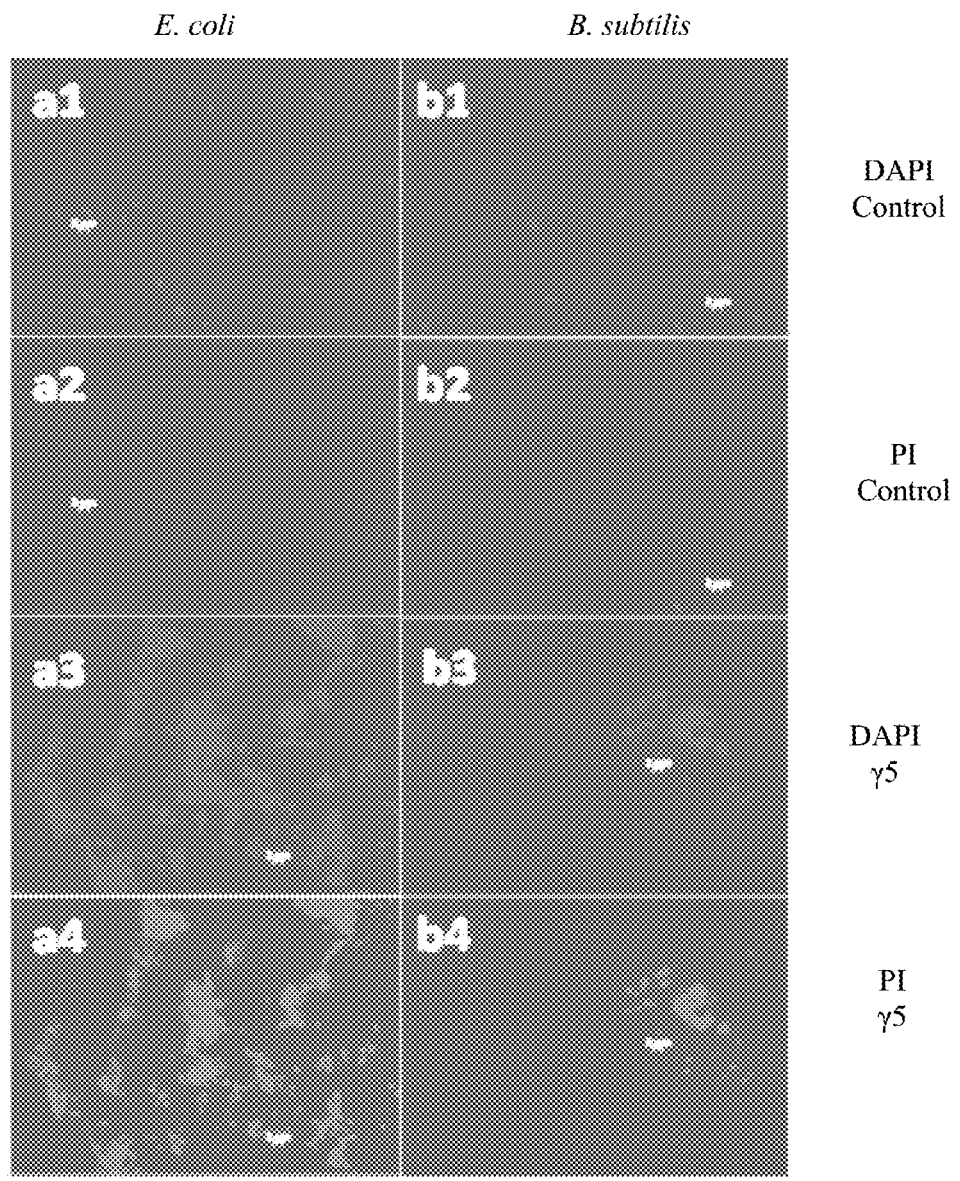
FIG. 5. Fluorescence micrographs of *E. coli* and *B. subtilis* treated with 10 μg/ml γ-AApeptide γ5 for 2 h. a1-a4, *E. coli*. a1, control, no treatment, DAPI stained; a2, control, no treatment, PI stained; a3, γ5 treatment, DAPI stained; a4, γ5 treatment, PI stained. b1-b4, *B. subtilis*. b1, control, no treatment, DAPI stained; b2, control, no treatment, PI stained; b3, γ5 treatment, DAPI stained; b4, γ5 treatment, PI stained. Scale bar: 2 μm for *E. coli* and for *B. subtilis*.

Lipidated and cyclic γ-AApeptides are also show potent and broad-spectrum activity. The most potent linear sequence, γAA1 (γAA5 of Example 1), is also listed in Table 3. For comparison, pexiganan (in Phase III clinical trials, a synthetic antimicrobial peptide) is also included; the data is taken from Chongsiriwatana et al. (2008), Chongsiriwatana et al. (2011), Ge et al. (1999) and Hicks et a. (2007). The results show that γAA1 (γAA5 of Example 1) and the lipidated and cyclic γ-AA peptides are generally comparable or more effective as antimicrobial agents. Lipidated γAA2 did not cause resistance to the drug (lipidated γAA2; see FIG. 4B).

Structure:
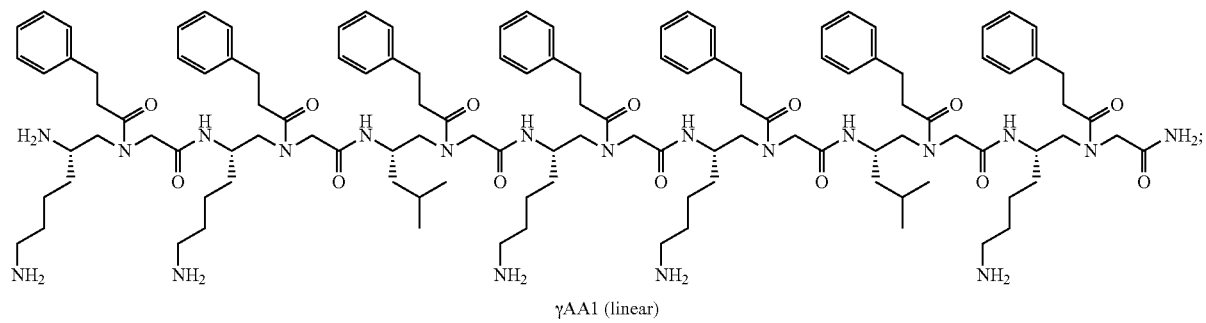
γAA1 (linear)
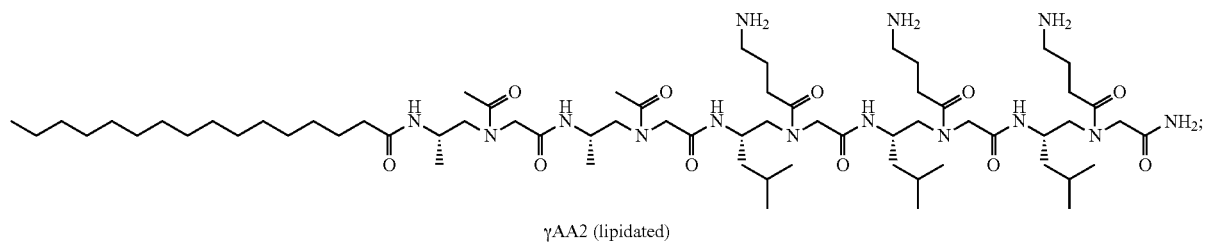
γAA2 (lipidated)
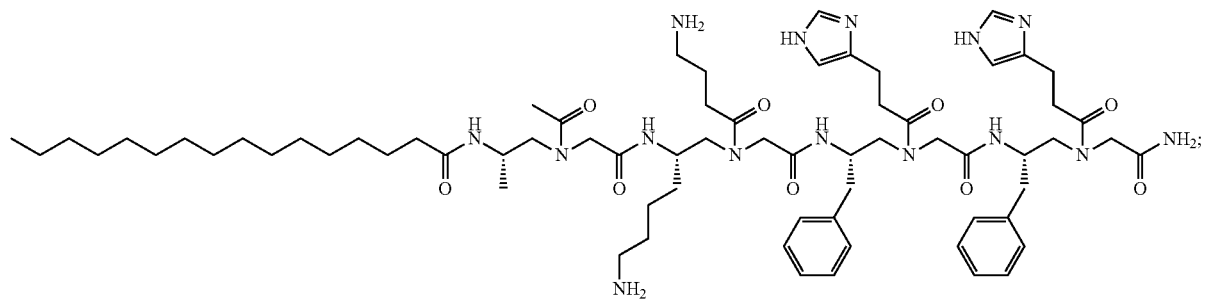
γAA3 (lipidated)
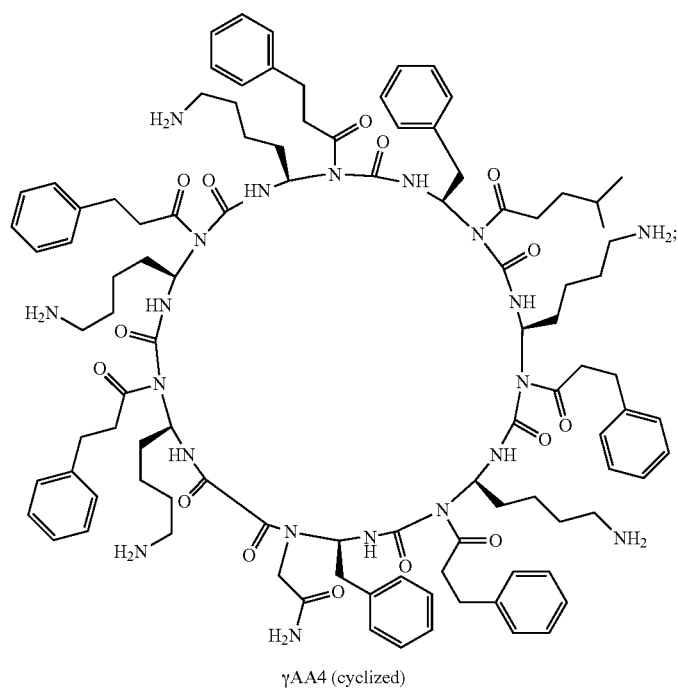
γAA4 (cyclized)

-continued
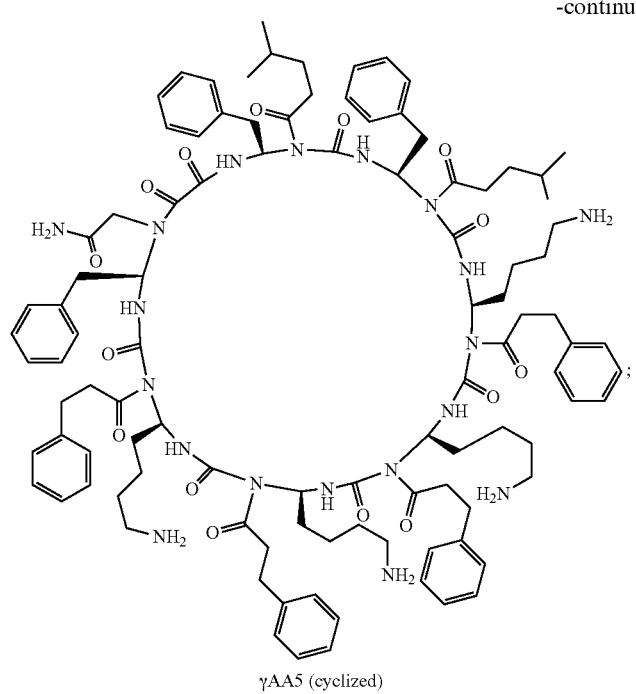
γAA5 (cyclized)
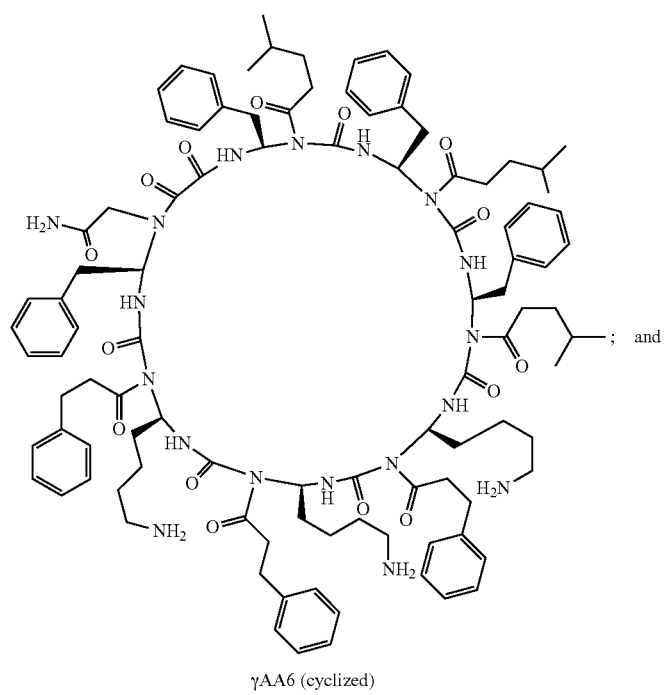
; and
γAA6 (cyclized)

-continued

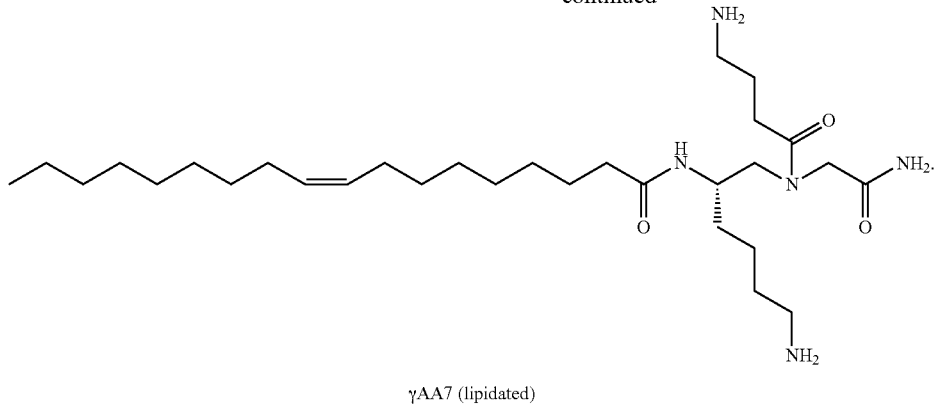

γAA7 (lipidated)

TABLE 3

| Organism | MIC (μg/ml) | | | | | | | |
|---|---|---|---|---|---|---|---|---|
| | γAA1 | γAA2 | γAA3 | γAA4 | γAA5 | γAA6 | γAA7 | Pexiganan |
| Gram-negative | | | | | | | | |
| E. coli | 2.5-5 | 2.5 | 1.6-3.1 | 3.1-6.3 | 12.5-25 | 25-50 | 2.5 | 16-32 |
| K. pneumoniae (causing pneumonia) | 5 | 5 | 12.5-25 | >100 | 8 | 10 | 50 | 8-16 |
| P. aeruginosa | 25-50 | 25-50 | 3-6 | 6-12 | 8 | 10 | 2.5 | 6-12 |
| Gram-Positive | | | | | | | | |
| B. subtilis | 2 | 2.5 | 1.6-3.1 | 2 | 1 | 2 | 2 | 3.9 |
| S. epidermidis (multi-drug resistant) | 3.1-6.3 | 4 | 1.6-3.1 | 2 | 2 | 2 | 1 | 8-16 |
| E. faecalis (vancomycin-resistant) | 3.1-6.3 | 5 | 1.6-3.1 | 12.5-25 | 5 | 5 | 2.5 | 16-32 |
| S. aureus (methicillin-resistant) | 5 | 4 | 1.6-3.1 | 3.1-6.3 | 1 | 3 | 5 | 16-32 |
| MRSA USA100 (leading hospital-associated strain, unresponsive to almost all antibiotics) | 5 | 10 | — | — | — | — | — | — |
| B. anthracis (lethal bioweapon) | 5 | 5 | — | — | — | — | — | — |
| Fungi | | | | | | | | |
| C. albicans | 5-10 | 5 | 1.6-3.1 | 3-6 | 2 | 4 | 1.5 | 124 |
| Hemolysis ($H_{50}$) | 300 | >500 | 150 | >500 | 100 | 300 | >500 | >500 |

Example 3—The Design and Synthesis of Cyclic γ-AApeptides

The design of the cyclic antimicrobial γ-AApeptides of the current invention is based on the linear antimicrobial γ-AApeptides (FIG. 7) (Niu, Padhee et al., 2011; Padhee et al., 2011). Potent antimicrobial activity can be achieved by joining amphiphilic building blocks together to form a globally amphipathic conformation upon interaction with bacterial membranes. The activity and selectivity can be fine-tuned by varying the ratio of cationic/hydrophobic groups.

1. Synthesis and Characterization of γ-AApeptides Building Blocks

To achieve a global distribution of cationic and hydrophobic groups along the backbone, we prepared amphiphilic building blocks with a cationic group and a hydrophobic group on either side (FIG. 7A). By joining these building blocks together and cyclizing the resulting oligomer (FIG. 7B), a global amphiphilicity is achieved upon binding to bacterial membranes (Niu, Padhee et al., 2011). The amphiphilic building block 2 was prepared according to the previously published procedure (Niu, Padhee et al., 2011), in which the amino acid is lysine, and the phenyl-ended side chain is appended to the amine. The structures of building blocks 1, 2, 3, and 4 are shown below.

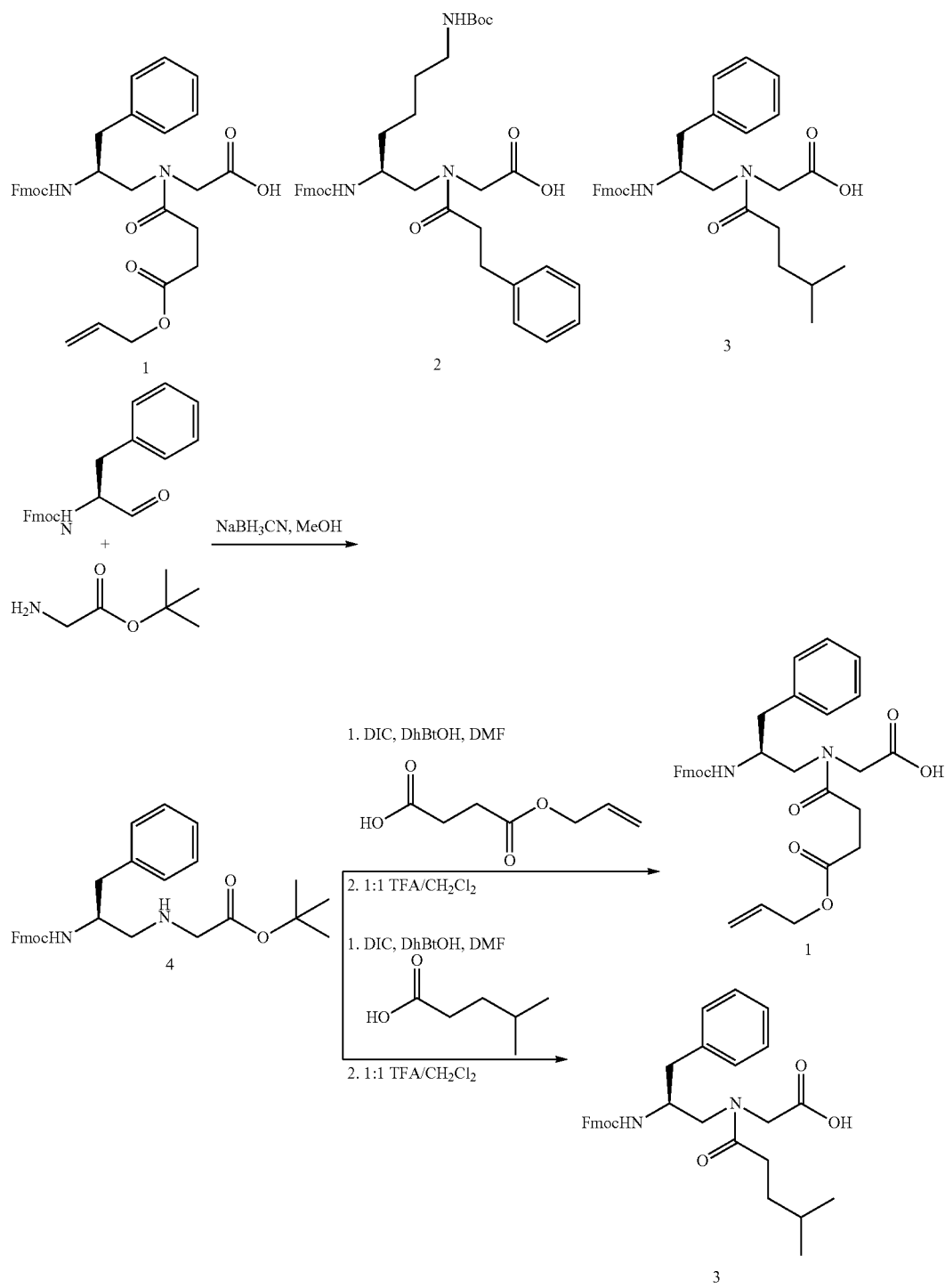

The γ-AApeptide building blocks (shown above) were synthesized following the previously reported procedure (Niu, Hu et al., 2011; Niu, Jones et al. 2011; Niu, Padhee et al., 2011). The characterization of building block 2 has been reported (Niu, Padhee et al., 2011). The synthesis of building block 1 and 3 is also shown above. Given that an introduction of a hydrophobic building block can tune the overall amphiphilicity of γ-AApeptides and improve their antimicrobial activity (Niu, Padhee et al., 2011), we also prepared building block 3 based on the reported procedure. To facilitate the on-resin cyclization of γ-AApeptide, a special γ-AApeptide building block 1 was designed. While the synthesis was carried out similarly to the previously reported procedure (Niu, Padhee et al., 2011), the mono-allyl succinate was employed to modify the amine.

Block 1. Yield 60% (two steps from 4). $^1$H NMR (DMSO-d6, 400 MHz) δ (two rotamers) 7.88 (d, 2H), 7.62-7.57 (m, 2H), 7.42-7.29 (m, 4H), 7.28-7.15 (m, 5H), 5.93-5.83 (m, 1H), 5.31-5.25 (m, 1H), 5.19-5.15 (m, 1H), 4.52-4.49 (m, 2H), 4.21-4.03 (m, 4H), 3.88 (d, 2H), 3.63-3.35 (m, 2H), 3.10-2.47 (m, 6H). $^{13}$C NMR (DMSO-d6, 100 MHz) δ 171.8, 171.7, 171.2, 171.0, 170.6, 155.6, 155.6, 143.8, 143.7, 143.7, 143.7, 140.6, 140.6, 138.7, 138.6, 132.6, 132.6, 129.0, 128.0, 127.9, 127.5, 126.9, 126.0, 125.8, 125.0, 125.0, 120.0, 117.4, 117.4, 65.3, 64.2, 64.2, 51.7, 51.4, 46.6, 46.5, 37.3, 28.9, 28.8, 27.4, 27.1. HR-ESI: [M+H]$^+$ cacl: 571.2439. found: 571.2410.

Block 3. Yield 60%. $^1$H NMR (DMSO-d6, 400 MHz) δ (two rotamers) 7.83 (d, J=7.6 Hz, 2H), 7.58-7.53 (m, 2H), 7.36-7.26 (m, 5H), 7.24-7.09 (m, 5H), 4.13-4.06 (m, 3H), 3.96-3.74 (m, 4H), 3.51-3.46 (m, 1H), 3.40-3.32 (m, 1H), 3.38-3.11 (m, 1H), 2.78-2.72 (m, 1H), 2.67-2.56 (m, 1H), 2.32-2.06 (m, 2H), 1.47-1.36 (m, 1H), 1.33-1.24 (m, 2H), 0.80-0.71 (m, 6H). $^{13}$C NMR (DMSO-d6, 100 MHz) δ 173.7, 156.1, 144.2, 141.1, 139.5, 139.1, 129.53, 129.46, 128.4, 128.0, 127.4, 126.5, 126.3, 125.7, 125.6, 125.5, 120.5, 120.5, 65.8, 65.8, 51.5, 51.0, 47.0, 38.3, 34.3, 34.1, 30.9, 30.9, 27.6, 27.5, 22.8, 22.7. HR-ESI: [M+H]$^+$ cacl: 529.2697. found: 529.2700.

Block 4. Yield 82%. $^1$H NMR (CDCl3, 400 MHz) δ 7.72 (d, J=8 Hz, 2H), 7.49-7.45 (m, 2H), 7.38-7.34 (m, 2H), 7.26-7.14 (m, 7H), 6.18-6.14 (m, 1H), 4.26-4.16 (m, 3H), 4.09-4.06 (m, 1H), 3.78-3.68 (m, 2H), 3.42-3.37 (m, 1H), 3.17-3.15 (m, 1H), 2.99-2.94 (m, 1H), 2.86-2.81 (m, 1H), 1.39 (s, 9H). $^{13}$C NMR (CDCl3, 100 MHz) δ 165.2, 165.1, 162.1, 161.7, 156.9, 156.8, 143.9, 143.6, 141.2, 141.1, 136.0, 129.0, 128.8, 127.7, 127.6, 127.1, 125.2, 119.8, 84.8, 67.3, 50.6, 49.8, 47.8, 46.8, 38.6, 36.9, 36.8, 27.8, 27.7. HR-ESI: [M+H]$^+$ cacl: 487.2591. found: 487.2565.

Figure 6A:
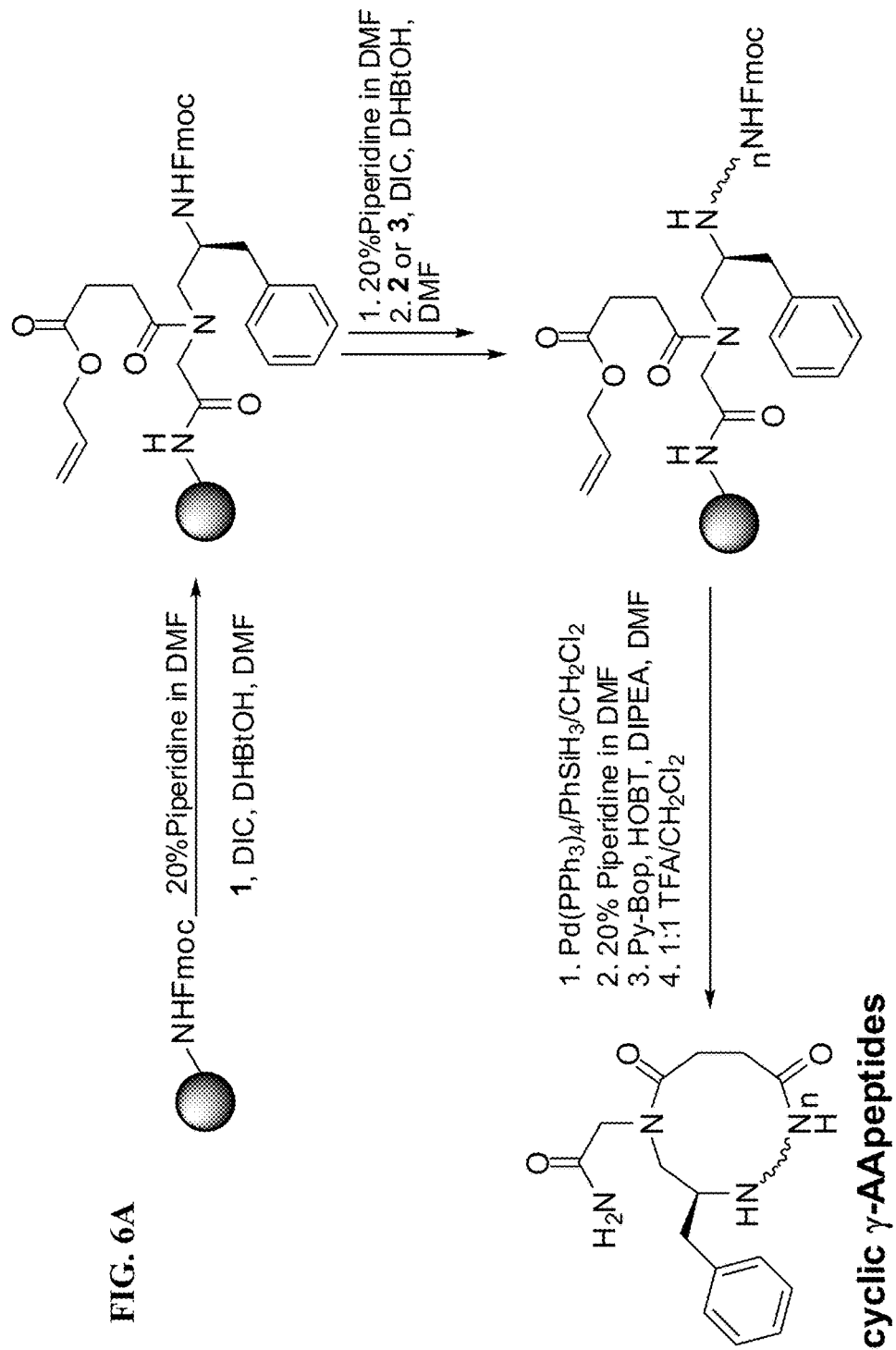
FIGS. 6A-6C.

2. Solid Phase Synthesis, Purification and Characterization of Cyclic γ-AApeptides Cyclic γ-AApeptides were prepared on a Rink amide resin in peptide synthesis vessels, on a Burrell Wrist-Action shaker, following the standard Fmoc chemistry protocol of solid phase peptide synthesis. Synthesized γ-AApeptide building blocks were used (FIG. 6A). Each coupling cycle included an Fmoc deprotection using 20% piperidine in DMF, and 8 h coupling of 1.5 equiv of γ-AApeptide building blocks in the presence of 4 equiv of DIC (diisopropylcarbodiimide)/DhbtOH (3-4-Dihydro-3-hydroxy-4-oxo-1-2-3-benzotriazine) in DMF. The cyclization was achieved on resin via the γ-AApeptide building block 1. Block 1 was first attached to the solid support, followed by standard Fmoc solid phase synthesis. After desired sequences were assembled, the allyl group was removed by treatment of Pd(PPh$_3$)$_4$ (0.2 equiv)/PhSiH$_3$ (10 equiv)/CH$_2$Cl$_2$ for 2 h (repeated two times). The deprotection of the Fmoc group was then carried out on the N-terminus. The intramolecular cyclization was accomplished using PyBop/HOBt/DIEA/DMF. Next, the resin was transferred into 4 mL vials and cyclic γ-AApeptides were cleaved from solid support in 50:48:2 TFA/CH2Cl2/triisopropylsilane overnight. Then solvent was evaporated and the residues were analyzed and purified on an analytical (1 mL/min) and a preparative (20 ml/min) Waters HPLC system, respectively, using 5% to 100% linear gradient of solvent B (0.1% TFA in acetonitrile) in A (0.1% TFA in water) over 40 min, followed by 100% solvent B over 10 min. The HPLC traces were detected at 215 nm. The desired fractions were eluted as single peaks at >95% purity with yields of 6-10% (based on loading of the resin, see FIG. 6B for sequences). They were collected and lyophilized. The molecular weights of cyclic γ-AApeptides (Table 4) were obtained on a Bruker AutoFlex MALDI-TOF mass spectrometer using ca-cyano-4-hydroxy-cinnamic acid.

TABLE 4

MALDI analysis of cyclic γ-AApeptides

| Cyclic γ-AApeptides | Yield (based on loading of the resin) | Molecular weight (actual) | Molecular weight (found) |
| --- | --- | --- | --- |
| HW-B-3 | 10.5% | 1501.2 | 1053.1 (M + H$^+$) |
| HW-B-4 | 8.6% | 1805.1 | 1806.6 (M + H$^+$) |
| HW-B-5 | 6.2% | 2108.3 | 2109.6 (M + H$^+$) |
| HW-B-11 | 6.8% | 2093.3 | 2147.6 (M + 3NH4$^+$) |
| HW-B-12 | 6.5% | 2078.3 | 2079.9 (M + H$^+$) |
| HW-B-13 | 6.0% | 2078.3 | 2079.0 (M + H$^+$) |
| HW-B-14 | 6.4% | 2063.3 | 2117.3 (M + 3NH4$^+$) |

3. Antimicrobial Assays

The microbial organisms used were *B. subtilis* (BR151), multi-drug resistant *S. epidermidis* (RP62A), *C. albicans* (ATCC 10231), vancomycin-resistant *E. faecalis* (ATCC 700802), methicillin-resistant *S. aureus* (ATCC 33592), and *K. pneumoniae* (ATCC 13383), multi-drug resistant *P. aeruginosa* ATCC 27853. The minimum inhibitory concentration (MIC) is the lowest concentration that completely inhibits the growth of bacteria in 24 h. The highest concentration tested for antimicrobial activity was 50 μg/mL. The antimicrobial activities of the cyclic γ-AApeptides were determined in a sterile 96-well plates by the broth microdilution method. Bacterial cells 4 and fungi 5 were grown overnight at 37° C. in 5 mL medium, after which a bacterial suspension (approximately 106 CFU/mL) or fungal suspension of *Candida albicans* (ATCC 10231) (approximately 103 CFU/mL) in Luria broth or trypticase soy was prepared. Aliquots of 50 μL bacterial or fungal suspension were added to 50 μL of medium containing the cyclic γ-AApeptides for a total volume of 100 μL in each well. The cyclic γ-AApeptides were prepared in PBS buffer in 2-fold serial dilutions, with the final concentration range of 0.5 to 50 μg/mL. Plates were then incubated at 37° C. for 24 h (for bacteria) or 48 h (for *Candida albicans* (ATCC 10231)). The lowest concentration at which complete inhibition of bacterial growth (determined by a lack of turbidity) is observed throughout the incubation time is defined as the minimum inhibitory concentration (MIC). The experiments were carried out independently three times in duplicate.

Cyclized γ-AApeptides (HW-B-3, -4, -5) comprising four, five, and six amphiphilic building blocks were prepared as an initial attempt, and tested for their antimicrobial activities against a series of Gram-positive and Gram-negative bacteria and fungi, many of which are multi-drug resistant and clinically relevant strains (Table 5). The oligomers' hemolytic activities toward human red blood cells were also measured, as an indication of their selectivity. For comparison, Pexiganan, a phase III antimicrobial peptide drug candidate (Chongsiriwatana et al., 2008; Chongsiriwatana et al., 2011; Ge et al., 1999; Hicks et al., 2007), as well as γ5, the most potent linear γ-AApeptide (Niu, Padhee et al., 2011), were both used as controls. Similar to a linear γ-AApeptide, which appeared to be more potent with a longer sequence (Niu, Padhee et al., 2011), the cyclic γ-AApeptide with an increasing ring size (from HW-B-3 to HW-B-5) tended to augment the antimicrobial activities (Table 5). The most potent cyclic γ-AApeptide, HW-B-5, has a similar activity to the well-known Pexiganan, though it is still inferior to γ5. It is notable that the hemolytic activity of HW-B-5 is much less than Pexiganan and γ5, implying the potential to improve its anti-bacterial activities through the introduction of hydrophobic building blocks (Niu, Padhee et al., 2011).

Figure 6B:
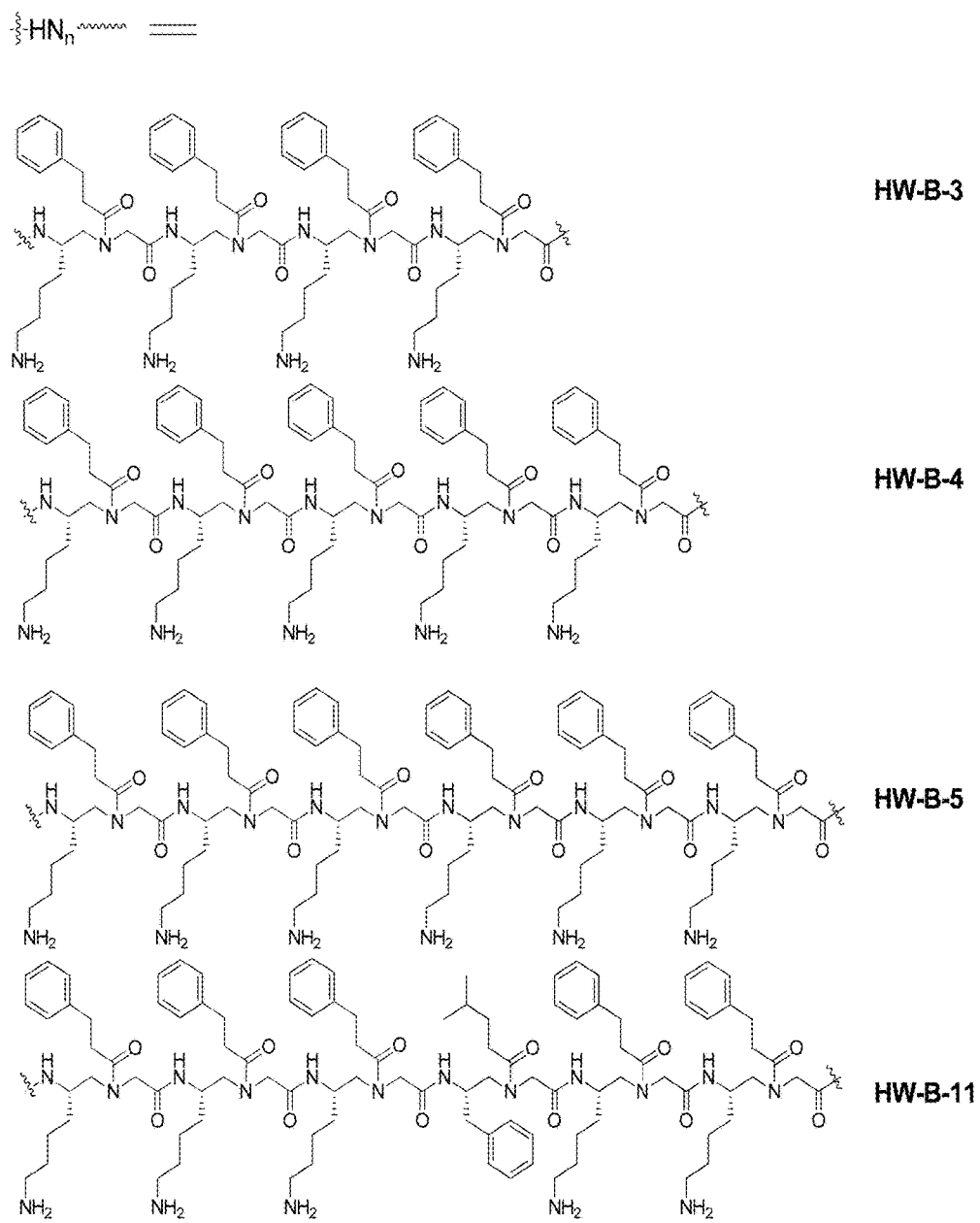
Figure 6B:
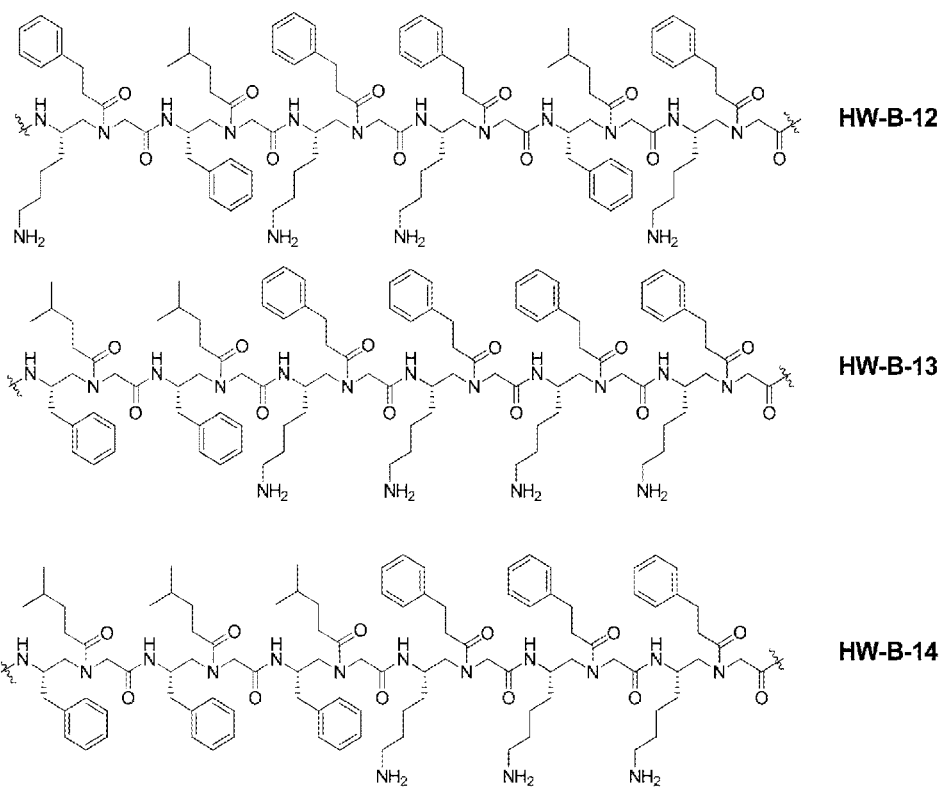
Figure 6C:
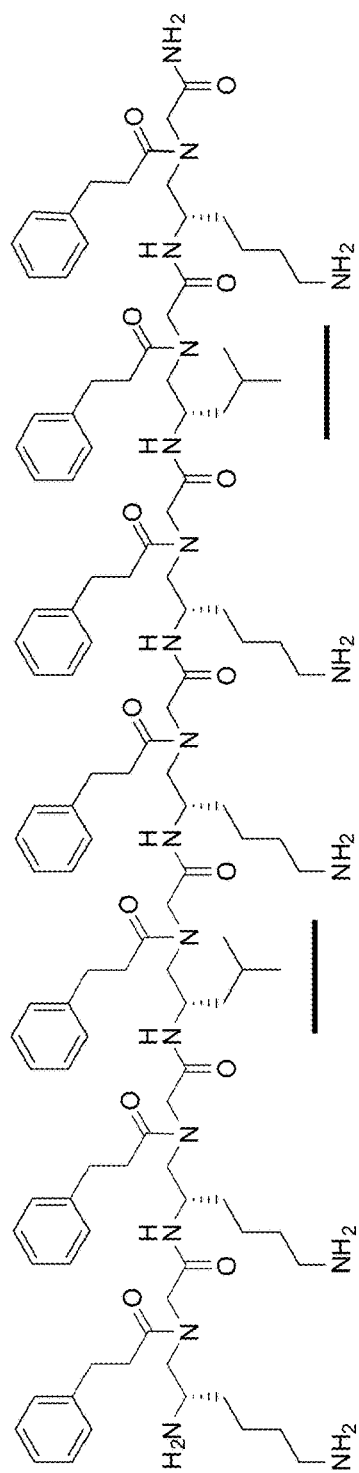
Figure 9A:
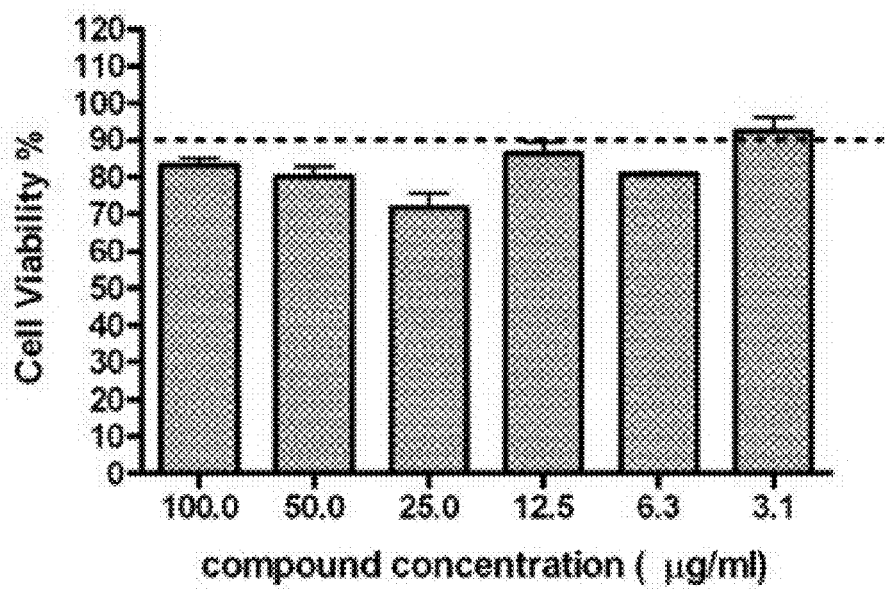
FIGS. 9A-9G. MTT cytotoxicity assay of N2a/APP cells treated with different concentrations of cyclic γ-Aapeptides (HW-B-3 treatment, FIG. 9A; HW-B-4 treatment, FIG. 9B; HW-B-5 treatment, FIG. 9C; HW-B-11 treatment, FIG. 9D; HW-B-12 treatment, FIG. 9E; HW-B-13 treatment, FIG. 9F; HW-B-14 treatment, FIG. 9G).
Figure 9B:
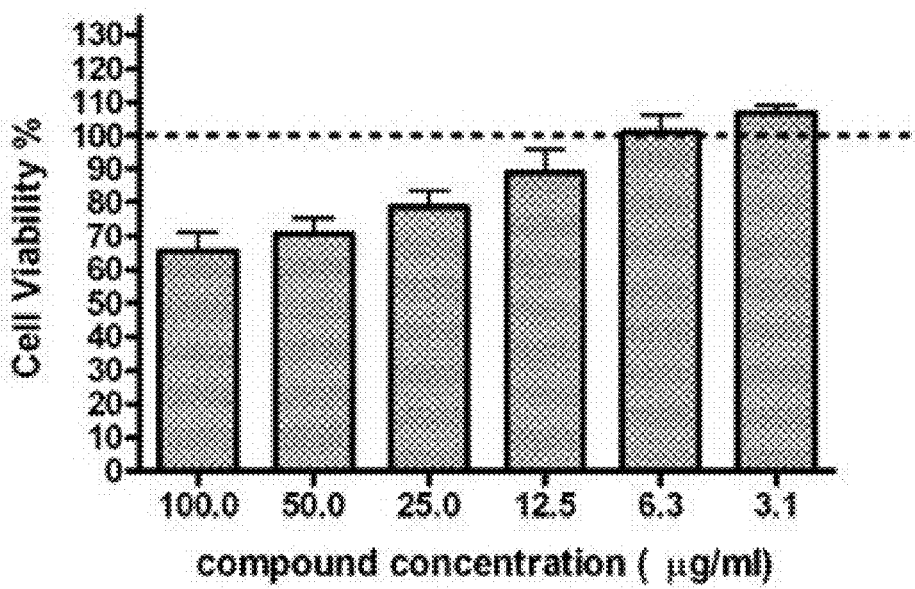
Figure 9C:
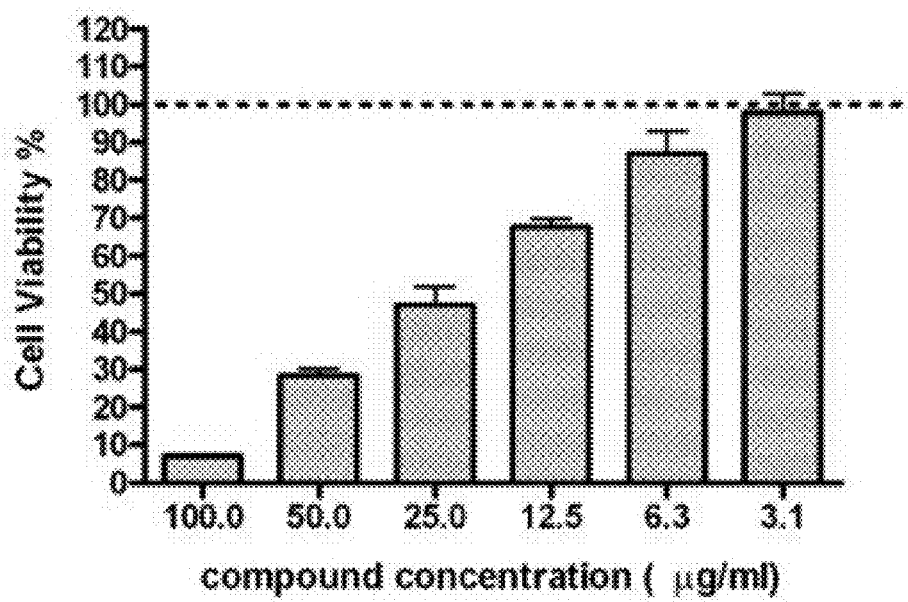
Figure 9D:
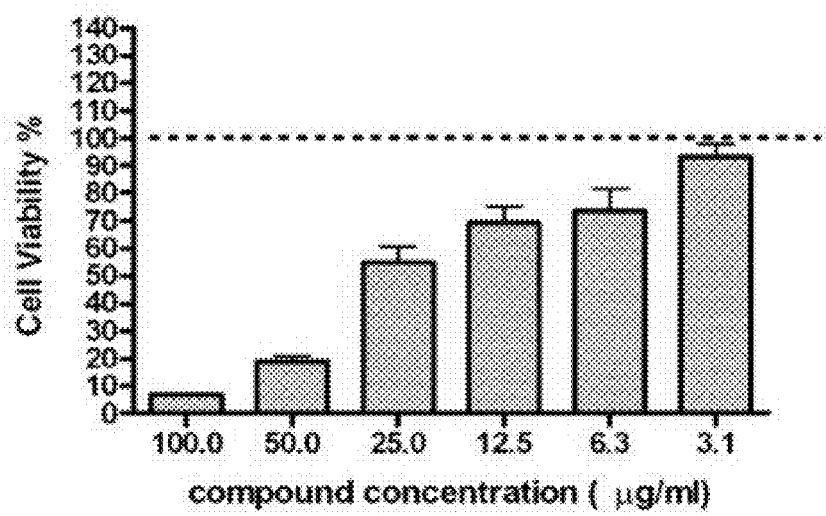
Figure 9E:
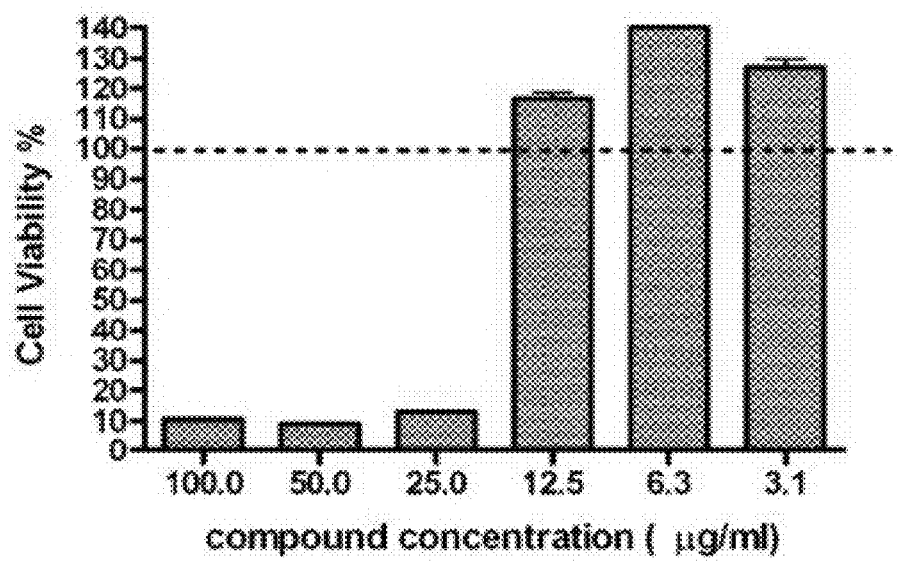
Figure 9F:
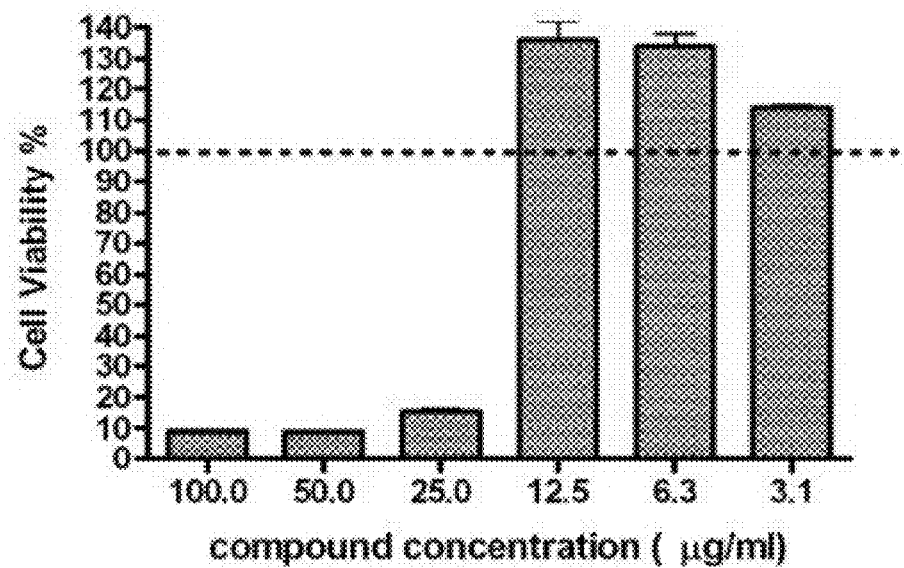
Figure 9G:
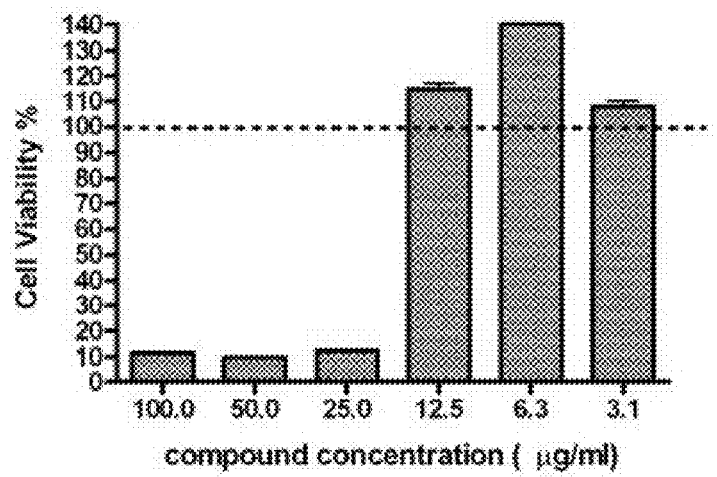

Given that linear γ5 bears hydrophobic building blocks, and thus exhibited much more potent antimicrobial activities than other linear γ-AApeptides completely made from amphiphilic building blocks (Niu, Padhee et al., 2011), similar configurations for cyclic γ-AApeptides were attempted. HW-B-11, -12, and -13 were thereby prepared to incorporate the same number of building blocks as HW-B-5, but have one or two amphiphilic building blocks replaced by hydrophobic ones (FIG. 6B). As a result, HW-B-11, with the change of only one building block, showed enhanced antimicrobial activities, especially against Gram-positive bacteria, which are comparable to linear γ5, and better than Pexiganan (Table 5). In spite of its weaker activity towards Gram-negative strain *K. pneumoniae*, HW-B-11 has a stronger inhibition of fungus *C. albicans* than both Pexiganan and linear γ5, with a significant minimum inhibitory concentration (MIC) value of 5 mg/ml. In addition, HW-B-11 still possessed a low hemolytic activity, thereby making it a promising antimicrobial agent with comparable or even better selectivity than Pexiganan and linear γ5. Further, HW-B-12 was developed to incorporate two hydrophobic building blocks, which are separated by two hydrophilic building blocks, in a way similar to the design of linear γ5. Its antimicrobial activities were not improved, or maybe weaker compared to HW-B-11. To assess whether the decrease in activity is due to the incorporation of more hydrophobic building blocks or is caused by their relative positions in the ring, HW-B-13 was synthesized by placing two hydrophobic building blocks adjacent to each other (FIG. 6B). HW-B-13 exhibited even better activity than HW-B-11, Pexiganan, and linear γ5 to arrest the growth of both Gram-positive and Gram-negative bacteria pathogens, as well as in fungus (Table 5). HWB-13 is a potent antimicrobial peptidomimetic with broad-spectrum activity, especially toward two of the most clinically relevant strains, *S. aureus* (MRSA) and *P. aeruginosa* (PA), with a MIC value of 1 mg/mL and 8 mg/mL, respectively: which is at least 5-fold more potent than the linear γ5. Though HW-B-13 appears to be more hemolytic, its overall selectivity in several important pathogens is still improved relative to linear γ5 and Pexiganan.

To further investigate the effect of hydrophobicity and to tune the activity, HW-B-14 (FIG. 6B) with three hydrophobic building blocks was developed, which, however, resulted in a slightly decreased antimicrobial activity and hemolytic activity (Table 5) in comparison to HW-B-13. Nevertheless, the activity and selectivity of HW-B-14 are still generally comparable, or superior to linear γ5, against several strains including MRSA and PA.

TABLE 5

The antimicrobial and hemolytic activities of oligomers. The MICs of Pexiganan and Linear γ5 (described above) are shown for comparison.

| Organism | HW-B-3 | BW-B-4 | HW-B-5 | HW-B-11 | HW-B-12 | HW-B-13[a] | HW-B-14[a] | Pexiganan | Linear γ5 |
|---|---|---|---|---|---|---|---|---|---|
| Gram-positive | | | | | | | | | |
| *B. subtilis* | 25-50 | 10 | 5 | 2 | 5 | 1 | 2 | 4 | 2 |
| *S. epidermidis* (MRSE) | >50 | 10 | 8 | 2 | 5 | 2 | 2 | 8 | 5 |
| *E. faecalis* (VREF) | >50 | 20 | 20 | 15 | 8 | 5 | 5 | 32 | 5 |
| *S. aureus* (MRSA) | >50 | >50 | 25-50 | 5 | 6 | 1 | 3 | 16 | 5 |
| Gram-negative | | | | | | | | | |
| *K. pneumoniae* | >50 | >50 | >50 | 20 | 5 | 8 | 10 | 8 | 5 |
| *P. aeruginosa* | >50 | 20 | 18 | 10 | >50 | 8 | 10 | 8-16 | >50 |
| Fungus | | | | | | | | | |
| *C. albicans* | >50 | >50 | >50 | 5 | 5 | 2 | 4 | 124 | 8 |
| Hemolysis (H10/H50) | >500/>500 | >500/>500 | >500/>500 | 200/>500 | 150/450 | 40/100 | 45/300 | 181/495 | 75/300 |

[a]Sequences showing the most broad-spectrum antimicrobial activity.

Based on these results, it appears that the inclusion of two neighboring hydrophobic building blocks brings in the optimal antimicrobial activity. The structure-activity studies of HW-B-5, -11, -13, and -14 suggest that a higher percentage of hydrophobic groups in γ-AApeptides leads to greater antimicrobial activity. It is well accepted that more lipophilicity would lead to increased hemolytic activity (Chongsiriwatana et al., 2008; Mowery et al., 2009). While the result of our structure-activity studies generally supports this rule, the slightly decreased hemolytic activity demonstrated by HW-B-14, which has one more hydrophobic building block than HW-B-13, is quite unexpected. It suggests that besides the absolute hydrophobicity of functional groups, the overall conformations of molecules may also affect their hemolytic activity.

In this case, multiple neighboring hydrophobic building blocks in HW-B-14 promote hydrophobic interactions among their side chains, which limit their efficient contact with red blood cells. Finally, the distinct activities between HW-B-12 and HW-B-13 suggest the importance of position for hydrophobic building blocks. A preliminary computer modeling of HW-B-13 reveals that the cyclic γ-AApeptide naturally adopts a globally amphipathic conformation, with cationic side groups clustered at the bottom left face of the ring, and the majority of hydrophobic groups at the top face of the ring (FIG. 8). Such a constrained structure with predefined amphiphilicity may favor the binding and disruption events within bacteria membranes. To the contrary, the amphiphilic topology of HW-B-12 may be scrambled by the separated hydrophobic building blocks. Though linear γ-AApeptides with scrambled amphipathicity can still be induced by a membrane to adopt a global amphiphilicity (Niu, Padhee et al., 2011), the rigid structure of cyclic γ-AApeptides compromises their conformational flexibility.

4. MTT Cytotoxicity Assay

N2a APP cells were used to access the cytotoxicity of cyclic γ-AApeptides toward mammalian cells (FIG. 9). Typically, stock concentration of a particular cyclic γ-AApeptide (1 mg/ml) was diluted in media to make different concentrations in 96-well plates, and then incubated at 37° C. Following that, N2a APP cells were seeded to $1\times10^4$ cells/well in 100 µl media in another 96-well plate. After incubation for 12 hours, 100 µl of different concentrations of cyclic γ-AApeptides were added and the plate was incubated for another 36 hours. The media in the 96-well plate was removed and washed with fresh media once, and 110 µl MTT reagent was added. The mixture was incubated for another 4 hours, after which 100 µl of pre-warmed solubilization solution was added. The plate was then incubated at 37° C. for 12 h, and the absorbance at 550 nm was read. Percentage of cell viability was calculated based on the following equation:

$$\text{cell viability \%} = (A/A_{control}) \times 100$$

The results are quite consistent with hemolytic results, with more hemolytic sequences being more toxic. However, the $EC_{50}$s (the effective concentration to cause half of the cells' death) are all above 12.5 mg/mL, indicating cyclic γ-AApeptides are very selective toward bacteria over mammalian cells. For instance, HW-B-13 is at least 12.5-fold more selective toward MRSA.

5. Lipid Depolarization

To understand the antimicrobial mechanisms of cyclic γ-AApeptides, the most active ones, HW-B-11, -13, and -14, were used to investigate their effects in cytoplasmic membrane disruption through the depolarization of the *S. aureus* membrane (FIG. 10) (Choi et al, 2009). The lipid depolarization of the bacterial cell membrane was conducted using the membrane potential sensitive dye 3, 5'-dipropylthiacarbocyanine iodide (DiSC3-5) that distributes between the cells and the medium depending on the membrane potential gradient. *S. aureus* (ATCC 33592) cells were grown in Luria broth and Trypticase soy broth medium respectively to a mid-logarithmic phase (OD600=0.5-0.6). The bacterial cells were then collected by centrifugation at 3000 rpm for 10 min and then washed once with buffer (5 mM HEPES and 5 mM glucose, pH 7.2). The cells were re-suspended to OD600=0.05 with 100 mM KCl, 2 µM DiSC3-5.5 mM HEPES and 5 mM glucose and were incubated for 30 min at 37° C. for maximal dye uptake and fluorescence self-quenching. This bacterial suspension (90 µL) and 10 µL of compound stock solutions or control drug solution were added to white flat-bottomed polypropylene 96-well plates (Costar) and incubated at 37° C. for 30 min. The fluorescence reading was monitored using the microplate reader (Biotek) at an excitation wavelength of 622 nm and an emission wavelength of 670 nm); the fluorescence increased due to the disruption of cytoplasmic membrane. Valinomycin (final concentration 250 µg/mL) was used as a positive control, and the blank with only cells and dye was used as the background.

Figure 10:
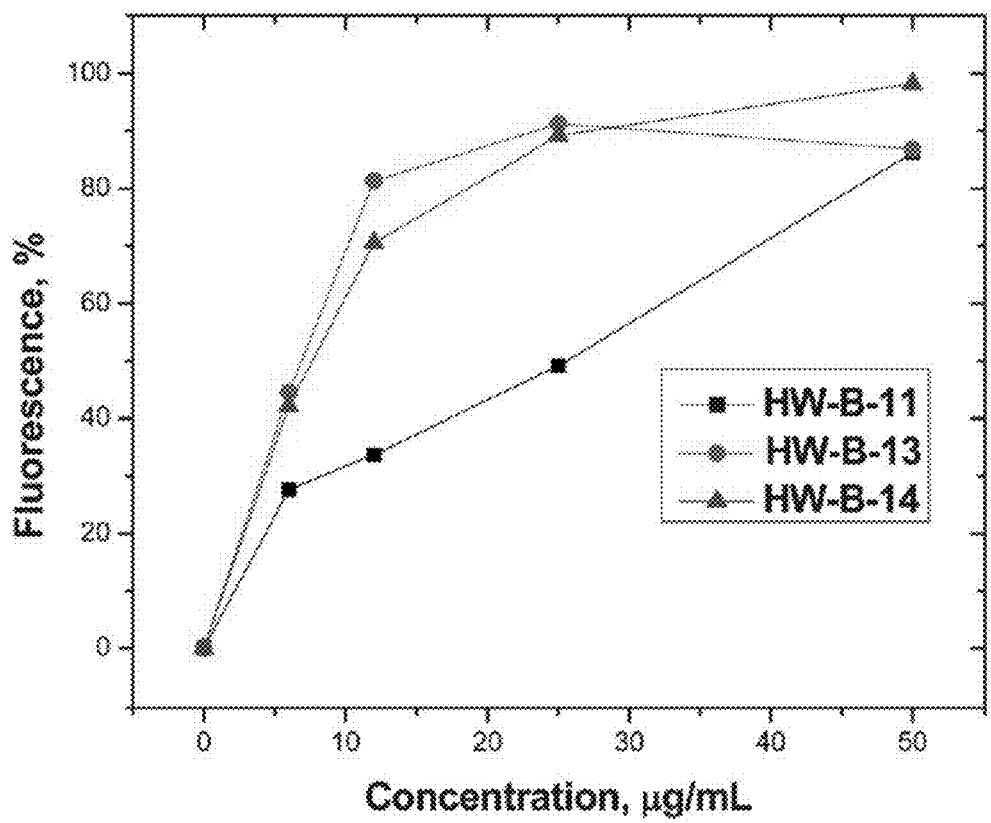
FIG. 10. Depolarization of the cytoplasmic membrane of *S. aureus* by cyclic γ-AApeptides.

The distribution of DiSC3-5 between the medium and the cell interior reflects the membrane potential (Choi et al, 2009). The loss of membrane potential as a result of membrane permeation/disruption leads to a dramatic increase in fluorescent intensity (Choi et al, 2009). Although the oligomer concentration needed for depolarization is actually higher than the oligomers' MIC values, generally more active antimicrobial oligomers with lower MIC values tended to reach a high percentage of depolarization at a lower concentration. Such a trend was clearly demonstrated by HW-B-11, -13 and -14, which supports the membrane disruption mechanism of cyclic γ-AApeptides (FIG. 10).

6. Fluorescence Microscopy

Figure 11:
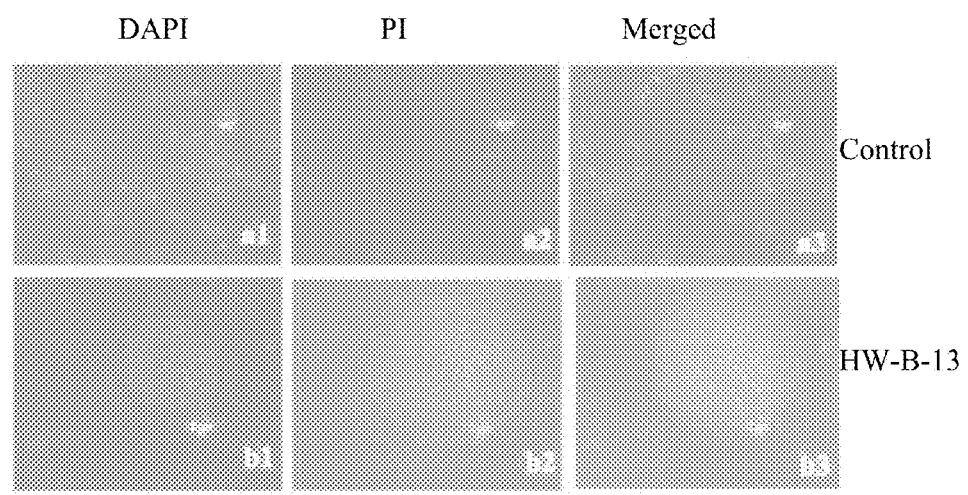
FIG. 11. Fluorescence micrographs of *B. subtilis* treated with 5 μg/ml cyclic γ-AApeptide HW-B-13 for 2 h. a1, control, no treatment, DAPI stained; a2, control, no treatment, PI stained; a3, control, no treatment, the merged view. b1, HW-B-13 treatment, DAPI stained; b2, HW-B-13 treatment, PI stained; b3, HW-B-13 treatment, the merged view. Scale bar: 2 am.

The antimicrobial mechanism of cyclic γ-AApeptides was further assessed by fluorescence microscopy, in which *B. subtilis* was treated with the most potent HW-B-13, and stained with DAPI and PI33 dyes (FIG. 11). The double staining method with DAPI (4',6-Diamidino-2-phenylindole dihydrochloride, Sigma, >98%) and PI (Propidium iodide, Sigma) as fluorophores was used to visualize and differentiate the viable from the dead *B. subtilis* cells. DAPI, as a double-stranded DNA binding dye, stains all bacterial cells irrespective of their viability, whereas Ethidium derivatives such as propidium iodide (PI) are capable of passing through only damaged cell membranes and intercalating with the nucleic acids of injured and dead cells to form a bright red fluorescent complex (Matsunaga et al., 1995). The cells were first stained with PI and then with DAPI. Bacterial cells were grown until they reached the mid-logarithmic phase and then they ($\sim 2\times 10^6$ cells) were incubated with the cyclic γ-AApeptide HW-B-13 at the concentration of 2×MIC (10 µg/mL) for 2 h. Then the cells were pelleted by centrifugation at 3000 g for 15 min in an Eppendorf microcentrifuge. The supernatant was then decanted and the cells were washed with 1×PBS several times and then incubated with PI (5 µg/mL) in the dark for 15 min at 0° C. The excess PI was removed by washing the cells with 1×PBS several times. Then the cells were incubated with DAPI (10 µg/mL in water) for 15 min in the dark at 0° C. The DAPI solution was removed and the cells were washed with 1×PBS several times. Controls without the addition of HW-B-13 were performed following exactly the same procedure for bacteria. The bacterial cells were then examined by using the Zeiss Axio Imager Z1 optical microscope with an oil-immersion objective (100×) (Niu, Padhee et al., 2011; Padhee et al., 2011; Williams et al., 1998).

Compared to little PI staining (red fluorescence) observed in the control group, *B. subtilis* incubated with HW-B-13 for 2 h displayed a strong red staining by PI, indicating the significant disruption of bacterial membranes by HW-B-13. The aggregation of dead bacterial cells after the oligomer treatment is consistent with literature reports, (Niu, Padhee et al., 2011; Chen et al., 2010), an indication of loss of membrane potential.

Example 4—The Design and Synthesis of Lipidated-γ-AApeptides

1. Synthesis of the γ-AApeptide Building Blocks for Lipidated γ-AApeptides

The γ-AApeptide building blocks used in the solid phase synthesis of lipidated γ-AApeptides were synthesized following the previously reported procedure (Niu, Hu et al., 2011; Niu, Jones et al., 2011; Niu, Padhee et al., 2011). The examples of the building blocks are shown below.

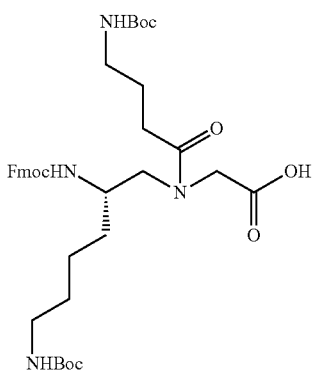

Compound B1

Compound B1. Yield 65.3% in two steps from the secondary amine. 1-3 $^1$H NMR (400 MHz, DMSO-d6) δ 7.84 (d, J=8.0 Hz, 2H), 7.64-7.61 (dd, J=4.0, 8.0 Hz, 2H), 7.37 (t, J=8.0 Hz, 2H), 7.28 (t, J=8.0 Hz, 2H), 7.14 & 6.98 (2d, J=8.0 Hz, 1H), 6.74-6.69 (m, 1H), 4.29-4.14 (m, 3H), 3.40-3.81 (m, 2H), 3.62-3.52 (m, 2H), 3.28-3.16 (m, 1H), 2.95-2.69 (m, 4H), 2.36-2.22 (m, 1H), 2.12-2.01 (m, 1H), 1.70-1.13 (m, 26H). $^{13}$C NMR (100 MHz, CD3OD) δ 174.7, 174.4, 171.5, 171.2, 157.32, 157.3, 157.1, 143.9, 143.8, 141.23, 141.20, 127.3, 126.7, 124.7, 124.6, 119.5 78.5, 78.4, 66.1, 65.9, 53.1, 51.2, 50.1, 49.9, 49.8, 39.8, 39.5, 39.3, 31.6, 31.2, 29.7, 29.5, 29.2, 27.4, 25.2, 22.9, 22.8. HR-ESI: [M+H]$^+$ cacl: 697.3807. found: 697.3796.

Compound B2

Compound B2. Yield 82.6% in two steps from the secondary amine. 1-3 $^1$H NMR (400 MHz, DMSO-d6) δ 7.83 (d, J=8.0 Hz, 2H), 7.62 (d, J=7.6 Hz, 2H), 4.28-4.14 (m, 3H), 4.03-3.63 (m, 2H), 3.42-3.33 (m, 2H), 3.22-3.21 (m, 1H), 1.98 & 1.84 (rotamers, 2s, 3H), 1.02 & 0.95 (rotamers, 2d, J=6.4 Hz, 3H). $^{13}$C NMR (100 MHz, DMSO-d6) δ 171.6, 171.4, 171.2, 170.7, 156.1, 144.3, 144.26, 141.2, 128.0, 127.5, 125.6, 125.5, 120.5, 65.7, 65.6, 56.4, 54.2, 51.5, 51.1, 49.97, 47.2, 17.17, 45.9, 21.7, 21.4, 18.8, 18.5 HR-ESI: [M+H]$^+$ cacl: 397.1758. found: 397.1760.

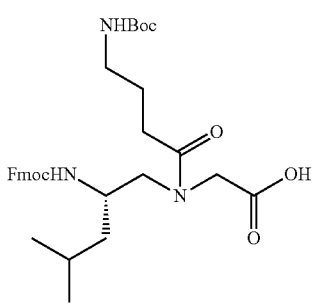

Compound B3

Compound B3. Yield 75.9% in two steps from the secondary amine. 1-3 $^1$H NMR (400 MHz, DMSO-d6) δ 7.86-7.83 (m, 2H) 7.65-7.60 (m, 2H), 7.39-7.13 (m, 2H), 7.14 & 7.00 (d&d, J=8.0 Hz, 1H), 6.75-6.72 (m, 1H), 4.31-4.22 (m, 2H), 4.17-4.12 (m, 1H), 3.97-3.77 (m, 2H), 3.72-3.64 (m, 1H), 3.46-3.18 (m, 2H), 2.91-2.84 (m, 2H), 2.39-2.24 (m, 1H), 2.16-2.02 (m, 1H), 1.57-1.50 (m, 2H), 1.38-1.26 (m, 11H), 0.86-0.77 (m, 6H). $^{13}$C NMR (100 MHz, DMSO-d6) δ 173.0, 172.7, 171.2, 156.4, 156.3, 156.0, 144.4, 144.35, 144.3, 144.2, 141.2, 141.1, 128.0, 127.44, 127.41, 125.5, 120.5, 79.6, 77.7, 65.6, 65.4, 52.9, 51.3, 50.7, 48.3, 47.32, 47.26, 41.6, 41.0, 30.2, 29.8, 25.7, 25.6, 24.7, 23.8, 23.7, 22.1, 21.9. HR-ESI: [M+H]$^+$ cacl: 582.3174. found: 582.3175.

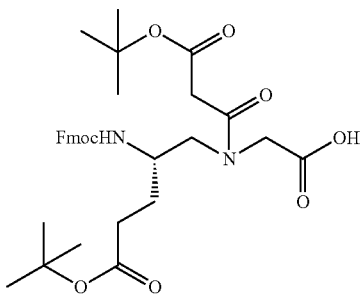

Compound B4

Compound B4. Yield 63.8% in two steps from the secondary amine. 1-3 $^1$H NMR (400 MHz, DMSO-d6) δ 7.86-7.80 (m, 4H), 7.40-7.29 (m, 4H), 4.02-3.93 (m, 2H), 3.73-3.69 (m, 1H), 3.68-3.62 (m, 1H), 3.53-3.50 (m, 1H), 3.49-3.36 (m, 1H), 3.19-3.14 (m, 1H), 3.13-3.02 (m, 1H), 2.35-2.22 (m, 2H), 1.72-1.60 (m, 2H), 1.37 & 1.36 & 1.35 (rotamers, m, 18H). $^{13}$C NMR (100 MHz, DMSO-d6) δ 172.4, 167.8, 167.3, 156.4, 156.3, 144.4, 144.2, 141.1, 128.0, 127.5, 127.47, 125.63, 125.61, 120.5, 80.7, 79.8, 65.7, 60.2, 53.0, 50.6, 50.4, 49.9, 49.4, 49.1, 47.2, 42.7, 42.4, 42.1, 42.1, 42.0, 31.9, 31.3, 28.2, 28.1, 28.0 HR-ESI: [M+H]$^+$ cacl: 611.2963. found: 611.2958.

2. Solid Phase Synthesis, Purification and Characterization of Lipidated γ-AApeptides (Niu, Hu et al., 2011; Niu, Jones et al., 2011; Niu, Padhee et al., 2011)

The lipidated γ-AApeptides (also referred to as lipo-γ-AApeptides) were prepared by attaching hydrophobic alkyl tails to cationic γ-AApeptides. The synthesis of lipidated γ-AApeptides was carried out on the solid phase (as shown below) and purified by HPLC adapted from previously reported protocols (Niu, Padhee et al., 2011; Niu, Jones et al., 2011; Niu, Hu et al., 2011).

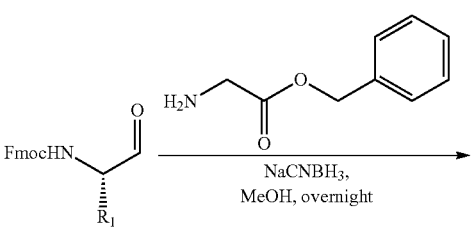

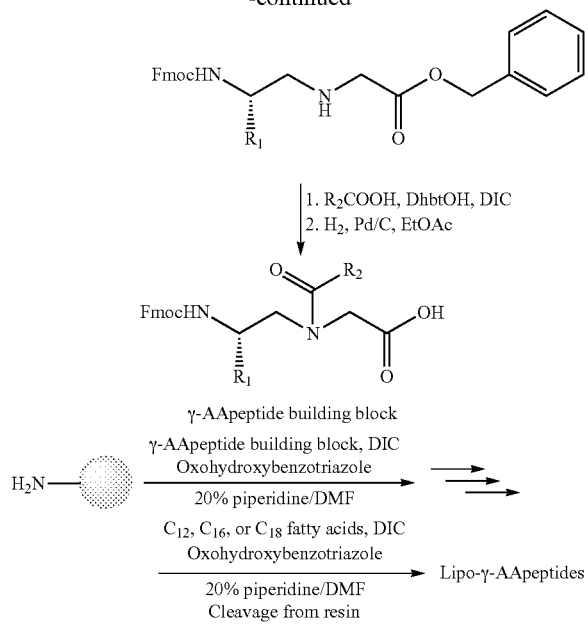

Figure 12:
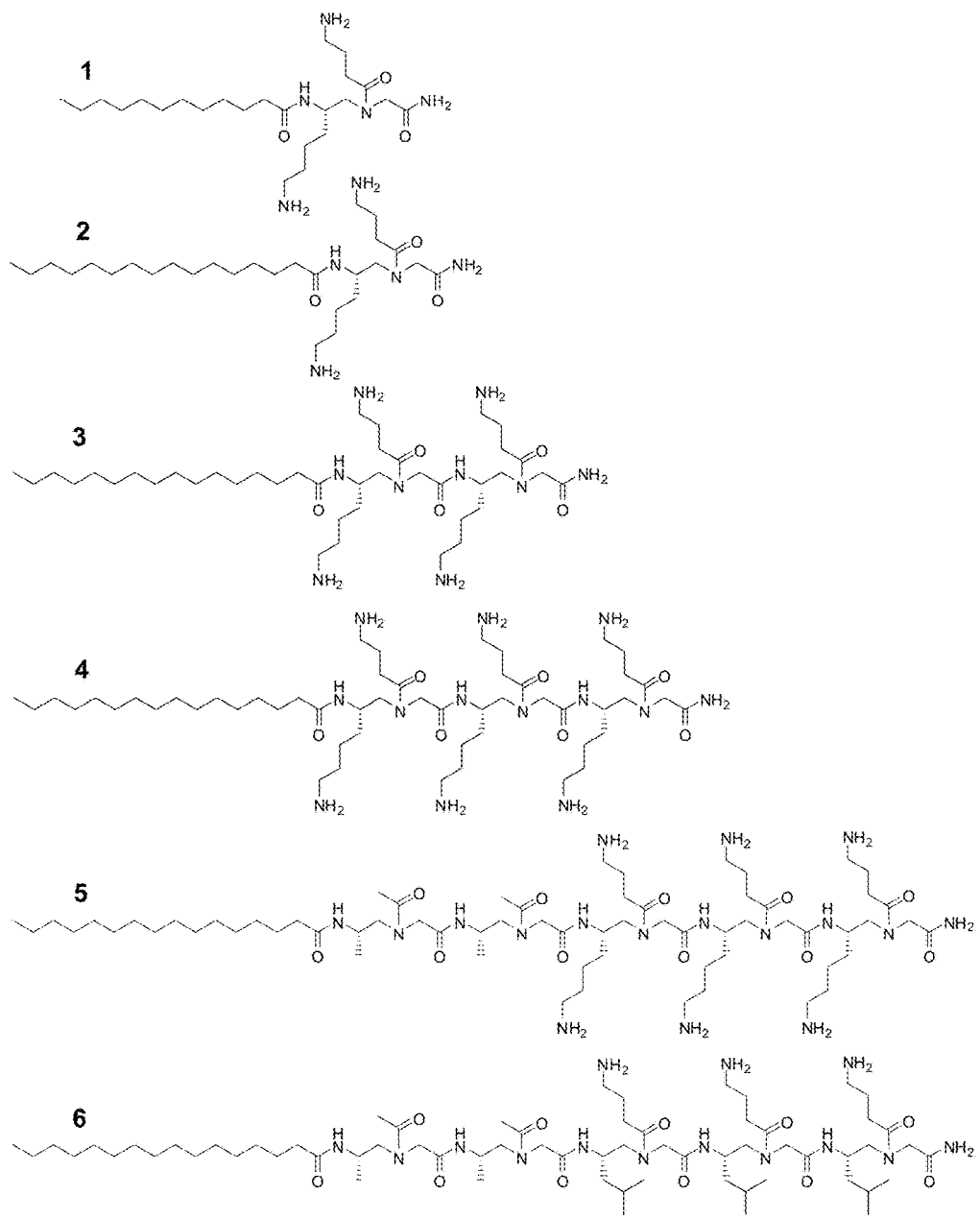
FIG. 12. γ-AApeptides used in antimicrobial assays. The first structure shows the general structure of γ-AApeptide building blocks.
Figure 12:
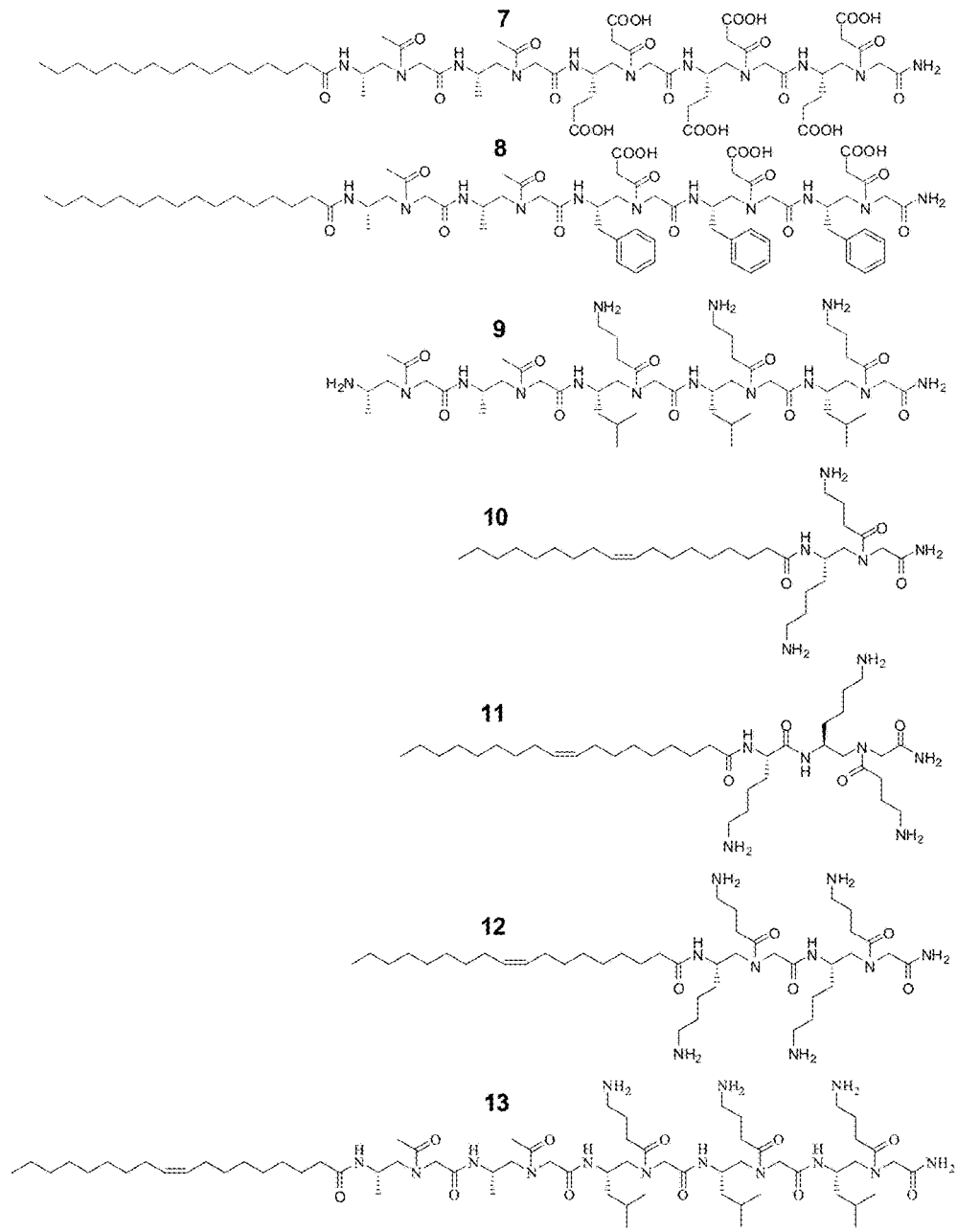

Lipidated γ-AApeptides were prepared on a Rink amide resin in peptide synthesis vessels on a Burrell Wrist-Action shaker following the standard Fmoc chemistry of solid phase peptide synthesis protocol. Each coupling cycle included an Fmoc deprotection using 20% piperidine in DMF, and 4 h coupling of 1.5 equiv of γ-AApeptide building blocks (Niu, Hu et al., 2011; Niu, Jones et al., 2011; Niu, Padhee et al., 2011) onto the resin in the presence of 2 equiv of DIC (diisopropylcarbodiimide)/DhBtOH (oxohydroxybenzotriazole) in DMF. The lipidation was accomplished by reacting lauric acid, palmitic acid or oleic acid with N-terminus using DIC/DhBtOH as activation agents on the solid phase. After the desired sequences were assembled, they were transferred into a 4 ml vial and cleaved from solid support in 50:45:5 TFA/CH$_2$Cl$_2$/triisopropylsilane overnight (FIG. 12). Then the solvent was evaporated and the residues were analyzed and purified on a Waters HPLC installed with both an analytical module (1 ml/min) and a preparative module (20 ml/min). Both modules had the same methods which were using 5% to 100% linear gradient of solvent B (0.1% TFA in acetonitrile) in A (0.1% TFA in water) over 40 min, followed by 100% solvent B over 10 min. The desired fractions were generally over 70% in crude (determined by HPLC) and eluted as single peaks at >95% purity. They were collected and lyophilized. The molecular weights of lipidated γ-AApeptides were obtained on a Bruker AutoFlex MALDI-TOF mass spectrometer using α-cyano-4-hydroxycinnamic acid as the matrix (shown in Table 6).

TABLE 6

MALDI analysis of lipidated γ-AApeptides

| Lipo-γ-AApeptide | Formula | Mass calculated | Mass found |
|---|---|---|---|
| 1 | $C_{24}H_{49}N_5O_3$ | 455.38 | 458.20 (M + 3H)$^+$ |
| 2 | $C_{28}H_{57}N_5O_3$ | 511.4 | 512.6 (M + H)$^+$ |
| 3 | $C_{40}H_{81}N_9O_5$ | 767.6 | 768.7 (M + H)$^+$ |
| 4 | $C_{52}H_{105}N_{13}O_7$ | 1023.8 | 1047.0 (M + Na)$^+$ |
| 5 | $C_{66}H_{129}N_{17}O_{11}$ | 1336.0 | 1336.9 (M + H)$^+$ |
| 6 | $C_{66}H_{126}N_{14}O_{11}$ | 1291.0 | 1293.7 (M + H)$^+$ |

TABLE 6-continued

MALDI analysis of lipidated γ-AApeptides

| Lipo-γ-AApeptide | Formula | Mass calculated | Mass found |
|---|---|---|---|
| 7 | $C_{60}H_{99}N_{11}O_{23}$ | 1341.6 | 1358.7 (M + NH4)$^+$ |
| 8 | $C_{72}H_{105}N_{11}O_{17}$ | 1395.8 | 1418.3 (M + Na)$^+$ |
| 9 | $C_{50}H_{96}N_{14}O_{10}$ | 1053.4 | 1054.0 (M + H)$^+$ |
| 10 | $C_{30}H_{59}N_5O_3$ | 537.5 | 538.6 (M + H)$^+$ |
| 11 | $C_{36}H_{71}N_7O_4$ | 666.0 | 666.6 (M + H)$^+$ |
| 12 | $C_{42}H_{83}N_9O_5$ | 793.7 | 816.8 (M + Na)$^+$ |
| 13 | $C_{68}H_{128}N_{14}O_{11}$ | 1317.0 | 1318.5 (M + H)$^+$ |

Examples of lipidated γ-AApeptides of the current invention are described in FIG. 12, named as sequence 1 to sequence 13. Sequences 1-6 are cationic lipidated γ-AApeptides with saturated lauric acid or palmitic acid tails. Sequences 7 and 8 are anionic lipidated γ-AApeptides that were prepared as negative controls. Sequence 9 contains the same γ-AApeptide sequence as 6, yet lacks an alkyl tail. Sequences 10-13 are cationic γ-AApeptides alkylated with unsaturated oleic acid.

3. Antimicrobial Assays

The sequences shown in FIG. 12 were tested for their antimicrobial activity toward a range of Gram-positive and Gram-negative bacteria, as well as the fungus C. albicans. Their selectivity was also evaluated via hemolytic assays. The results of these investigations are shown in Table 7, with γ5, a linear γ-AApeptide reported previously (Niu, Padhee et al., 2011), included for comparison.

The bacterial strains used in the experiment were E. coli (JM109), B. subtilis (BR151), multi-drug resistant S. epidermidis (RP62A), vancomycin-resistant E. faecalis (ATCC 700802), methicillin-resistant S. aureus (ATCC 33592), K. pneumoniae (ATCC 13383), and multi-drug resistant P. aeruginosa ATCC 27853. The fungal strain used was C. albicans (ATCC 10231). The antimicrobial activities of the lipidated γ-AApeptides were determined in a sterile 96-well plates by the broth micro-dilution method. Bacterial cells (Patch et al., 2003) and fungi (Karlsson et al., 2006) were grown overnight at 37° C. in 5 ml medium, after which a bacterial suspension (approximately 106 CFU/ml) or fungal suspension of Candida albicans (ATCC 10231) (approximately 103 CFU/ml) in Luria broth or trypticase soy was prepared. Aliquots of 50 μL bacterial or fungal suspension were added to 50 μL of medium containing the lipidated γ-AApeptides for a total volume of 100 μL in each well. The lipidated γ-AApeptides were prepared in PBS buffer in 2-fold serial dilutions, with the final concentration range of 0.5 to 100 μg/ml. Plates were then incubated at 37° C. for 24 h (for bacteria) or 48 h (for Candida albicans (ATCC 10231). The lowest concentration at which complete inhibition of bacterial growth (determined by a lack of turbidity) is observed throughout the incubation time is defined as the minimum inhibitory concentration (MIC). The experiments were carried out independently three times in duplicate.

As shown in Table 7, almost all the cationic lipidated γ-AApeptides display broad-spectrum antimicrobial activity against an array of Gram-negative and Gram-positive bacteria, as well as toward the fungus C. albicans. Sequences 7, 8, and 9, however, are not active at all under these experimental conditions. This is likely because, with a positively charged surface post-self-assembly, cationic lipidated γ-AApeptides selectively target bacteria that have negatively charged membranes. Sequences 7 and 8, which are negatively charged lipidated γ-AApeptides, should not, and do not, present any activity because of electrostatic repulsion with bacterial membranes. Linear sequence 9, although positively charged, cannot strongly interact with bacterial membranes because of its lack of a lipid tail.

selectivity may indicate that compared to membranes of mammalian cells bacterial membranes are more sensitive to unsaturated alkyl tails. This finding is significant for the

TABLE 7

Antimicrobial Activities of γ-AApeptides[a]
MIC (μg/ml)

| oligomers | Gram negative | | | Gram positive | | | | Fungi, | Hemolysis | |
| --- | --- | --- | --- | --- | --- | --- | --- | --- | --- | --- |
|  | E. coli | K. pneumoniae | P. aeruginosa | B. subtilis | S. faecalis | E. epidermidis | S. aureus | C. albicans | HC10/HC50 | selectivity[b] |
| 1 | >50 | >50 | >50 | >50 | >50 | >50 | >50 | >50 | 400/>500 |  |
| 2 | 2.5 | 35 | 10 | 1.5 | 2 | 2.5 | 2.5 | 2 | 25/40 | 16 |
| 3 | 30 | 20 | 20 | 1.5 | 2.5 | 8 | 5 | 2 | 40/300 | 60 |
| 4 | 20 | >50 | 15 | 1.5 | 2 | 10 | 5 | 2 | 300/>500 | >100 |
| 5 | 2.5 | 15 | 15 | 2.5 | 10 | 10 | 10 | 7.5 | 200/>500 | >50 |
| 6* | 2.5 | 5 | 5 | 2.5 | 4 | 5 | 4 | 5 | 60/>500 | >125 |
| 7 | >100 | >100 | >100 | >100 | >100 | >100 | >100 | >100 | 250/>500 |  |
| 8 | >100 | >100 | >100 | >100 | >100 | >100 | >100 | >100 | 200/>500 |  |
| 9 | >100 | >100 | >100 | >100 | >100 | >100 | >100 | >100 | 120/>500 |  |
| 10 | 2.5 | 35 | 3 | 2 | 2 | 2.5 | 4 | 2 | 40/100 | 25 |
| 11 | 10 | 40 | 15 | 2 | 2 | 2.5 | 5 | 5 | 80/>500 | >100 |
| 12 | 10 | 15 | 3 | 2.5 | 4 | 5 | 5 | 2 | 250/>500 | >100 |
| 13* | 3 | 3 | 3 | 3 | 3 | 4 | 3 | 3 | 100/>500 | >167 |
| γ5 | 3 | 5 | >50 | 2 | 5 | 5 | 5 | 8 | 75/300 | 60 |

[a]HC10 and HC50 are the concentrations of γ-AApeptides at which 10% or 50% hemolysis was observed. The two most potent and broad-spectrum lipo-γ-AApeptides, 6 and 13, are designated with an *.
[b]Selectivity is calculated based on H50/the MIC of S. aureus.

To investigate further development of lipidated γ-AApeptides based antimicrobial agents, the structure-function relationship of these compounds was investigated. Sequence 1, bearing one cationic γ-AApeptide building block and a lauric acid alkyl tail, is not active toward any microorganism. However, changing the lauric acid alkyl tail to a palmitic alkyl chain renders Sequence 2 a potent antimicrobial agent toward most bacteria, as well as the fungus C. albicans. This indicates that lipophilicity of the alkyl tail is highly important for interaction with cell membranes and that increased cationic charge does not necessarily lead to more potent antimicrobial agents. Sequence 3 and Sequence 4, which have many more cationic charges than Sequence 2, are seemingly less active toward bacteria and fungus. The balance of hydrophobicity and cationic charge appears to affect the antimicrobial activity. This led to the discovery of Sequence 5 and Sequence 6, with two more hydrophobic γ-AApeptide building blocks, which are more broadly active. Sequence 6, which is a lipidated version of Sequence 9, effectively arrests the growth of all tested bacteria and fungi. However, as lipophilicity increases, hemolytic activity also increases, compromising selectivity. To enhance selectivity, Sequences 10-13, which contain similar or identical sequences to Sequences 2-6 but with unsaturated oleic tails, were prepared. Unsaturated tails may have lesser propensity for aggregation but still possess the same hydrophobicity compared to their saturated counterparts.

A number of even more potent and broad-spectrum-active lipidated γ-AApeptides were obtained, some of which are much less hemolytic, as seen with Sequence 10, Sequence 12, and Sequence 13. For example, Sequence 3 and Sequence 12 only differ in their alkyl tails, yet Sequence 3 is somewhat hemolytic, while Sequence 12 is virtually nonhemolytic, and is generally more active towards bacteria. Sequence 13, being the most potent and broad-spectrum sequence, has similar and better antimicrobial activity than Sequence 6 toward all microorganisms, while it is again much less hemolytic. Such increased potency and enhanced development of novel lipoantibiotics. Both Sequence 13 and Sequence 6 are more potent and broad-spectrum than the linear sequence γ5 (Niu, Padhee et al., 2011), particularly toward the Gram-negative bacterium P. aeruginosa and fungus C. albicans, although they contain shorter lengths of γ-AApeptide fragments. Furthermore, Sequence 13 is less hemolytic than γ5. These results indicate that bacteria and fungi are more sensitive and susceptible to hydrophobic lipid chains, which supports the use of lipidated γ-AApeptides as novel antibiotic agents.

4. Hemolytic Assays

The sequences shown in FIG. 12 were also evaluated via hemolytic assays. Freshly drawn human red blood cells (hRBC's) with additive K2 EDTA (spray-dried) were washed with PBS buffer several times and centrifuged at 1000 g for 10 min until a clear supernatant was observed. The hRBC's were resuspended in 1×PBS to get a 5% v/v suspension. Two-fold serial dilutions of lipidated γ-AApeptides dissolved in 1×PBS from 1 mg/ml through 6.3 μg/ml were added to sterile 96-well plates to make up a total volume of 50 μL in each well. Then 50 μL of 5% v/v hRBC solution was added to make up a total volume of 100 μL in each well. The 0% hemolysis point and 100% hemolysis point were determined in 1×PBS and 0.2% Triton-X-100, respectively (Patch et al., 2003). The plate was then incubated at 37° C. for 1 h and centrifuged at 3500 rpm for 10 min. The supernatant (30 μL) was diluted with 100 μL of 1×PBS and absorption was detected by measuring the optical density at 360 nm with a Biotek Synergy HT microtiter plate reader. % hemolysis was determined by the following equation:

% hemolysis=(Abs sample−Abs PBS)/(Abs Triton−Abs PBS)×100

The results of the hemolytic assays are shown in Table 7.

5. Fluorescence Microscopy

To probe the antimicrobial mechanism of lipo-γ-AApeptide activity, fluorescence microscopy was performed to assess the ability of Sequence 13 (FIG. 13) and Sequence 6

(FIG. 14) to cause membrane leakage, since membrane disruption is a general function of AMPs. The double staining method with DAPI and PI was used, where DAPI stains all bacterial cells irrespective of their viability and PI only stains injured or dead cells with compromised membranes (Chen et al., 2010; Matsunaga et al., 1995). The cells were first stained with PI and then with DAPI. Bacterial cells were grown until they reached the mid-logarithmic phase and then they (~2×10⁶ cells) were incubated with the lipidated γ-AApeptides at the concentration of 2×MIC (10 µg/ml) for 2 h. Then the cells were pelleted by centrifugation at 3000 g for 15 min in an Eppendorf microcentrifuge. The supernatant was then decanted and the cells were washed with 1×PBS several times and then incubated with PI (5 µg/ml) in the dark for 15 min at 0° C. The excess PI was removed by washing the cells with 1×PBS several times. Then the cells were incubated with DAPI (10 µg/ml in water) for 15 mins in the dark at 0° C. The DAPI solution was removed and cells were washed with 1×PBS several times. Controls were performed following the exact same procedure for bacteria without the addition of γ-AApeptides. The bacterial cells were then examined by using the Zeiss Axio Imager Z1 optical microscope with an oil-immersion objective (100×) (Williams et al., 1998).

Figure 13:
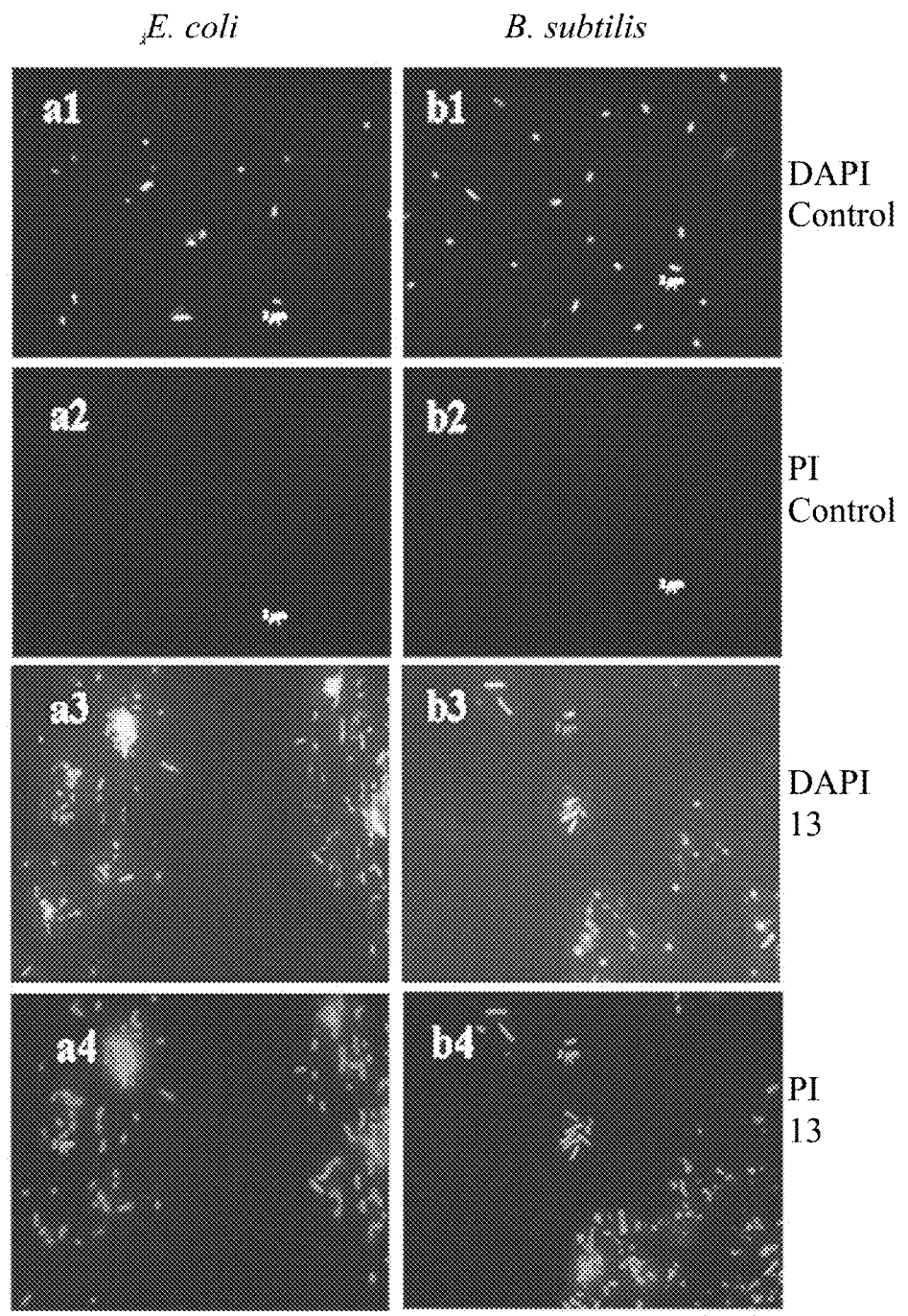
FIG. 13. Fluorescence micrographs of *E. coli* and *B. subtilis* treated with 10 μg/mL of lipidated γ-AApeptide, Sequence 13, for 2 h: (a1-a4) *E. coli*; (a1) control, no treatment, DAPI stained; (a2) control, no treatment, PI stained; (a3) Sequence 13 treatment, DAPI stained; (a4) Sequence 13 treatment, PI stained; (b1-b4) *B. subtilis*; (b1) control, no treatment, DAPI stained; (b2) control, no treatment, PI stained; (b3) Sequence 13 treatment, DAPI stained; (b4) Sequence 13 treatment, PI stained.
Figure 14:
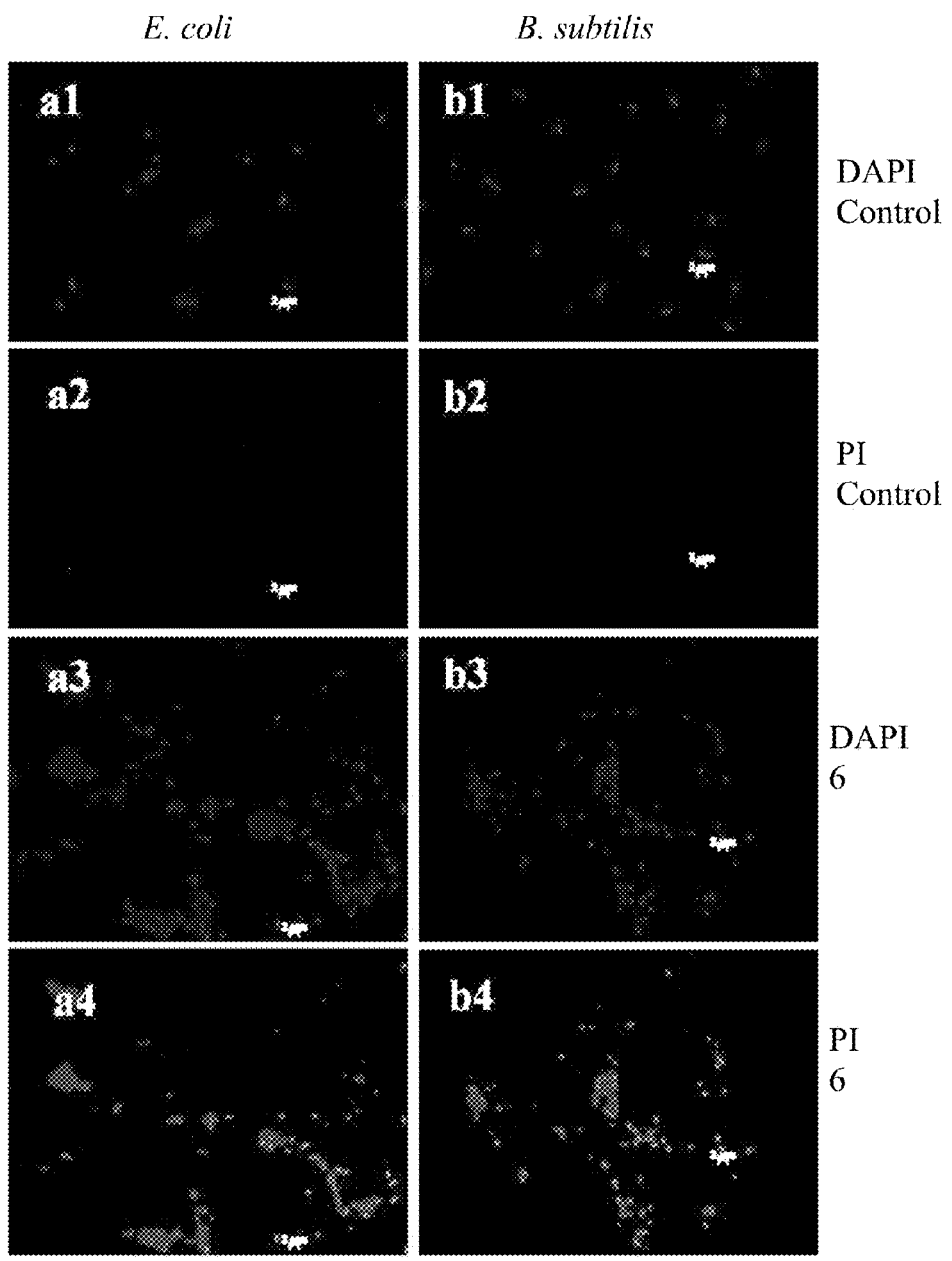
FIG. 14. Fluorescence micrographs of *E. coli* and *B. subtilis* treated with 10 jag/ml lipidated γ-AApeptide, Sequence 6, for 2 h. a1-a4, *E. coli*. a1, control, no treatment, DAPI stained; a2, control, no treatment, PI stained; a3, Sequence 6 treatment, DAPI stained; a4, Sequence 6 treatment, PI stained. b1-b4, *B. subtilis*. b1, control, no treatment, DAPI stained; b2, control, no treatment, PI stained; b3, Sequence 6 treatment, DAPI stained; b4, Sequence 6 treatment, PI stained. Scale bar: 2 μm for both bacteria.

Parts a1 and b1 of FIG. 13 show that, without treatment by Sequence 13, both *E. coli* and *B. subtilis* stained with DAPI but not PI, indicating that their membranes are intact. When cells were treated with Sequence 13 for 2 h, however, both *E. coli* and *B. subtilis* strongly stained with both DAPI (parts a3 and b3 of FIG. 13) and PI (parts a4 and b4 of FIG. 13), demonstrating membrane disruption. The aggregation of dead cells is also observed because of the loss of membrane potential, which is consistent with previous studies on antimicrobial peptide amphiphiles (Chen et al., 2010). Similar membrane disruption was also seen with the treatment of Sequence 6 (FIG. 14).

6. Lipid Depolarization (Wu et al., 1999; Choi et al., 2009; Friedrich et al., 2000)

The antimicrobial mechanism of membrane disruption for lipidated γ-AApeptides was further investigated using the membrane depolarization assay (DiSC$_3$-5 assay described above). *S. aureus* (ATCC 33592) cells were grown in Luria broth and Trypticase soy broth medium respectively to a mid-logarithmic phase (OD600=0.5-0.6). The bacterial cells were then collected by centrifugation at 3000 rpm for 10 min and then washed once with buffer (5 mM HEPES and 5 mM glucose, pH 7.2). The cells were re-suspended to OD600=0.05 with 100 mM KCl, 2 µM DiSC3-5.5 mM HEPES and 5 mM glucose and were incubated for 30 min at 37° C. for maximal dye uptake and fluorescence self-quenching. This bacterial suspension (50 µL) and 50 µL of lipidated γ-AApeptide stock solutions or control drug solution were added to white flat-bottomed polypropylene 96-well plates (Costar). The fluorescence reading was recorded every 2 min for 30 min using the microplate reader (Biotek) at an excitation wavelength of 622 nm and an emission wavelength of 670 nm. Valinomycin (final concentration 250 µg/mL) was used as a positive control, and the blank with only cells and dye was used as the background.

Figure 15:
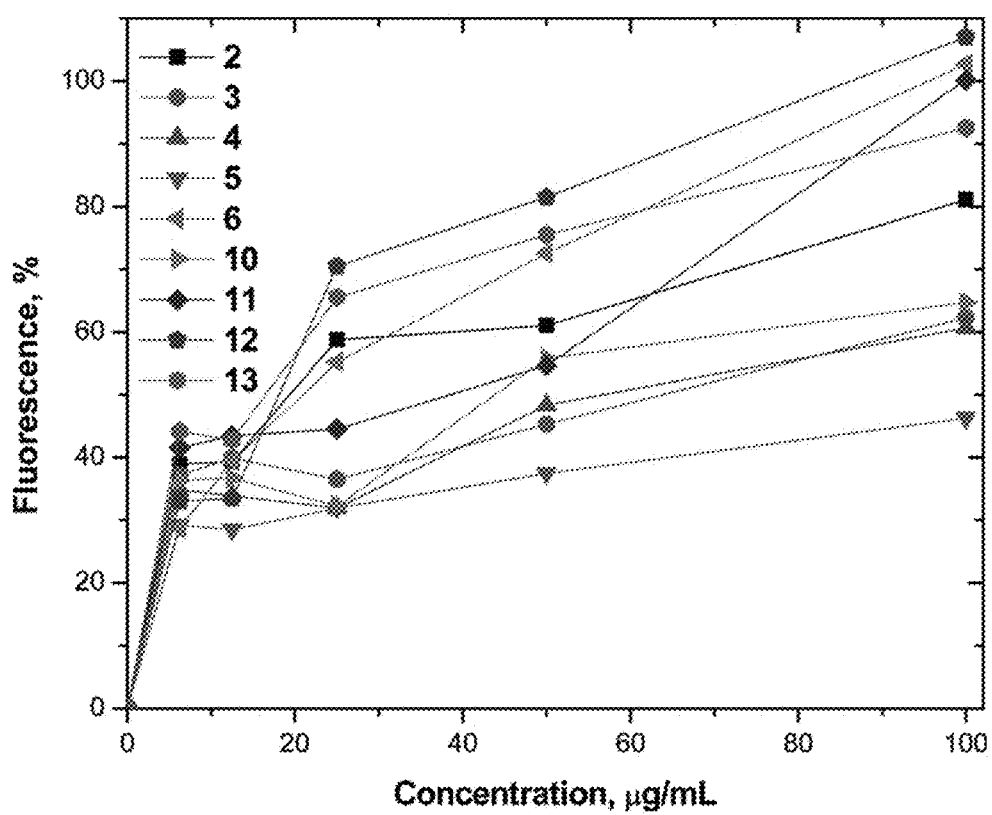
FIG. 15. Depolarization of the membrane of *S. aureus*. The fluorescence intensity of membrane potential-sensitive dye DiSC3 was used as the positive control.

MRSA, a clinically relevant and widely drug resistant bacterial pathogen, was selected for this study using the membrane potential-sensitive dye DiSC3 to test membrane integrity (Choi et al., 2009). Consistent with previous reports (Choi et al., 2009), our analysis shows that the concentrations of lipidated γ-AApeptides required for complete depolarization are much higher than their MICs, and there is no perfect relationship between the MIC and the capability for depolarization (FIG. 15). However, the treatment of MRSA with lipidated γ-AApeptides led to dramatically increased fluorescence, which was maximal after 10 min (FIG. 15). Meanwhile, there is a general trend that lipidated γ-AApeptides with higher MICs require higher concentrations to cause the same degree of depolarization than those with lower MICs. These data further suggest that lipidated γ-AApeptides kill bacteria via membrane disruption.

7. Drug Resistance Study

Figure 16:
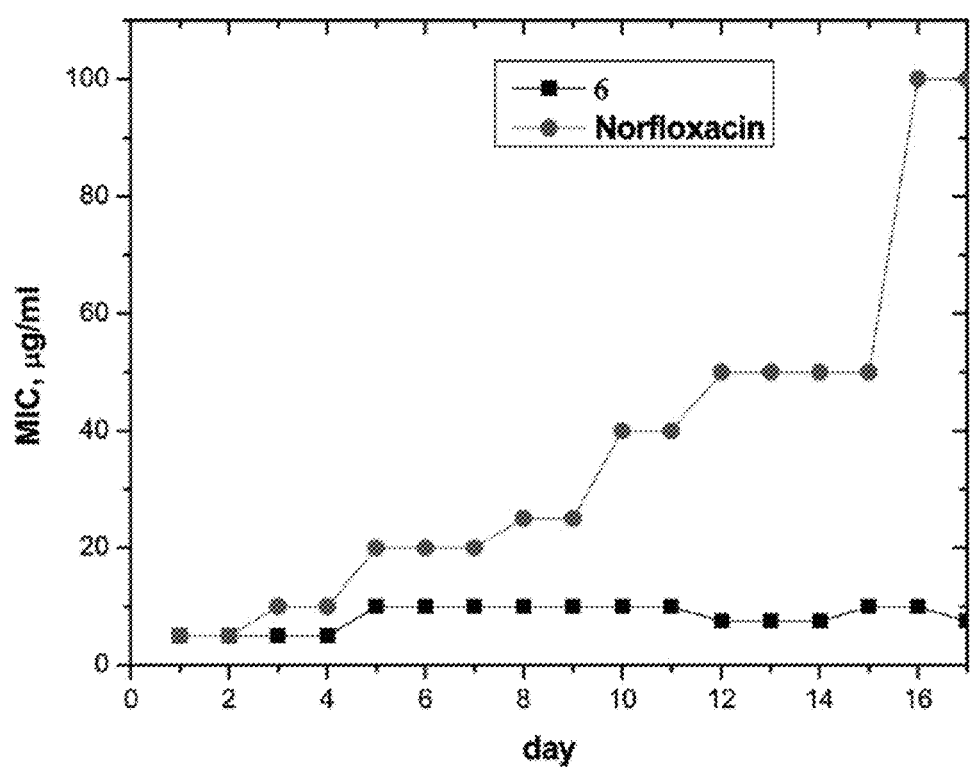
FIG. 16. Development of resistance by *S. aureus* ATCC 33592 toward lipidated γ-AApeptide, Sequence 6, and norfloxacin.

To investigate the potential of lipidated γ-AApeptides to select for drug-resistant isolates, methicillin-resistant *S. aureus* was serially passaged on half-MIC concentrations of Sequence 6, with new MIC values determined every 24 h. Sequence 6 was chosen as a representative sequence as a result of its broad spectrum of activity against test microorganisms. As a positive control, parallel cultures were exposed to 2-fold dilutions of the antibiotic norfloxacin (FIG. 16) (Choi et al., 2009).

The initial MIC of Sequence 6 and control antibiotic norfloxacin against *S. aureus* was obtained as described above. Bacteria from duplicate wells at the concentration of one-half MIC were then used to prepare the bacterial dilution (approximately 106 CFU/ml) for the next experiment. These bacterial suspensions were then incubated with Sequence 6 and norfloxacin respectively. After incubation at 37° C. for 24 h, the new MIC was determined. The experiment was repeated each day for 17 passages.

While there are almost no changes in the MIC for Sequence 6 after 17 days with 17 passages, an increase in MIC for norfloxacin was found after just three passages, with a more than 20-fold increase in MIC observed after 17 days. These findings further support that lipidated γ-AApeptides do not readily permit the development of drug resistance.

8. MTT Assay

Figure 17:
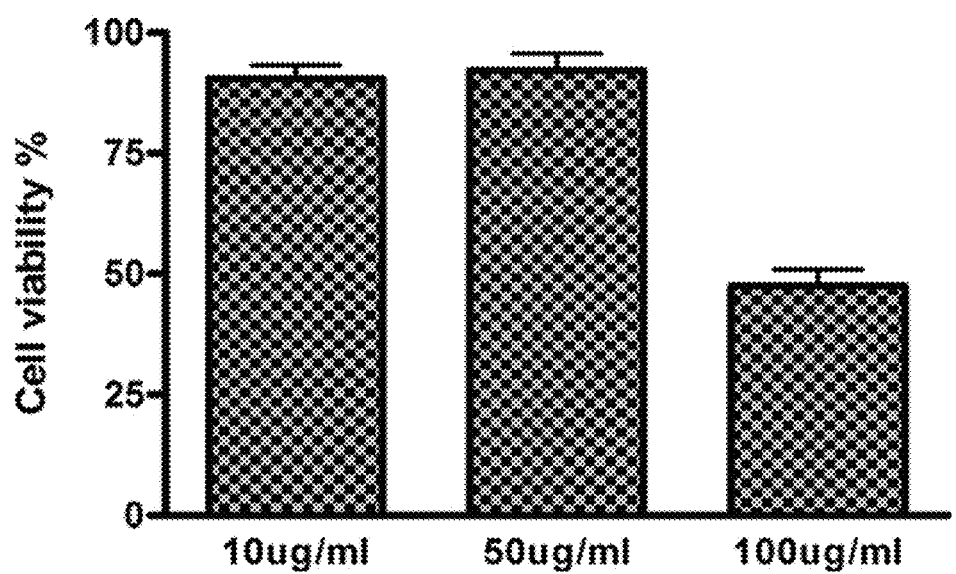
FIG. 17. MTT assay of N2a/APP cells treated with different concentrations of lipidated γ-AApeptide, Sequence 6.

To further assess the potential of γ-AApeptide amphiphiles as novel antibiotics, we also evaluated the toxicity of Sequence 6 toward mammalian cells using an MTT assay (FIG. 17). N2a APP cells were used to access the cell viability after treatment with Sequence 6. Typically, stock concentration of Sequence 6 (1 mg/mL) was diluted in medium in a 96-well plate to make different concentrations and then incubated at 37° C. In another 96-well plate, N2a APP cells were seeded to 1×10⁴ cells/well, each of which contained 100 µL of medium. After incubation for 12 h, an amount of 100 µL of different concentrations of Sequence 6 was added and the plate was incubated for another 36 h. At 1 h before time is due, MTT reagent (Roche) was incubated at 37° C. degree water bath. The medium in the 96-well plate was removed and washed with fresh medium once, followed by adding 110 µL of MTT reagent, and then incubated for another 4 h, after which 100 µL of prewarmed solubilization solution was added. The plate was then incubated at 37° C. for 12 h before absorbance at 550 nm was read. Percentage of cell viability was calculated based on the following equation:

Cell viability %=($A/A_{control}$)×100

At concentrations up to 50 µg/mL of Sequence 6, almost no toxicity was observed, while at 100 µg/mL of Sequence 6, only around 50% of N2a APP cell viability was compromised. These results show that selectivity is 10- to 50-fold lower than for bacteria, further demonstrating the feasibility of lipidated γ-AApeptides for use as antimicrobial therapeutics.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) of any other invention or embodiment thereof disclosed herein, and all such combinations are contemplated within the scope of the invention without limitation thereto.

REFERENCES

Chongsiriwatana, N. P., Patch, J. A., Czyzewski, A. M., Dohm, M. T., Ivankin, A., Gidalevitz, D., Zuckermann, R. N., and Barron, A. E. (2008) Peptoids that mimic the structure, function, and mechanism of helical antimicrobial peptides. *Proc Natl Acad Sci USA* 105, 2794-9.

Chongsiriwatana, N. P., Miller, T. M., Wetzler, M., Vakulenko, S., Karlsson, A. J., Palacek, S. P., Mobashery, S., and Barron, A. E. (2011) Short alkylated peptoid mimics of antimicrobial lipopeptides. *Antimicrob Agents Chemother.*, 55, 417-420.

Ge, Y., MacDonald, D. L., Holroyd, K. J., Thornsberry, C., Wexler, H., and Zasloff, M. (1999) In vitro antibacterial properties of pexiganan, an analog of magainin. *Antimicrob Agents Chemother* 43, 782-8.

Hicks, R. P., Bhonsle, J. B., Venugopal, D., Koser, B. W., and Magill, A. J. (2007) De novo design of selective antibiotic peptides by incorporation of unnatural amino acids. *J Med Chem* 50, 3026-36.

T. Matsunaga, M. Okochi and S. Nakasono, *Analytical chemistry*, 1995, 67, 4487-4490.

S. C. Williams, Y. Hong, D. C. A. Danavall, M. H. Howard-Jones, D. Gibson, M. E. Frischer and P. G. Verity, *Journal of Microbiological Methods*, 1998, 32, 225-236

J. A. Patch and A. E. Barron, *Journal of the American Chemical Society*, 2003, 125, 12092-12093.

A. K. Marr, W. J. Gooderham and R. E. Hancock, *Curr. opin. pharmacol.*, 2006, 6, 468-472.

R. E. Hancock and H. G. Sahl, *Nature biotechnol.*, 2006, 24, 1551-1557.

M. N. Alekshun and S. B. Levy, *Cell*, 2007, 128, 1037-1050.

N. P. Chongsiriwatana, J. A. Patch, A. M. Czyzewski, M. T. Dohm, A. Ivankin, D. Gidalevitz, R. N. Zuckermann and A. E. Barron, *PNAS*, 2008, 105, 2794-2799.

R. W. Scott, W. F. DeGrado and G. N. Tew, *Curr. opin. biotechnol.*, 2008, 19, 620-627.

M. Zaiou, *J. mol. med.* 2007, 85, 317-329.

A. Violette, S. Fournel, K. Lamour, O. Chaloin, B. Frisch, J. P. Briand, H. Monteil and G. Guichard, *Chem. bio.*, 2006, 13, 531-538.

G. N. Tew, R. W. Scott, M. L. Klein and W. F. Degrado, *Acc. chem. res.*, 2009, 43, 30-39.

S. A. Fowler and H. E. Blackwell, *Org. Biomol. Chem.*, 2009, 7, 1508-1524.

M. A. Schmitt, B. Weisblum and S. H. Gellman, *J. Am. Chem. Soc.*, 2007, 129, 417-428.

B. P. Mowery, S. E. Lee, D. A. Kissounko, R. F. Epand, R. M. Epand, B. Weisblum, S. S. Stahl and S. H. Gellman, *J. Am. Chem. Soc.*, 2007, 129, 15474-15476.

A. Ivankin, L. Livne, A. Mor, G. A. Caputo, W. F. Degrado, M. Meron, B. Lin and D. Gidalevitz, *Angew. Chem.* Int. ed., 2010, 49, 8462-8465.

Y. Niu, Y. Hu, X. Li, J. Chen and J. Cai, *New J. Chem.*, 2011, 35, 542-545.

Y. Niu, A. Jones, H. Wu, G. Varani and J. Cai, *Org. Biomol. Chem.*, 2011, DOI: 10.1039/C10B05738C.

S. Padhee, Y. Hu, Y. Niu, G. Bai, H. Wu, F. Costanza, L. West, L. Harrington, L. N. Shaw, C. Cao and J. Cai, *Chem. Commun.*, 2011, 47, 9729-9731.

S. Choi, A. Isaacs, D. Clements, D. Liu, H. Kim, R. W. Scott, J. D. Winkler and W. F. DeGrado, *PNAS*, 2009, 106, 6968-6973.

A. J. Karlsson, W. C. Pomerantz, B. Weisblum, S. H. Gellman and S. P. Palecek, *Journal of American Chemical Society*, 2006, 128, 12630-12631.

Y. Niu, S. Padhee, H. Wu, G. Bai, L. Harrington, W. N. Burda, L. N. Shaw, C. Cao and J. Cai, *Chem. Commun.*, 2011, 47, 12197-12199.

B. P. Mowery, A. H. Lindner, B. Weisblum, S. S. Stahl and S. H. Gellman, *J. Am. Chem. Soc.*, 2009, 131, 9735-9745.

C. Chen, F. Pan, S. Zhang, J. Hu, M. Cao, J. Wang, H. Xu, X. Zhao and J. R. Lu, *Biomacromolecules*, 2010, 11, 402-411.

Wu, M.; Maier, E.; Benz, R.; Hancock, R. E. W., *Biochemistry*, 1999, 38, 7235-7242.

Friedrich, C. L.; Moyles, D.; Beveridge, T. J.; Hancock, R. E., *Antimicrob Agents Chemother*, 2000, 44, 2086-92.

We claim:

1. A method of making a γ-AApeptide, the method comprising:

reacting an Fmoc protected amino aldehyde comprising:

FmocHN—CH(R₁)—CHO wherein $R_1$ is a straight or branched chain $C_1$ to $C_{10}$ alkyl group, $-CH_2-CH_2-S-CH_3$; a $-(CH_2)_{1-5}$-aryl group, or an $-(CH_2)_{1-5}$-heteroaryl group, and wherein the alkyl group, the aryl group or the heteroaryl group can be substituted or unsubstituted, with glycine benzyl ester comprising:

H₂N-CH₂-C(O)-O-CH₂-C₆H₅, to form a secondary amine comprising:

FmocHN—CH(R₁)—CH₂—NH—CH₂—C(O)—O—CH₂—C₆H₅, reacting

FmocHN—CH(R₁)—CH₂—NH—CH₂—C(O)—O—CH₂—C₆H₅, with a substituted or unsubstituted aryl, substituted or unsubstituted 5-membered heterocyclic ring of which one to four member(s) may be heteroatoms, γ-Boc-amino butyric acid, di-Boc-guanidinopropionic acid, mono-allyl succinate or substituted or unsubstituted alkanoic acid followed by hydrogenation to form γ-AApeptide building blocks comprising:

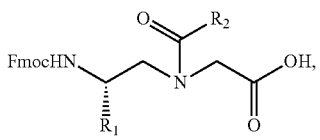

wherein $R_2$ is substituted or unsubstituted aryl, substituted or unsubstituted 5-membered heterocyclic ring of which one to four member(s) may be heteroatoms, amino-propyl, allyl-propyl, or substituted or unsubstituted alkyl;

attaching a first γ-AApeptide building block to a solid support;

coupling the first γ-AApeptide building block with a second γ-AApeptide building block;

repeating the coupling step to form the γ-AApeptide attached to the solid support; and cleaving the γ-AApeptide attached to the solid support from the solid support to form the γ-AApeptide.

2. The method of claim 1, wherein the solid support is a Rink amide resin or a Knorr resin.

3. The method of claim 1, wherein $R_1$ is a methyl, ethyl, n-propyl, isopropyl, cyclopropyl, n-butyl, isobutyl, s-butyl or t-butyl group.

4. The method of claim 1, wherein the repeating step is preformed to couple between 5 and 50 γ-AApeptide building blocks.

5. The method of claim 1, wherein the step of reacting an Fmoc protected amino aldehyde with glycine benzyl ester further comprises sodium cyanoborohydride.

6. The method of claim 1, wherein the step of reacting

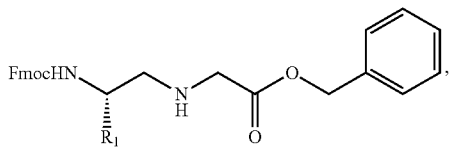

with the substituted or unsubstituted aryl, substituted or unsubstituted 5-membered heterocyclic ring of which one to four member(s) may be heteroatoms, γ-Boc-amino butyric acid, di-Boc-guanidinopropionic acid, mono-allyl succinate or substituted or unsubstituted alkanoic acid further comprises diisopropylcarbodiimide, 3-4-dihydro-3-hydroxy-4-oxo-1-2-3-benzotriazine, and dimethylformamide.

7. The method of claim 1, wherein hydrogenation to form γ-AApeptide building blocks comprises a palladium on carbon catalyst and molecular hydrogen.

8. The method of claim 1, wherein attaching a first γ-AApeptide building block to a solid support further comprises N,N'-Diisopropylcarbodiimide and oxohydroxybenzotriazole.

9. The method of claim 1, wherein coupling the first γ-AApeptide building block with a second γ-AApeptide building block further comprises N,N'-Diisopropylcarbodiimide and oxohydroxybenzotriazole.

10. The method of claim 1, wherein coupling the first γ-AApeptide building block with a second γ-AApeptide building block further comprises benzotriazol-1-yl-oxytripyrrolidinophosphonium hexafluorophosphate.

11. The method of claim 1, wherein coupling the first γ-AApeptide building block with a second γ-AApeptide building block further comprises 2-(1H-benzotriazol-1-yl)-1,1,3,3-tetramethyluronium hexafluorophosphate and hydroxybenzotriazole.

12. The method of claim 1, wherein cleaving the γ-AApeptide attached to the solid support from the solid support to form the γ-AApeptide further comprises trifluoroacetic acid, methylene chloride, and triisopropylsilane.

13. The method of claim 1, wherein the γ-AApeptide is a cyclic γ-AApeptide.

14. The method of claim 1, further comprising: purifying the γ-AApeptide by high performance liquid chromatography.

15. The method of claim 10, further comprising: lyophizing the γ-AApeptide.

16. The method of claim 1, further comprising: lyophizing the γ-AApeptide.

17. The method of claim 1, wherein the substituted or unsubstituted alkanoic acid is ethanoic acid or 4-methyl pentanoic acid.

18. The method of claim 1, wherein the substituted or unsubstituted 5-membered heterocyclic ring is selected from furanyl, thienyl, pyrrolyl, N-alkyl pyrrolyl, or imidazole.

19. The method of claim 1, wherein the substituted or unsubstituted aryl is a substituted or unsubstituted hydrocinnamic acid.

20. The method of claim 19, wherein the substituted or unsubstituted hydrocinnamic acid is α-cyano-4-hydroxycinnamic acid.

* * * * *

UNITED STATES PATENT AND TRADEMARK OFFICE
CERTIFICATE OF CORRECTION

PATENT NO. : 10,144,764 B2
APPLICATION NO. : 15/292162
DATED : December 4, 2018
INVENTOR(S) : Jianfeng Cai et al.

Page 1 of 1

It is certified that error appears in the above-identified patent and that said Letters Patent is hereby corrected as shown below:

In the Specification

Column 2,
Line 57, "Ca-peptide" should read --α-peptide--.

Column 3,
Line 43, "10 jag/ml" should read --10 µg/ml--.

Column 12,
Line 63, "II (ml)" should read --II (m1)--.

Column 17,
Lines 6-7, "ca-cyano-4-hydroxy-cinnamic" should read --α-cyano-4-hydroxy-cinnamic--.

Column 27,
Line 66, "ca-cyano-4-hydroxy-cinnamic" should read --α-cyano-4-hydroxy-cinnamic--.

Column 34,
Line 10, "cacl: 582.3174." should read --cacl: 582.3174,--.

Column 37,
Lines 10-12, Table 7, "

| Gram positive | | | |
|---|---|---|---|
| B. subtilis | S. faecalis | E. epidermidis | S. aureus |

" should read

--

| Gram positive | | | |
|---|---|---|---|
| B. subtilis | S. epidermidis | E. faecalis | S. aureus |

--.

Signed and Sealed this
Twenty-second Day of October, 2019

Andrei Iancu
*Director of the United States Patent and Trademark Office*